US008680335B2

(12) United States Patent
Zhong et al.

(10) Patent No.: US 8,680,335 B2
(45) Date of Patent: Mar. 25, 2014

(54) PROCESSES OF ENANTIOSELECTIVELY FORMING AN AMINOXY COMPOUND AND AN 1,2-OXAZINE COMPOUND

(75) Inventors: Guofu Zhong, Singapore (SG); Min Lu, Singapore (SG); Di Zhu, Singapore (SG); Pei Juan Chua, Singapore (SG); Bin Tan, Singapore (SG)

(73) Assignee: Nanyang Technological University, Singapore (SG)

( * ) Notice: Subject to any disclaimer, the term of this patent is extended or adjusted under 35 U.S.C. 154(b) by 350 days.

(21) Appl. No.: 12/782,709

(22) Filed: May 18, 2010

(65) Prior Publication Data

US 2011/0224429 A1 Sep. 15, 2011

Related U.S. Application Data

(60) Provisional application No. 61/180,353, filed on May 21, 2009, provisional application No. 61/241,157, filed on Sep. 10, 2009.

(51) Int. Cl.
*C07C 209/38* (2006.01)
*C07D 265/02* (2006.01)

(52) U.S. Cl.
USPC .......... 564/300; 544/63

(58) Field of Classification Search
USPC .......... 564/300
See application file for complete search history.

(56) References Cited

PUBLICATIONS

Guo et al. Green Chemistry (2006), 8(8), 682-684.*
Aggarwal, VK, et al., Org. Lett. (2002) 4, 1227.
Akiyama, Chem. Rev. (2007) 107, 5744-5758.
Al-Harrasi, A, &Reissig, H.-U., Angew. Chem. Int. Ed. (2005) 44, 6227.
Berner, OM, et al., Eur. J.Org. Chem. (2002) 1877-1894.
Bøgevig et al., Angew. Chem., Int. Ed, (2004) 43, 1109).
Bolm, et al., Angew. Chem. Int. Ed. (2005) 44, 1758-1763.
Brown et al., J. Am. Chem. Soc. (2003) 125, 10808.
Buchholz, M., Reissig, H.-U. Eur. J. Org. Chem. (2003) 3524.
Carson, C. A., & Kerr, M.A., Angew. Chem. Int. Ed. (2006) 45, 6560.
Cheon, H. Yamamoto, J. Am. Chem. Soc. (2008) 130, 9246-9247.
Cheong, K. N. Houk, J. Am. Chem. Soc. (2004) 126, 13912-13913.
Cobb, et al., Chem. Commun. (2004) 1808-1809.
Connon, Angew. Chem. Int. Ed. (2006) 45, 3909-3912.
Córdova, et al., Chem. Eur. J. (2004) 10, 3673.
Defoin, A, Synthesis (2004) 706-710.
Doyle, E. N. Jacobsen, Chem. Rev. 2007, 107, 5713-5743.
Enders, J. Wiedemann, Synthesis (1996) 1443-1450.
Font et al., Org. Lett. (2007) 9, 1943.
Guo et al., Green Chem. (2006) 8, 682.
Hartikka, P. I. Arvidsson, Tetrahedron: Asymmetry (2004) 15, 1831-1834.
Hayashi et al., Angew. Chem., Int. Ed. (2004) 43, 1112.
Hayashi et al., Tetrahedron Lett. (2003) 44, 8293.
Hayashi, et al., Adv. Synth. Catal. (2004) 346, 1435.
Hayashi, Y, et al., J. Org. Chem. (2004) 69, 5966.
Iwamura, et al., J. Am. Chem. Soc. (2004) 126, 16312-16313.
Iyengar, R, et. al., J. Org. Chem. (2005) 70, 10645.
Judd, T. C., & Williams, R. M., Angew. Chem., Int. Ed. (2002) 41, 4683.
Kamimura, et al., TetrahedronLett. (2006) 47, 2471-2473.
Kano et al., Chem. Lett. (2008) 37, 250.
Katoh, T., et al., Tetrahedron (1997) 53, 10229.

(Continued)

*Primary Examiner* — Kahsay Habte
(74) *Attorney, Agent, or Firm* — Sam K. Tahmassebi; TechLaw LLP

(57) ABSTRACT

Disclosed is a process of enantioselectively forming an aminoxy compound of Formula (3)

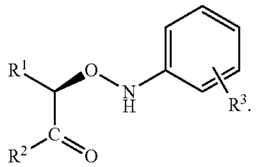

In formula (3) $R^1$ is one of an aliphatic group and an alicyclic group. $R^2$ is one of hydrogen, an aliphatic group, an alicyclic group, an aromatic group, an arylaliphatic group and an arylalicyclic group. $R^3$ is one of hydrogen, halogen, hydroxyl, and an aliphatic group with a main chain having 1 to about 10 carbon atoms. The respective aliphatic, alicyclic, aromatic, arylaliphatic or arylalicyclic groups of $R^1$, $R^2$, and $R^3$ comprise 0 to about 3 heteroatoms independently selected from the group consisting of N, O, S, Se and Si. The process includes contacting a carbonyl compound of Formula (1)

(1)

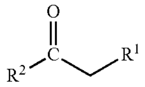

and a nitroso compound of Formula (2)

(2)

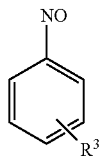

in the presence of a chiral catalyst. The chiral catalyst is a compound of Formula (IX)

IX

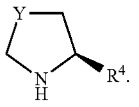

5 Claims, 38 Drawing Sheets

(56) References Cited

PUBLICATIONS

Kim & T. H. Park, Tetrahedron Lett. (2006) 47, 6369.
Kim & T.-H. Park, Tetrahedron Lett. (2006) 47, 9067.
Kodukulla, RPK, et al., Synth. Commun. (1994) 24, 819.
Kornblum, N, & Weaver, WM, J. Am. Chem. Soc. (1958) 80, 4333.
Kotkar et al., Tetrahedron: Asymmetry (2007) 18, 1795.
Kotkar& A. Sudalai, Tetrahedron Lett. (2006) 47, 6813.
Kumarn. David, et al., Chem. Commun. (2006) 3211.
Leow,et al., Angew. Chem. Int. Ed. (2008) 47, 5641-5645.
Lu, et al., Angew. Chem., Int. Ed., (2008) 47, 10187.
Lucet, et al., Eur. J. Org. Chem. (2000) 3575-3579.
Mangion& D. W. C. MacMillan, J. Am. Chem. Soc. (2005) 127, 3696.
Marcelli et al., Angew. Chem. Int. Ed. (2006) 45, 7496-7504.
Mathew, H. Iwamura, Angew. Chem. Int. Ed. (2004) 43, 3317-3321.
Momiyama et al., Proc. Natl. Acad. Sci. USA (2004) 101, 5374.
Momiyama, N, et al., J. Am. Chem. Soc. (2007) 129, 1190-1195.
More, JD, &Finney,NS, Org. Lett. (2002) 4, 3001.
Narina& A. Sudalai, Tetrahedron Lett. (2006) 47, 6799.
Palomo, C., et al., Angew. Chem. Int. Ed. (2007) 46, 8054.
Pihko, Angew. Chem. Int. Ed. (2004) 43, 2062-2064.
Pulz, R., et al., Org. Lett. (2002) 4, 2353.
Ramachary& I. C. F. Barbas, Org. Lett. (2005) 7, 1577.
Schreiner, Chem. Soc. Rev. 2003, 32, 289-296.
Sibi, et al., J. Am. Chem. Soc. (2005) 127, 5764-5765.
Hara et al., Tetrahedron Lett. (2006) 47, 1081.
Southwick, J. E. Anderson, J.Am. Chem. Soc. (1957) 79, 6222-6229.
Sundén et al., TetrahedronLett. (2005) 46, 3385.
Suzuki, M., et al., Angew. Chem. Int. Ed. (2002) 41, 4686.
Takemoto, Org. Biomol. Chem. (2005) 3, 4299-4306.
Tan, et al., Org. Lett. (2008) 10, 2437.
Tan, et al., Org. Lett. (2008) 10, 3425.
Taylor, E. N. Jacobsen, Angew. Chem. Int. Ed. 2006, 45, 1520-1543.
Terano, H.; et al., J. Antibiot. (1989) 42,145.
Tietze, L. F.; Beifuss, U., Angew. Chem. Int. Ed. (1985) No. 12, 1042-1043.
Tishkov, A.A., et al., Synlett (2002) 863.
Uchida, I., et al., J. Am. Chem. Soc. (1987) 109, 4108.
Kohn, Tetrahedron: Asymmetry (2007) 18, 1735-1741.
Wang et al., TetrahedronLett. (2004) 45, 7235.
Yamamoto, Y, et al., J. Am. Chem. Soc. (2004) 126, 5962-5963.
Yu Q., et al., J. Med. Chem. (2002) 45, 3684.
Zhong& Y. Yu, Org. Lett. (2004) 6, 1637.
Zhong, Angew. Chem., Int. Ed. (2003) 42, 4247.
Zhong, Chem. Commun. (2004) 606.
Zhou, Gang; Hu, Qi-Ying; Corey, E. J., rg. Lett. (2003) 5, 3979-3982.
Zhu, et al., J. Mol. Biol. (2004) 343, 1269.
Zhu, et al., Org. Lett. (2008) 10, 4585.

* cited by examiner (1) (2) (3)

(1) (2) (4)

(9) (2) (13)

(13) (14) (15)

(9) (2) (16)

(16) (17) (18)

(21) (2) (23)

(23) (24) (25)

(21) (2) (26)

(26) (27) (28)

(31) (2) (33)

(33) (34) (35)

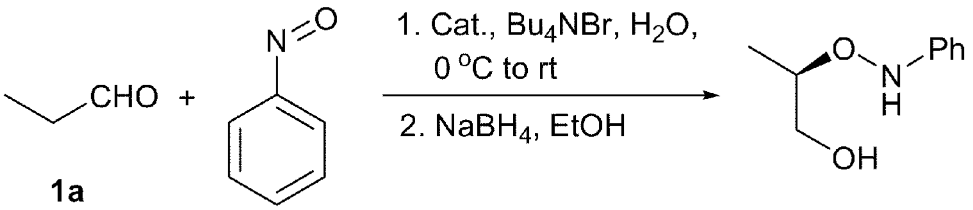
1a 2a 9a
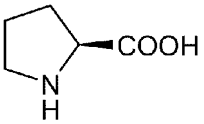
IXa
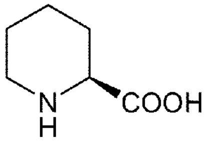
Xa
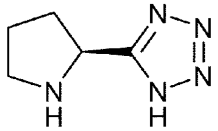
IXb
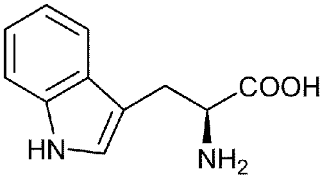
XL
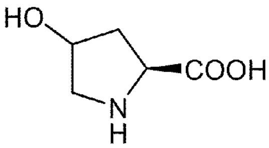
IXc
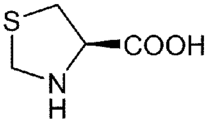
IXd
| Entry | Catalyst | Time | Yield[a] (%) | ee[b] (%) |
|---|---|---|---|---|
| 1 | **IXa** | 1 h | 64 | 96 |
| 2 | **Xa** | 6 h | 39 | 43 |
| 3 | **IXb** | 20 min | 62 | 96 |
| 4 | **XL** | 30 min | 14 | 23 |
| 5 | **IXc** | 30 min | 65 | 82 |
| **6** | **IXd** | **1 h 40 min** | **75** | **93** |
Fig. 4

1a 2a 9a

| Entry | Solvent | Vol of Solvent | Time | Yield[a] (%) | ee[b] (%) |
|---|---|---|---|---|---|
| 1[c] | $H_2O$ | 0.10 mL | 2 h 10 min | 78 | 93 |
| **2** | **$H_2O$** | **0.10 mL** | **2h** | **84** | **96** |
| 3[d] | $H_2O$ | 0.10 mL | 1 h 40 min | 75 | 93 |
| 4 | — | 0.10 mL | 1 h 15 min | 62 | 94 |
| 5 | $CHCl_3$ | 0.10 mL | 1 h 50 min | 60 | 92 |
| 6 | DMSO | 0.10 mL | 2 h 15 min | 68 | 90 |
| 7 | $CH_3CN$ | 0.10 mL | 3 h 50 min | 73 | 97 |
| 8 | $H_2O$ | 0.05 mL | 2 h 20 min | 56 | 93 |
| 9 | $H_2O$ | 0.20 mL | 2 h 10 min | 67 | 96 |
| 10 | $H_2O$ | 0.30 mL | 1 h 45 min | 58 | 93 |
| 11[e] | $H_2O$ | 0.10 mL | 1 h 55 min | 62 | 94 |
| 12[f] | $H_2O$ | 0.10 mL | 1 h 45 min | 62 | 95 |
| 13[g] | $H_2O$ | 0.10 mL | 2 h 15 min | 52 | 90 |
| 14[h] | $H_2O$ | 0.10 mL | 2 h 25 min | 54 | 92 |

Fig. 6
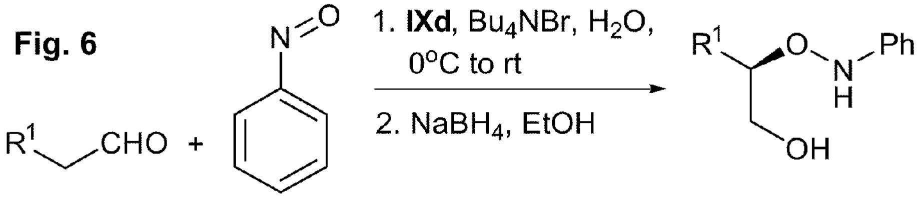
1a-k 2a 9a-k
| Entry | $R^1$ | | Time | Yield[b] (%) | ee[c] (%) |
|---|---|---|---|---|---|
| 1 | Me | **3a** | 2 h | 84 | 96 |
| 2 | Et | **3b** | 2 h 10 min | 75 | 98 |
| 3 | Pr | **3c** | 2 h 20 min | 79 | 97 |
| 4 | Bu | **3d** | 2 h 35 min | 74 | 96 |
| 5 | *i*-Pr | **3e** | 2 h 10 min | 76 | 97 |
| 6 | Ph | **3f** | 20 min | 78 | 93 |
| 7 | $PhCH_2$ | **3g** | 2 h 30 min | 77 | > 99 |
| 8 | $CH_2$=$CHCH_2$ | **3h** | 1 h | 88 | 96 |
| 9 | $BnOCH_2CH_2$ | **3i** | 2 h 20 min | 86 | 97 |
| 10 | $BocNHCH_2$ | **3j** | 2 h 30 min | 79 | 93 |
| 11[d] | Me | **3k** | 2 h 20 min | 83 | 97 |
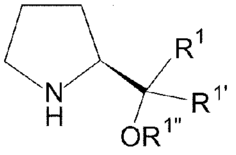
IXe
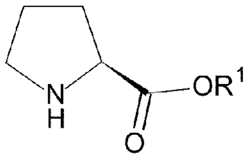
IXf
Fig. 7A
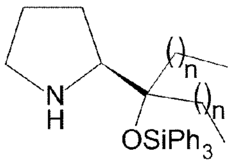
IXg
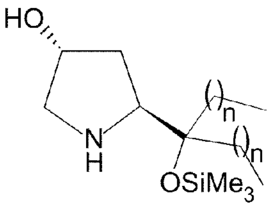
IXh Fig. 8
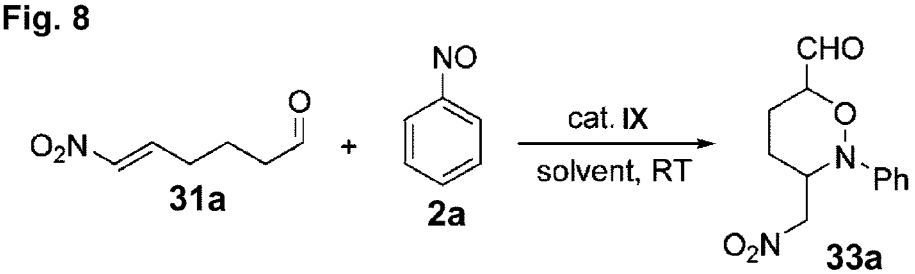
31a
2a
33a
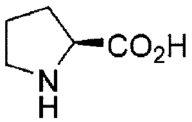
IXa
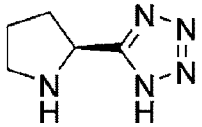
IXb
| Entry | IX (mol %) | Solvent | t [h] | Yield [%][a] | ee[%][b] | d.r.[c] |
|---|---|---|---|---|---|---|
| 1 | IXa (20) | DMSO | 0.5 | 46 | 99 | > 99:1 |
| 2 | IXa (20) | DMF | 0.5 | 44 | 99 | > 99:1 |
| 3 | IXa (20) | $CH_3CN$ | 0.5 | 55 | 99 | > 99:1 |
| 4 | IXa (20) | $CHCl_3$ | 0.5 | 53 | 98 | > 99:1 |
| 5 | IXa (20) | THF | 24 | < 20 | n.d. | n.d. |
| 6 | IXa (20) | $H_2O$ | 48 | < 5 | n.d. | n.d. |
| 7 | IXb (20) | $CH_3CN$ | 0.5 | 49 | 99 | > 99:1 |
| 8[d] | IXa (20) | $CH_3CN$ | 0.5 | 59 | 99 | > 99:1 |
| 9[d,e] | IXa (20) | $CH_3CN$ | 1 | 63 | > 99 | > 99:1 |
| 10[d,f] | IXa (20) | $CH_3CN$ | 2 | 67 | > 99 | > 99:1 |
| 11[d,f] | IXa (20) | $CH_3CN$ | 24[g] | 73 | > 99 | > 99:1 |
| 12[d,f] | IXa (20)[h] | $CH_3CN$ | 14[g] | 90 | > 99 | > 99:1 |
| 13[d,f] | IXa (5)[h] | $CH_3CN$ | 24[g] | 90 | > 99 | > 99:1 |
| 14[d,f] | IXa (0.5)[h] | $CH_3CN$ | 72[g] | 77 | > 99 | > 99:1 |
| 15[d,f] | IXa (20)[h] | $CH_3CN$ | 8[g] | 88[i] | > 99 | 90:10 |

31

2a: R'=H 2b: R'=2-Me
2c: R'=4-Br 2d: R'=4-Me

33

| Entry | $R^8$ | ArNO | Yield [%][a] | ee[%][b] | d.r.[c] |
|---|---|---|---|---|---|
| 1 | H (31a) | 2a | 90 (5a) | > 99 | > 99:1 |
| 2 | H (31a) | 2b | 79 (5b) | 97 | > 99:1 |
| 3 | H (31a) | 2c | 88 (5c) | > 99 | > 99:1 |
| 4 | Me (31b) | 2a | 75 (5d) | 99 | > 99:1 |
| 5 | Me (31b) | 2c | 73 (5e) | 99 | > 99:1 |
| 6 | Et (31c) | 2a | 68 (5f) | > 99 | > 99:1 |
| 7 | Et (31c) | 2c | 60 (5g) | > 99 | > 99:1 |
| 8 | Ph (31d) | 2a | 73 (5h) | > 99 | > 99:1 |
| 9 | Bn (31e) | 2a | 50 (5i) | > 99 | > 99:1 |
| 10 | Bn (31e) | 2c | 66 (5j) | 99 | > 99:1 |
| 11 | $pMeC_6H_4CH_2$ (31f) | 2a | 47 (5k) | > 99 | > 99:1 |
| 12 | $pMeC_6H_4CH_2$ (31f) | 2c | 45 (5l) | > 99 | > 99:1 |
| 13 | $pClC_6H_4CH_2$ (31g) | 2a | 78 (5m) | > 99 | > 99:1 |
| 14 | $pClC_6H_4CH_2$ (31g) | 2c | 78 (5n) | > 99 | > 99:1 |
| 15 | $pBrC_6H_4CH_2$ (31h) | 2a | 75 (5o) | > 99 | > 99:1 |
| 16 | $pBrC_6H_4CH_2$ (31h) | 2c | 70 (5p) | 99 | > 99:1 |
| 17 | H (31a) | 2d | 90 (5q) | > 99 | > 99:1 |

33d 47 48 49

| Entry | Cat. (mol %) | T [°C] | t [h] | Conversion[a] |
|---|---|---|---|---|
| 1 | none | - 20 | 48 | n.r. |
| 2 | none | RT | 48 | n.r. |
| 3 | TEA (100) | RT | 48 | 31 |
| 4 | quinine (20) | RT | 18 | > 95 |

Fig. 12A
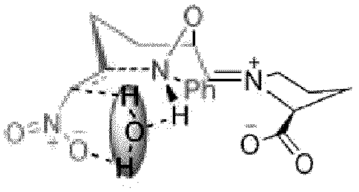
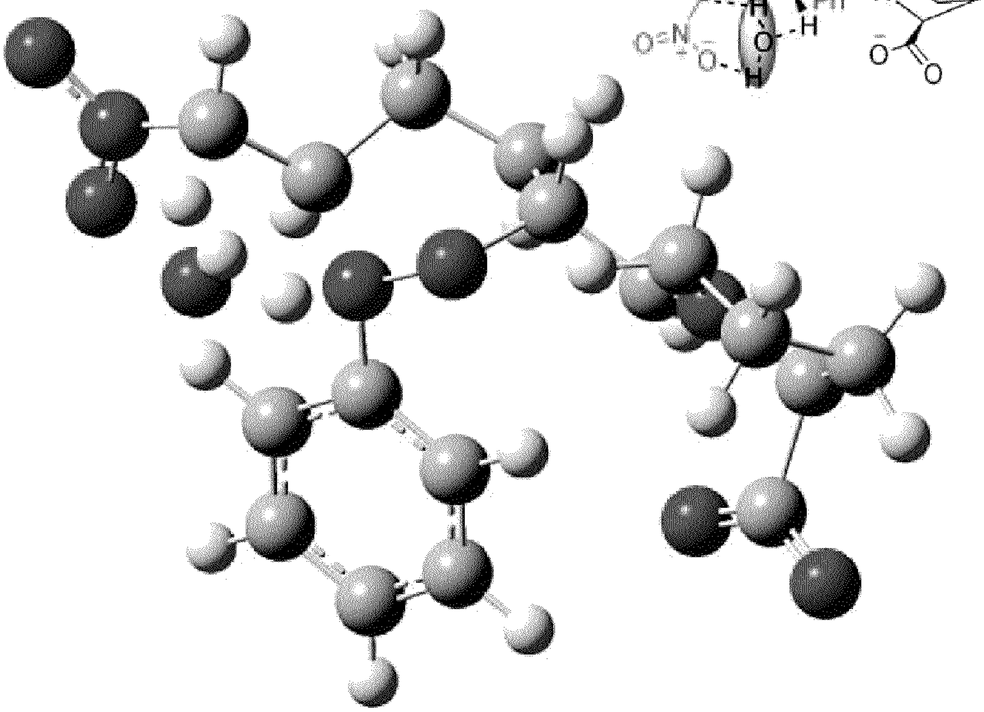
Fig. 12B
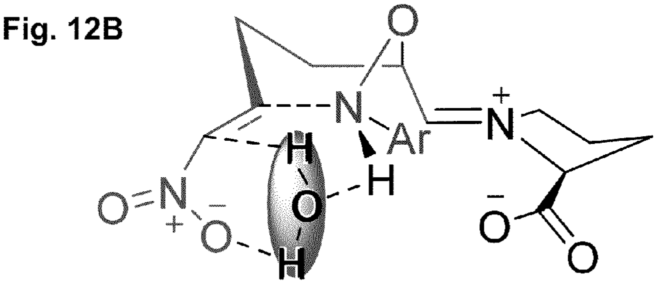

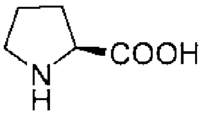
IXa
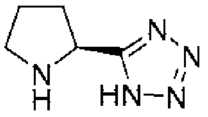
IXb
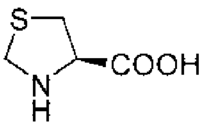
IXd
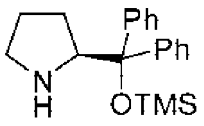
IXe
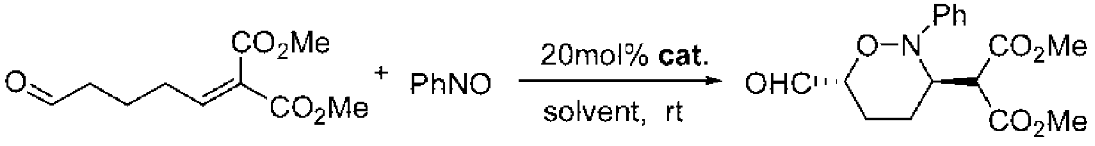
1.2 equiv 21a 1 equiv 2a 23a
Fig. 13
| entry | cat. | solvent | time | yield (%)[a] | dr[b] | ee (%)[b] |
|---|---|---|---|---|---|---|
| 1 | IXa | DMSO | 20 min | 37 | > 99:1 | 98 |
| 2 | IXb | $CH_3CN$ | 60 min | 34 | > 99:1 | 97 |
| 3 | IXd | DMSO | 45 min | 32 | > 99:1 | 98 |
| 4 | IXe | $CHCl_3$ | 60 min | < 10 | nd | nd |
| 5 | IXa | $CH_3CN$ | 60 min | 52 | > 99:1 | 98 |
| 6 | IXa | $CHCl_3$ | 60 min | 46 | > 99:1 | 98 |
| 7 | IXa | DMF | 45 min | 41 | > 99:1 | 98 |
| 8 | IXa | NMP | 45 min | 45 | > 99:1 | 98 |
| 9 | IXa | THF | 3 h | < 20 | nd | nd |
| 10 | IXa | DCM | 60 min | 31 | > 99:1 | 98 |
| 11[c] | IXa | $H_2O$ | 24 h | < 10 | nd | nd |

Fig. 14
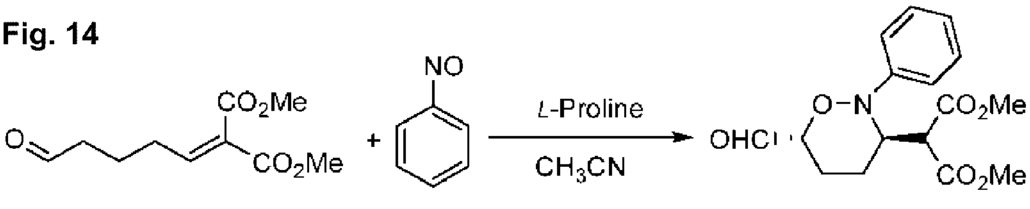
21a 2a 23a
| entry | equiv[a] | temp (°C) | cat. (%)[b] | time | yield (%)[c] | dr[d] | ee (%)[d] |
|---|---|---|---|---|---|---|---|
| 1 | 1.2 | 23 | 20 | 1 h | 52 | >99:1 | 98 |
| 2 | 1.2 | 0 | 20 | 3 h | 61 | >99:1 | 98 |
| 3 | 1.2 | - 20 | 20 | 24 h | 65 | >99:1 | 98 |
| 4 | 1.5 | - 20 | 20 | 18 h | 69 | >99:1 | 98 |
| 5 | 2 | - 20 | 20 | 16 h | 73 | >99:1 | 98 |
| 6 | 3 | - 20 | 20 | 13 h | 79 | >99:1 | 98 |
| 7 | 3 | - 20 | 10 | 18 h | 84 | >99:1 | 98 |
| 8 | 3 | - 20 | 5 | 24 h | 72 | >99:1 | 98 |
| 9[e] | 3 | - 20 | 10 | 24 h | 73 | 1:1 | nd |
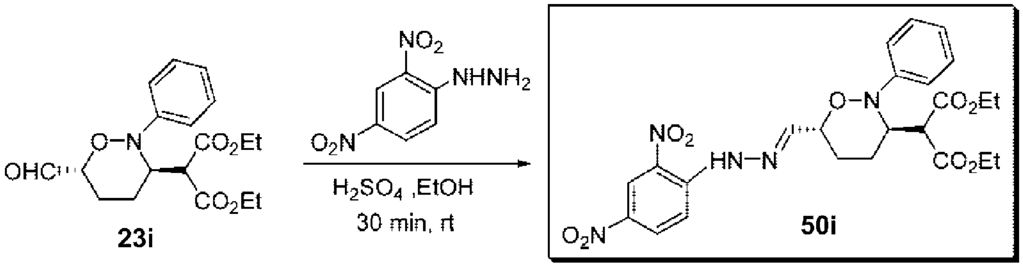
Fig. 15

21a-g 2a-h 23a-v

| entry | $R^9(=R^{10})$ | R′ | product | yield (%)[a] | dr[b] | ee (%)[b] |
|---|---|---|---|---|---|---|
| 1 | Me | H | 23a | 84 | > 99:1 | 98 |
| 2 | Me | 2-Me | 23b | 70 | > 99:1 | 94 |
| 3 | Me | 3-Me | 23c | 63 | > 99:1 | 98 |
| 4 | Me | 4-Me | 23d | 73 | > 99:1 | 99 |
| 5 | Me | 3-Cl | 23e | 65 | > 99:1 | 98 |
| 6 | Me | 4-Cl | 23f | 62 | > 99:1 | 99 |
| 7 | Me | 4-Br | 23g | 72 | > 99:1 | 99 |
| 8 | Me | 4-OPh | 23h | 52 | > 99:1 | 99 |
| 9 | Et | H | 23i | 73 | > 99:1 | 99 |
| 10 | Pr | H | 23j | 81 | > 99:1 | 99 |
| 11 | i-Pr | H | 23k | 69 | > 99:1 | 99 |
| 12 | Bu | H | 23l | 79 | > 99:1 | 99 |
| 13 | Pen | H | 23m | 67 | > 99:1 | 92 |
| 14 | Hex | H | 23n | 71 | > 99:1 | 99 |
| 15 | Et | 2-Me | 23o | 73 | > 99:1 | 95 |
| 16 | Pr | 2-Me | 23p | 72 | > 99:1 | 98 |
| 17 | i-Pr | 2-Me | 23q | 69 | > 99:1 | 96 |
| 18 | Bu | 2-Me | 23r | 71 | > 99:1 | 96 |
| 19 | Et | 4-Br | 23s | 67 | > 99:1 | 99 |
| 20 | Pr | 4-Br | 23t | 74 | > 99:1 | 99 |
| 21 | i-Pr | 4-Br | 23u | 67 | > 99:1 | 99 |
| 22 | Bu | 4-Br | 23v | 71 | > 99:1 | 99 |

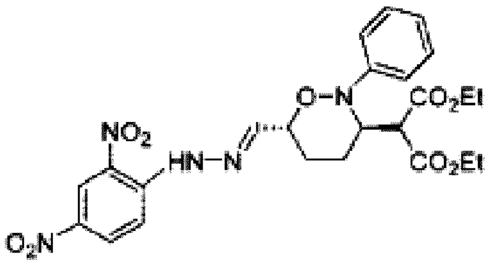
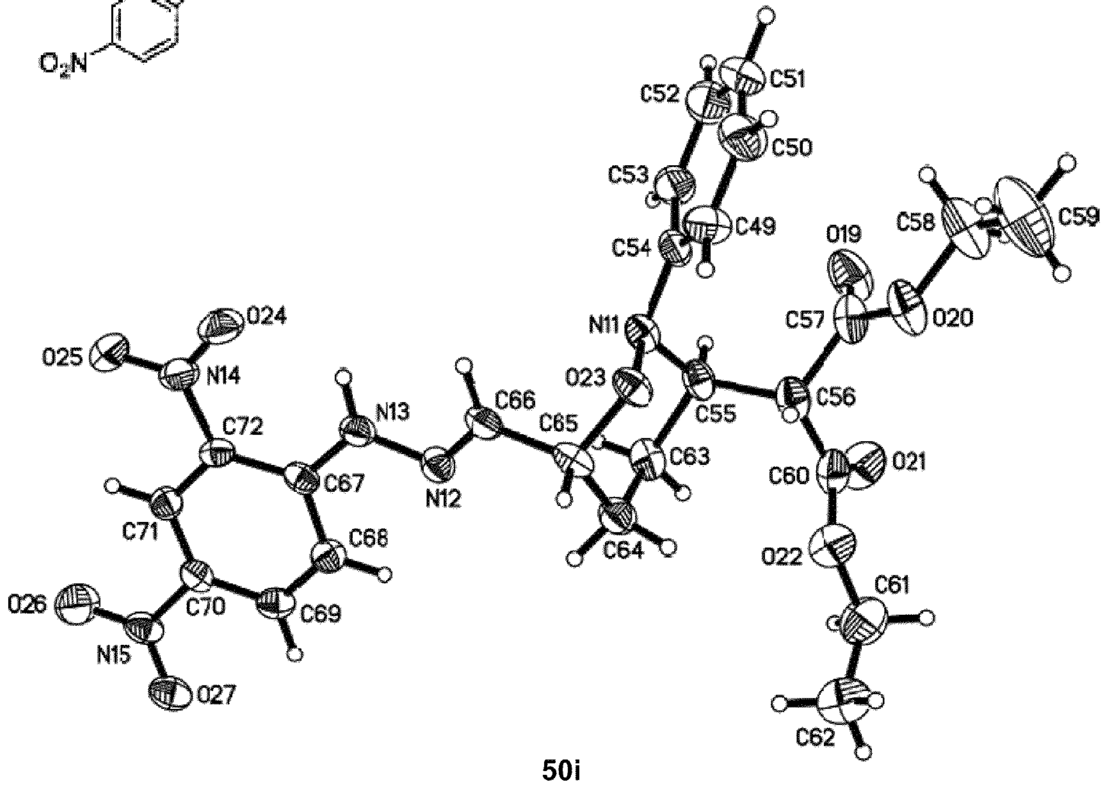
50i
Fig. 17

HPLC Spectra

9a

Peak Table

PDA Ch2 230nm 4nm

| Peak# | Ret. Time | Area % |
|---|---|---|
| 1 | 10.579 | 2.111 |
| 2 | 12.102 | 97.889 |
| Total | | 100.000 |

9a

Peak Table

PDA Ch2 230nm 4nm

| Peak# | Ret. Time | Area % |
|---|---|---|
| 1 | 10.577 | 50.695 |
| 2 | 12.107 | 49.305 |
| Total | | 100.000 |

c:hexane 85%
d:ipa 15%
AS H Column
Chromatogram
MLU-414 C:\LabSolutions\Data\MLu\MLU-414_AS_85_15-1.lcd
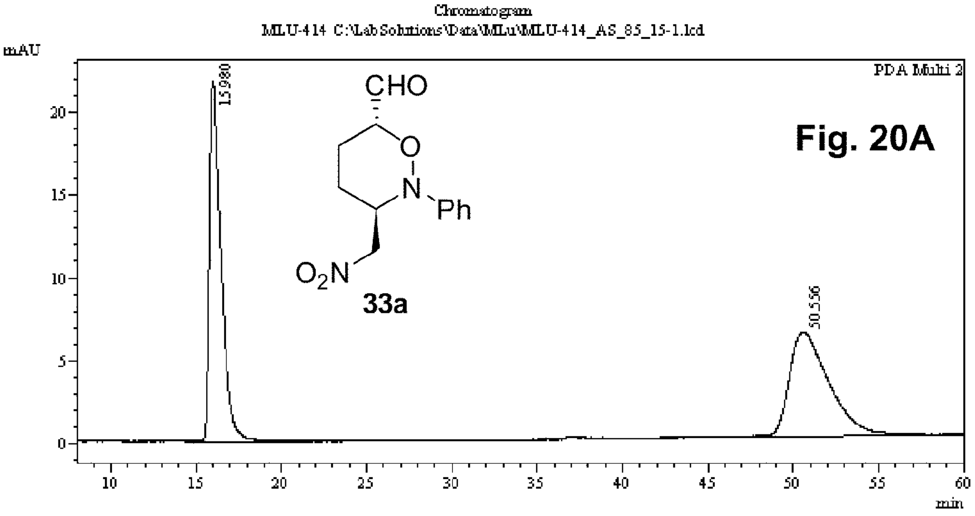
1 PDA Multi 2 / 230nm 4nm
PeakTable
PDA Ch2 230nm 4nm
| Peak# | Ret. Time | Area | Height | Area % | Height % |
|---|---|---|---|---|---|
| 1 | 15.980 | 1025839 | 21752 | 50.563 | 77.683 |
| 2 | 50.556 | 1002985 | 6249 | 49.437 | 22.317 |
| Total | | 2028824 | 28001 | 100.000 | 100.000 |
c:hexane 85%
d:ipa 15%
AS H Column
Chromatogram
MLU-415 C:\LabSolutions\Data\MLu\MLU-415_AS_85_15-1.lcd
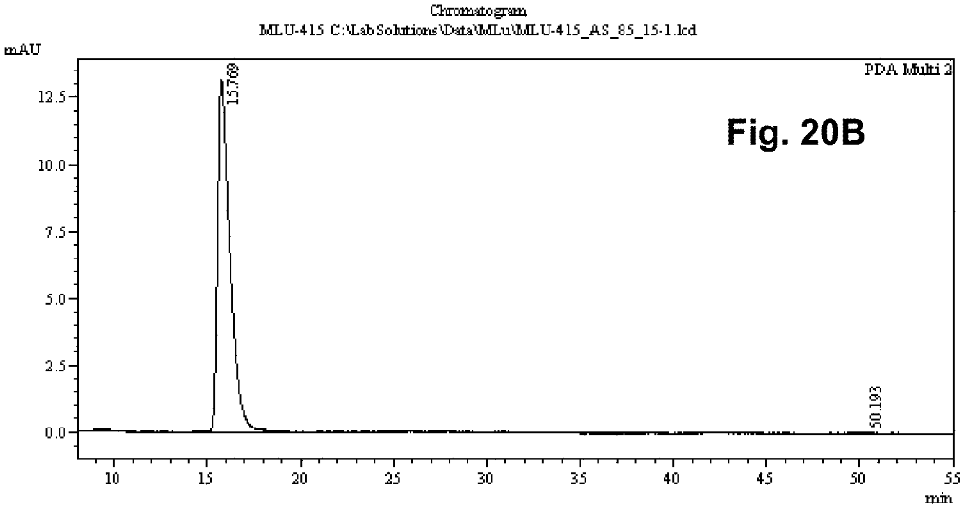
1 PDA Multi 2 / 230nm 4nm
PeakTable
PDA Ch2 230nm 4nm
| Peak# | Ret. Time | Area | Height | Area % | Height % |
|---|---|---|---|---|---|
| 1 | 15.769 | 606606 | 13162 | 99.629 | 99.754 |
| 2 | 50.193 | 2259 | 32 | 0.371 | 0.246 |
| Total | | 608865 | 13194 | 100.000 | 100.000 |

c:hexane 85%
d:ipa 15%
AS H Column
Chromatogram
MLU-360 C:\LabSolutions\Data\MLu\MLU-360_AS_85_15-1.lcd 33c PeakTable PDA Ch3 254nm 4nm

| Peak# | Ret. Time | Area | Height | Area % | Height % |
|---|---|---|---|---|---|
| 1 | 17.641 | 1859638 | 32515 | 50.053 | 73.546 |
| 2 | 45.126 | 1855718 | 11696 | 49.947 | 26.454 |
| Total | | 3715357 | 44211 | 100.000 | 100.000 |

c:hexane 85%
d:ipa 15%
AS H Column
Chromatogram
MLU-356 C:\LabSolutions\Data\MLu\MLU-356_AS_85_15.lcd PeakTable PDA Ch3 254nm 4nm

| Peak# | Ret. Time | Area | Height | Area % | Height % |
|---|---|---|---|---|---|
| 1 | 17.494 | 22437857 | 380475 | 99.241 | 99.711 |
| 2 | 44.910 | 171629 | 1104 | 0.759 | 0.289 |
| Total | | 22609486 | 381579 | 100.000 | 100.000 |

c:hexane 85%
d:ipa 15%
AS H Column

Chromatogram
MLU-378a C:\LabSolutions\Data\MLu\MLU-378a_AS_85_15-1.lcd

33d

PeakTable

PDA Ch2 230nm 4nm

| Peak# | Ret. Time | Area | Height | Area % | Height % |
|---|---|---|---|---|---|
| 1 | 9.650 | 5538157 | 203538 | 50.917 | 70.103 |
| 2 | 17.678 | 5338749 | 86802 | 49.083 | 29.897 |
| Total | | 10876906 | 290339 | 100.000 | 100.000 |

c:hexane 85%
d:ipa 15%
AS H Column

Chromatogram
MLU-372a C:\LabSolutions\Data\MLu\MLU-372a_AS_85_15-1.lcd

PeakTable

PDA Ch2 230nm 4nm

| Peak# | Ret. Time | Area | Height | Area % | Height % |
|---|---|---|---|---|---|
| 1 | 11.043 | 2531259 | 88288 | 99.508 | 99.488 |
| 2 | 20.648 | 12505 | 455 | 0.492 | 0.512 |
| Total | | 2543764 | 88743 | 100.000 | 100.000 |

c:hexane 85%
d:ipa 15%
AS H Column
Chromatogram
MLU-398 C:\LabSolutions\Data\MLu\MLU-398_AS_85_15.lcd
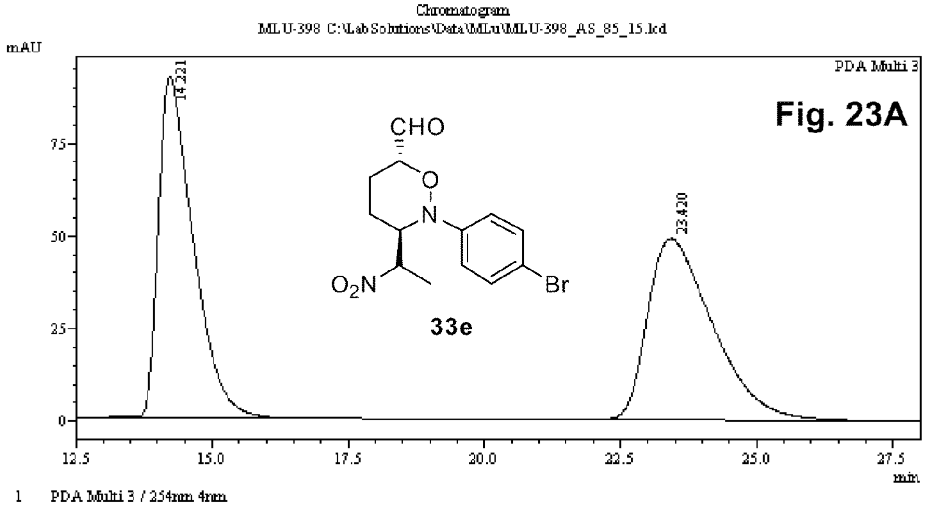
PeakTable
PDA Ch3 254nm 4nm
| Peak# | Ret. Time | Area | Height | Area % | Height % |
|---|---|---|---|---|---|
| 1 | 14.221 | 4130211 | 92296 | 50.529 | 65.382 |
| 2 | 23.420 | 4043769 | 48867 | 49.471 | 34.618 |
| Total | | 8173980 | 141163 | 100.000 | 100.000 |
c:hexane 85%
d:ipa 15%
AS H Column
Chromatogram
MLU-402 C:\LabSolutions\Data\MLu\MLU-402_AS_85_15.lcd
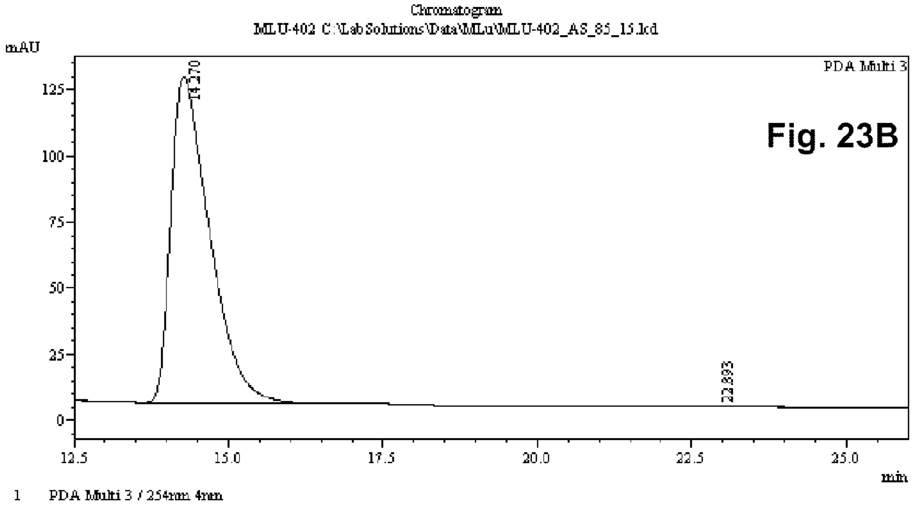
PeakTable
PDA Ch3 254nm 4nm
| Peak# | Ret. Time | Area | Height | Area % | Height % |
|---|---|---|---|---|---|
| 1 | 14.270 | 5379812 | 123308 | 99.488 | 99.683 |
| 2 | 22.893 | 27680 | 392 | 0.512 | 0.317 |
| Total | | 5407492 | 123700 | 100.000 | 100.000 |

c:hexane 85%
d:ipa 15%
AS H Column

Chromatogram
MLU-363a C:\Lab Solutions\Data\MLu\MLU-363a_AS_85_15-1.lcd

33f

PeakTable

PDA Ch2 230nm 4nm

| Peak# | Ret. Time | Area | Height | Area % | Height % |
|---|---|---|---|---|---|
| 1 | 8.906 | 883778 | 24238 | 50.025 | 62.706 |
| 2 | 17.270 | 882877 | 14415 | 49.975 | 37.294 |
| Total | | 1766655 | 38653 | 100.000 | 100.000 |

c:hexane 85%
d:ipa 15%
AS H Column

Chromatogram
MLU-381a C:\Lab Solutions\Data\MLu\MLU-381a_AS_85_15-1.lcd

PeakTable

PDA Ch2 230nm 4nm

| Peak# | Ret. Time | Area | Height | Area % | Height % |
|---|---|---|---|---|---|
| 1 | 8.674 | 18285320 | 894644 | 99.556 | 99.799 |
| 2 | 16.902 | 81469 | 1801 | 0.444 | 0.201 |
| Total | | 18366789 | 896445 | 100.000 | 100.000 |

c:hexane 85%
d:ipa 15%
AS H Column
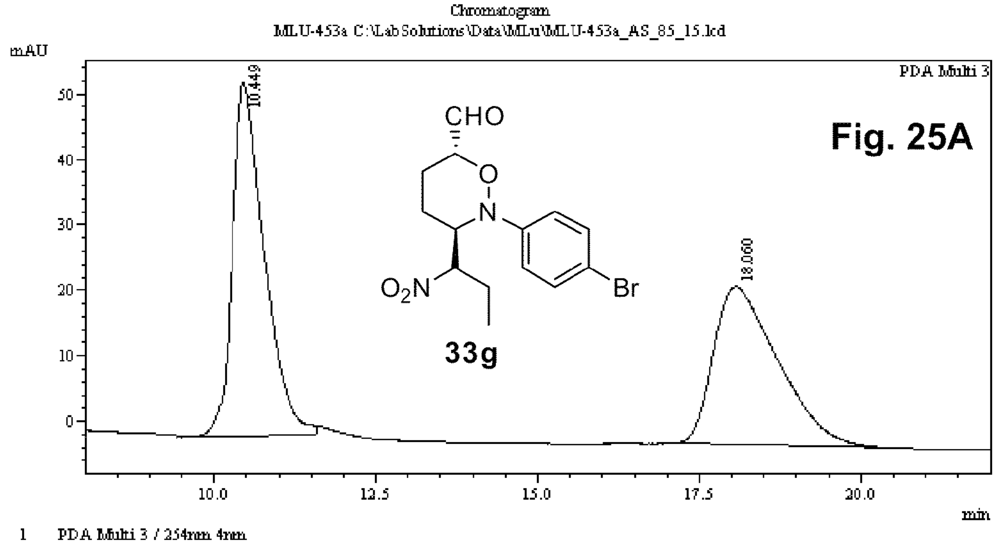
PeakTable
PDA Ch3 254nm 4nm
| Peak# | Ret. Time | Area | Height | Area % | Height % |
|---|---|---|---|---|---|
| 1 | 10.449 | 1817732 | 54044 | 51.874 | 69.130 |
| 2 | 18.060 | 1686373 | 24134 | 48.126 | 30.870 |
| Total | | 3504105 | 78178 | 100.000 | 100.000 |
c:hexane 85%
d:ipa 15%
AS H Column
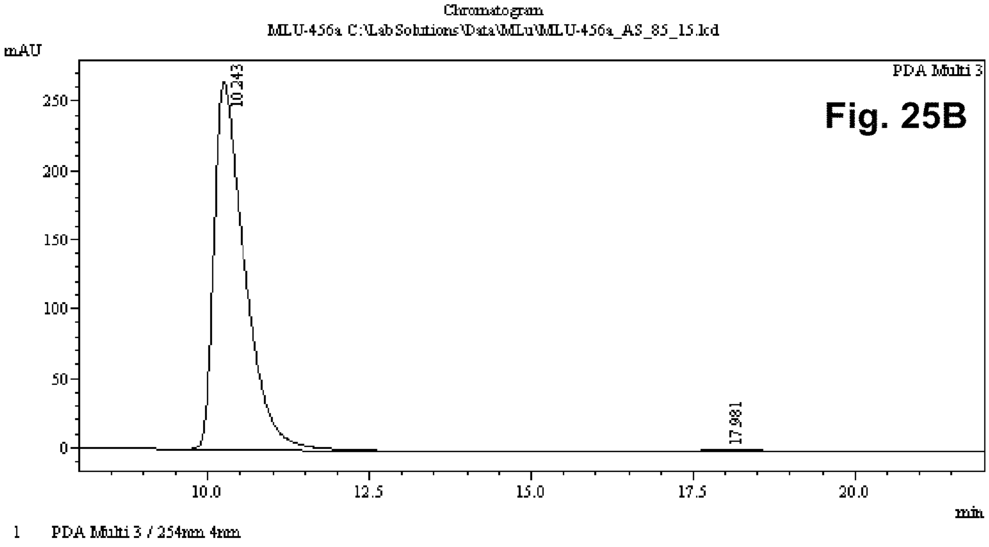
PeakTable
PDA Ch3 254nm 4nm
| Peak# | Ret. Time | Area | Height | Area % | Height % |
|---|---|---|---|---|---|
| 1 | 10.243 | 8735460 | 265352 | 99.546 | 99.618 |
| 2 | 17.981 | 39802 | 1019 | 0.454 | 0.382 |
| Total | | 8775261 | 266370 | 100.000 | 100.000 |

c:hexane 85%
d:ipa 15%
AS H Column

Chromatogram
MLU-395 C:\Lab Solutions\Data\MLu\MLU-395_AS_85_15-1.lcd

33h

PeakTable

PDA Ch1 220nm 4nm

| Peak# | Ret. Time | Area | Height | Area % | Height % |
|---|---|---|---|---|---|
| 1 | 11.919 | 6807384 | 168893 | 99.713 | 99.898 |
| 2 | 30.244 | 19624 | 173 | 0.287 | 0.102 |
| Total | | 6827008 | 169066 | 100.000 | 100.000 |

c:hexane 85%
d:ipa 15%
AS H Column

Chromatogram
MLU-390 C:\Lab Solutions\Data\MLu\MLU-390_AS_85_15.lcd

PeakTable

PDA Ch1 220nm 4nm

| Peak# | Ret. Time | Area | Height | Area % | Height % |
|---|---|---|---|---|---|
| 1 | 11.922 | 9872144 | 223163 | 51.853 | 78.236 |
| 2 | 29.820 | 9166528 | 62081 | 48.147 | 21.764 |
| Total | | 19038671 | 285245 | 100.000 | 100.000 |

CHO
O
N
$O_2N$
Br
Ph
33j
ppm 202.04
147.55
134.86
132.42
128.88
128.53
127.61
115.99
115.14
88.51
83.30
60.40
38.49
22.41
18.99
CHO
O
N
$O_2N$
Br
Ph
33j ppm c:hexane 85%
d:ipa 15%
AS H Column
Chromatogram
MLU-472b C:\LabSolutions\Data\MLu\MLU-472b_AS_85_15.lcd
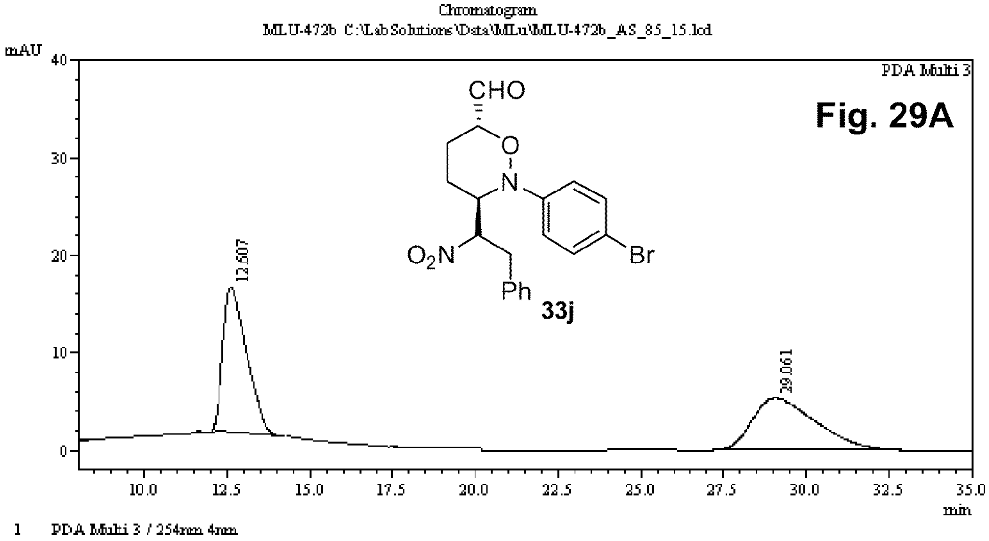
PeakTable
PDA Ch3 254nm 4nm
| Peak# | Ret. Time | Area | Height | Area % | Height % |
|---|---|---|---|---|---|
| 1 | 12.607 | 707938 | 14708 | 50.195 | 73.404 |
| 2 | 29.061 | 702442 | 5329 | 49.805 | 26.596 |
| Total | | 1410380 | 20037 | 100.000 | 100.000 |
c:hexane 85%
d:ipa 15%
AS H Column
Chromatogram
MLU-433a C:\LabSolutions\Data\MLu\MLU-433a_AS_85_15.lcd
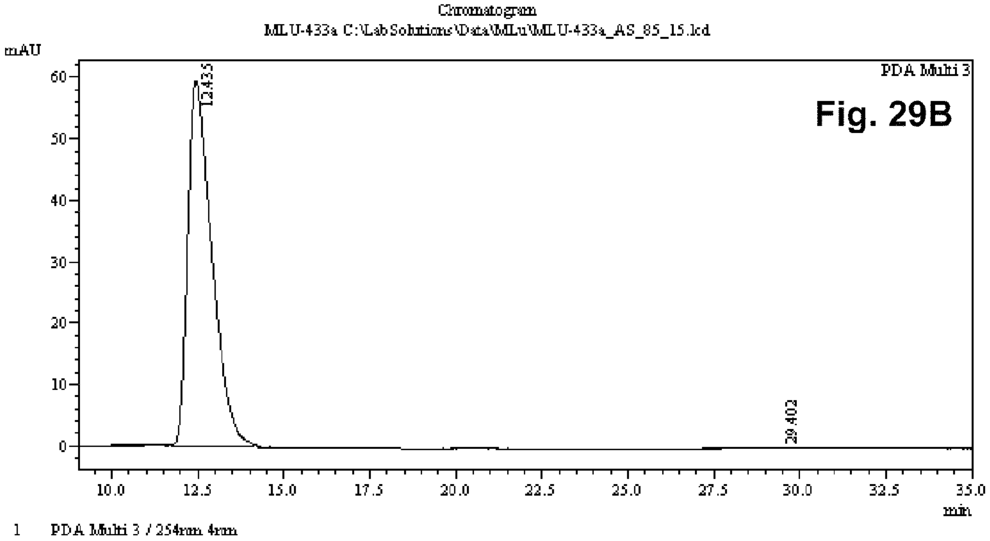
PeakTable
PDA Ch3 254nm 4nm
| Peak# | Ret. Time | Area | Height | Area % | Height % |
|---|---|---|---|---|---|
| 1 | 12.435 | 2919273 | 59529 | 99.427 | 99.770 |
| 2 | 29.402 | 16825 | 137 | 0.573 | 0.230 |
| Total | | 2936098 | 59666 | 100.000 | 100.000 |

c:hexane 85%
d:ipa 15%
AS H Column

Chromatogram
MLU-407a C:\LabSolutions\Data\MLu\MLU-407a_AS_85_15-2.lcd

1 PDA Multi 1 / 220nm 4nm

PeakTable

PDA Ch1 220nm 4nm

| Peak# | Ret. Time | Area | Height | Area % | Height % |
|---|---|---|---|---|---|
| 1 | 9.268 | 11213765 | 375188 | 50.730 | 78.028 |
| 2 | 26.417 | 10890871 | 105648 | 49.270 | 21.972 |
| Total | | 22104636 | 480836 | 100.000 | 100.000 |

c:hexane 85%
d:ipa 15%
AS H Column

Chromatogram
MLU-412a C:\LabSolutions\Data\MLu\MLU-412a_AS_85_15-2.lcd

1 PDA Multi 1 / 220nm 4nm

PeakTable

PDA Ch1 220nm 4nm

| Peak# | Ret. Time | Area | Height | Area % | Height % |
|---|---|---|---|---|---|
| 1 | 10.224 | 3723625 | 106382 | 99.711 | 99.875 |
| 2 | 30.725 | 10788 | 133 | 0.289 | 0.125 |
| Total | | 3734414 | 106516 | 100.000 | 100.000 |

c:hexane 85%
d:ipa 15%
AS H Column
Chromatogram
MLU-446a C:\LabSolutions\Data\MLu\MLU-446a_AS_85_15.lcd
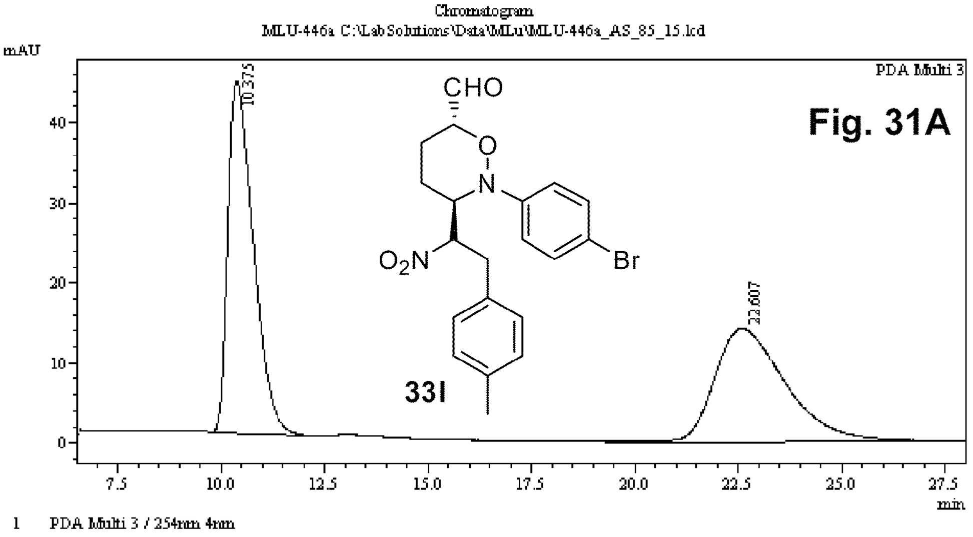
PeakTable
PDA Ch3 254nm 4nm
| Peak# | Ret. Time | Area | Height | Area % | Height % |
|---|---|---|---|---|---|
| 1 | 10.375 | 1893131 | 44075 | 52.713 | 75.722 |
| 2 | 22.607 | 1698264 | 14131 | 47.287 | 24.278 |
| Total | | 3591395 | 58207 | 100.000 | 100.000 |
c:hexane 85%
d:ipa 15%
AS H Column
Chromatogram
MLU-449a C:\LabSolutions\Data\MLu\MLU-449a_AS_85_15.lcd
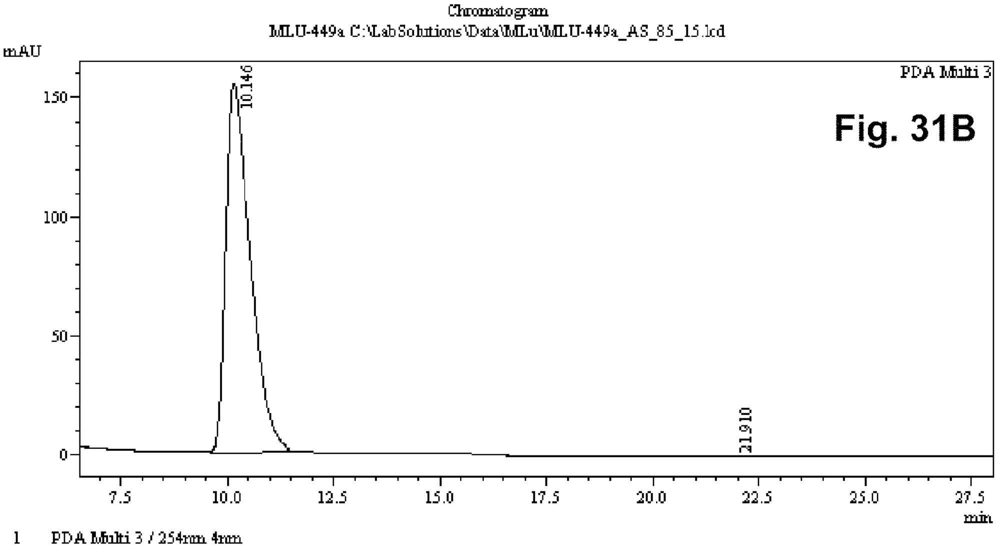
PeakTable
PDA Ch3 254nm 4nm
| Peak# | Ret. Time | Area | Height | Area % | Height % |
|---|---|---|---|---|---|
| 1 | 10.146 | 6325736 | 154971 | 99.662 | 99.750 |
| 2 | 21.910 | 21478 | 388 | 0.338 | 0.250 |
| Total | | 6347214 | 155359 | 100.000 | 100.000 |

c:hexane 85%
d:ipa 15%
AS H Column

Chromatogram
MLU-305a C:\LabSolutions\Data\MLu\MLU-305a_AS_85_15.lcd

33m

PeakTable

PDA Ch1 220nm 4nm

| Peak# | Ret. Time | Area | Height | Area % | Height % |
|---|---|---|---|---|---|
| 1 | 11.923 | 3217706 | 81359 | 50.605 | 82.763 |
| 2 | 44.912 | 3140809 | 16945 | 49.395 | 17.237 |
| Total | | 6358515 | 98304 | 100.000 | 100.000 |

c:hexane 85%
d:ipa 15%
AS H Column

Chromatogram
MLU-391a C:\LabSolutions\Data\MLu\MLU-391a_AS_85_15.lcd

PeakTable

PDA Ch1 220nm 4nm

| Peak# | Ret. Time | Area | Height | Area % | Height % |
|---|---|---|---|---|---|
| 1 | 12.307 | 23458158 | 469677 | 99.630 | 99.903 |
| 2 | 48.194 | 87235 | 454 | 0.370 | 0.097 |
| Total | | 23545394 | 470131 | 100.000 | 100.000 |

c:hexane 85%
d:ipa 15%
AS H Column

33n

PeakTable

PDA Ch3 254nm 4nm

| Peak# | Ret. Time | Area | Height | Area % | Height % |
|---|---|---|---|---|---|
| 1 | 14.108 | 758171 | 12150 | 51.131 | 78.908 |
| 2 | 32.078 | 724642 | 3248 | 48.869 | 21.092 |
| Total | | 1482814 | 15397 | 100.000 | 100.000 |

c:hexane 85%
d:ipa 15%
AS H Column

PeakTable

PDA Ch3 254nm 4nm

| Peak# | Ret. Time | Area | Height | Area % | Height % |
|---|---|---|---|---|---|
| 1 | 14.573 | 6392036 | 102185 | 99.888 | 99.717 |
| 2 | 34.199 | 7175 | 290 | 0.112 | 0.283 |
| Total | | 6399211 | 102475 | 100.000 | 100.000 |

c:hexane 85%
d:ipa 15%
AS H Column

Chromatogram
HYX-074a C:\LabSolutions\Data\MLu\HYX-074a_AS_85_15.lcd

33o

PeakTable

PDA Ch1 220nm 4nm

| Peak# | Ret. Time | Area | Height | Area % | Height % |
|---|---|---|---|---|---|
| 1 | 12.941 | 737281 | 15516 | 49.492 | 83.055 |
| 2 | 46.972 | 752416 | 3166 | 50.508 | 16.945 |
| Total | | 1489697 | 18682 | 100.000 | 100.000 |

c:hexane 85%
d:ipa 15%
AS H Column

Chromatogram
HYX-072b C:\LabSolutions\Data\MLu\HYX-072a_AS_85_15.lcd

PeakTable

PDA Ch1 220nm 4nm

| Peak# | Ret. Time | Area | Height | Area % | Height % |
|---|---|---|---|---|---|
| 1 | 13.337 | 5870550 | 115574 | 99.729 | 99.906 |
| 2 | 49.114 | 15944 | 109 | 0.271 | 0.094 |
| Total | | 5886494 | 115683 | 100.000 | 100.000 |

c:hexane 85%
d:ipa 15%
AS H Column
Chromatogram
MLU-465a C:\LabSolutions\Data\MLu\MLU-465a_AS_85_15.lcd 33p PeakTable PDA Ch1 220nm 4nm

| Peak# | Ret. Time | Area | Height | Area % | Height % |
|---|---|---|---|---|---|
| 1 | 14.877 | 1771841 | 29252 | 50.708 | 74.736 |
| 2 | 31.953 | 1722363 | 9888 | 49.292 | 25.264 |
| Total | | 3494204 | 39140 | 100.000 | 100.000 |

c:hexane 85%
d:ipa 15%
AS H Column
Chromatogram
MLU-463a C:\LabSolutions\Data\MLu\MLU-463a_AS_85_15.lcd PeakTable PDA Ch1 220nm 4nm

| Peak# | Ret. Time | Area | Height | Area % | Height % |
|---|---|---|---|---|---|
| 1 | 15.069 | 2887197 | 44767 | 99.490 | 99.723 |
| 2 | 32.700 | 14797 | 124 | 0.510 | 0.277 |
| Total | | 2901994 | 44892 | 100.000 | 100.000 |

MLu-668
c:hexane 85%
d:ipa 15%
AS H Column

Chromatogram
MLu-668 C:\LabSolutions\Data\MLu\MLU-668_AS_85_15.lcd

33q

PeakTable

PDA Ch2 230nm 4nm

| Peak# | Ret. Time | Area | Height | Area % | Height % |
|---|---|---|---|---|---|
| 1 | 13.661 | 8423018 | 197119 | 50.268 | 76.121 |
| 2 | 34.143 | 8333126 | 61835 | 49.732 | 23.879 |
| Total | | 16756144 | 258954 | 100.000 | 100.000 |

MLu-664
c:hexane 85%
d:ipa 15%
AS H Column

Chromatogram
MLu-664 C:\LabSolutions\Data\MLu\MLU-664_AS_85_15-2.lcd

PeakTable

PDA Ch2 230nm 4nm

| Peak# | Ret. Time | Area | Height | Area % | Height % |
|---|---|---|---|---|---|
| 1 | 13.439 | 7548481 | 179028 | 99.839 | 99.883 |
| 2 | 33.845 | 12149 | 210 | 0.161 | 0.117 |
| Total | | 7560630 | 179238 | 100.000 | 100.000 |

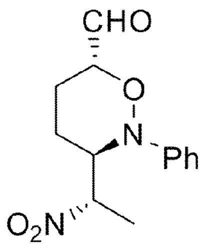
33d
Fig. 37
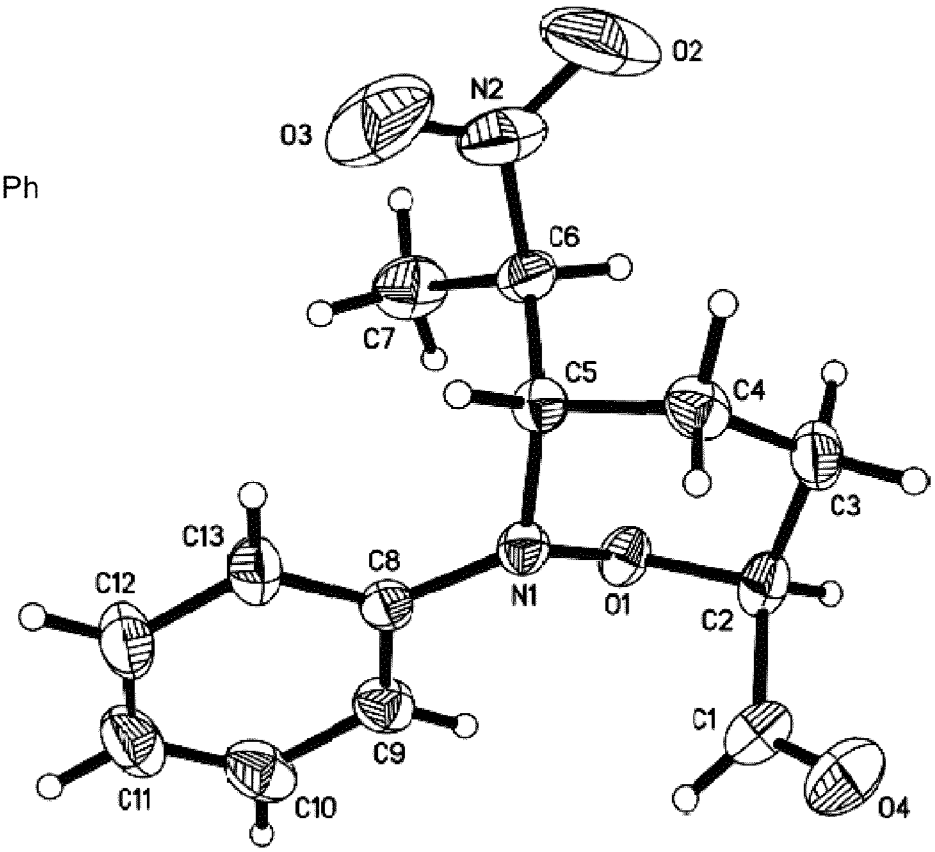
The crystal data deposition number of 33d: CCDC 670447 zd045-2
c:hexane 95%
d:ipa 5%
AS-H Column
1 mL/min

PeakTable

PDA Ch3 254nm 4nm

| Peak# | Ret. Time | Area | Height | Area % | Height % |
|---|---|---|---|---|---|
| 1 | 13.219 | 210947 | 4386 | 49.912 | 57.631 |
| 2 | 17.486 | 211694 | 3225 | 50.088 | 42.369 |
| Total | | 422641 | 7611 | 100.000 | 100.000 |

zd046-2
c:hexane 95%
d:ipa 5%
AS-H Column
1 mL\min

PeakTable

PDA Ch3 254nm 4nm

| Peak# | Ret. Time | Area | Height | Area % | Height % |
|---|---|---|---|---|---|
| 1 | 12.993 | 8488315 | 181258 | 99.098 | 99.302 |
| 2 | 17.325 | 77239 | 1274 | 0.902 | 0.698 |
| Total | | 8565554 | 182532 | 100.000 | 100.000 |

zd140
c:hexane 99%
d:ipa 1%
AS-H Column
1 mL\min

Chromatogram
zd140 C:\LabSolutions\Data\ZD\zd140 ash 99hexane 1ml per min 254nm.lcd 23b-rac PeakTable PDA Ch3 254nm 4nm

| Peak# | Ret. Time | Area | Height | Area % | Height % |
|---|---|---|---|---|---|
| 1 | 16.243 | 4255279 | 55198 | 48.837 | 52.294 |
| 2 | 19.257 | 4458036 | 50356 | 51.163 | 47.706 |
| Total | | 8713315 | 105554 | 100.000 | 100.000 |

zd069-2
c:hexane 99%
d:ipa 1%
AS-H Column
1 mL\min

23b

PeakTable

PDA Ch3 254nm 4nm

| Peak# | Ret. Time | Area | Height | Area % | Height % |
|---|---|---|---|---|---|
| 1 | 17.021 | 1453698 | 19358 | 3.025 | 3.977 |
| 2 | 19.416 | 46605040 | 467420 | 96.975 | 96.023 |
| Total | | 48058738 | 486778 | 100.000 | 100.000 |

PROCESSES OF ENANTIOSELECTIVELY FORMING AN AMINOXY COMPOUND AND AN 1,2-OXAZINE COMPOUND

CROSS-REFERENCE TO RELATED APPLICATIONS

This application makes reference to and claims the benefit of priority of an application for "Organocatalytic Enantioselective α-Aminoxylation of Aldehydes and its Application for the Synthesis of Chiral 1,2-Diols, and α-Aminoxylation/Aza-Michael Reactions for the Synthesis of Functionalized Tetrahydro-1,2-Oxazines" filed on May 21, 2009 with the United States Patent and Trademark Office, and there duly assigned Ser. No. 61/180,353. This application further makes reference to and claims the benefit of priority of an application for "Processes Of Enantioselectively Forming An Aminoxy Compound And An 1,2-Oxazine Compound" filed on Sep. 10, 2009 with the United States Patent and Trademark Office, and there duly assigned Ser. No. 61/241,157. The contents of said applications filed on May 21, 2009 and Sep. 10, 2009 are incorporated herein by reference for all purposes in their entirety.

FIELD OF THE INVENTION

The present invention provides a process of enantioselectively forming an aminoxy compound and an 1,2-oxazine compound.

BACKGROUND OF THE INVENTION

The presence of optically active α-hydroxylcarbonyl moieties as well as 1,2-diols in many biologically active natural products motivated numerous research into finding new routes to provide better stereocontrol for these synthetically useful synthons. Asymmetric α-hydroxylation of enolates and the Sharpless asymmetric dihydroxylation of olefins are some methods to synthesize these compounds. The year 2000 saw a renaissance of organocatalysis, and since then organocatalysis has emerged as an extremely useful tool for the preparation of enantiomerically pure compounds. Operational simplicity, availability and the non-toxicity of the organic catalysts compared to the corresponding transition-metal species, as well as its high efficiencies and selectivities attained in many organocatalytic transformations made this methodology very attractive for the formation of enantiomerically pure compounds.

In 2003, Zhong (Angew. Chem., Int. Ed. (2003) 42, 4247), MacMillan (S. P. Brown et al., J. Am. Chem. Soc. (2003) 125, 10808) and Hayashi (Y. Hayashi et al., Tetrahedron Lett. (2003) 44, 8293) independently reported the direct proline-catalyzed α-aminoxylation of aldehydes with nitrosobenzene and the usefulness of this reaction was demonstrated in the synthesis of several biologically active compounds (S. P. Kotkar et al., Tetrahedron: Asymmetry (2007) 18, 1795; S. P. Kotkar et al., Tetrahedron: Asymmetry (2007) 18, 1738; S. P. Kotkar & A. Sudalai, Tetrahedron Lett. (2006) 47, 6813; S. V. Narina & A. Sudalai, Tetrahedron Lett. (2006) 47, 6799; S. G. Kim & T. H. Park, Tetrahedron Lett. (2006) 47, 6369; Sousuke Hara et al., Tetrahedron Lett. (2006) 47, 1081; I. K. Mangion & D. W. C. MacMillan, J. Am. Chem. Soc. (2005) 127, 3696). Though the scope of the abovementioned reaction has been quickly extended to that of ketones (Y. Hayashi et al., Angew. Chem., Int. Ed. (2004) 43, 1112; A. Bøgevig et al., Angew. Chem., Int. Ed, (2004) 43, 1109) after the first report, there was little development in new organocatalysts (T. Kano et al., Chem. Lett. (2008) 37, 250; Y. Hayashi, et al., Adv. Synth. Catal. (2004) 346, 1435; H. Sundén et al., Tetrahedron Lett. (2005) 46, 3385; W. Wang et al., Tetrahedron Lett. (2004) 45, 7235; N. Momiyama et al., Proc. Natl. Acad. Sci. USA (2004) 101, 5374) or environmentally friendly reaction protocols (D. Font et al., Org. Lett. (2007) 9, 1943; H.-M. Guo et al., Green Chem. (2006) 8, 682).

Recently, demand has increased for innovative and imaginative synthetic methodologies to improve efficiency and sustainability such as simplicity, atom economy, reduced chemical wastage and energy usage, safety, and environment friendliness.

Accordingly, it is a further object of the present invention to provide a synthesis route to α-hydroxycarbonyl- and/or 1,2-dihydroxy compounds under conditions that are a lower burden to the environment than currently available methods.

Tetrahydro-1,2-oxazine derivatives occur frequently in biologically active compounds (Uchida, I., et al., J. Am. Chem. Soc. (1987) 109, 4108; Terano, H.; et al., J. Antibiot. (1989) 42, 145; Yu, Q.-S, et al., J. Med. Chem. (2002) 45, 3684; Katoh, T., et al., Tetrahedron (1997) 53, 10229; Judd, T. C., & Williams, R. M., Angew. Chem., Int. Ed. (2002) 41, 4683; Suzuki, M., et al., Angew. Chem. Int. Ed. (2002) 41, 4686) and are valuable synthetic intermediates (Pulz, R., et al., Org. Lett. (2002) 4, 2353; Tishkov, A. A., et al., Synlett (2002) 863; Buchholz, M.; Reissig, H.-U. Eur. J. Org. Chem. (2003) 3524; Al-Harrasi, A., & Reissig, H.-U., Angew. Chem. Int. Ed. (2005) 44, 6227; Carson, C. A., & Kerr, M. A., Angew. Chem. Int. Ed. (2006) 45, 6560). Not only do they have the potential to act as therapeutic agents and chiral building blocks, they also possess synthetic utility through reductive N—O bond cleavage to form highly functionalized 1,4-amino alcohols which can be found in a number of bioactive natural products.

The nitroso function is recognized as a unique source to prepare nitrogen- and oxygen-containing molecules. Various catalytic asymmetric reactions exploiting the unique properties of nitroso compounds (Palomo, C., et al., Angew. Chem. Int. Ed. (2007) 46, 8054), such as aminoxylation, oxyamination, and nitroso Diels-Alder reactions, have recently been developed. Nevertheless, only two general routes for tetrahydro-1,2-oxazines have so far been used including the addition of nitrones to activated cyclopropanes (M. P. Sibi, et al., J. Am. Chem. Soc. (2005) 127, 5764-5765) and the sequential nitroso aldol/Michael addition of cyclic enones reported by Yamamoto et al. (Yamamoto, Y, et al., J. Am. Chem. Soc. (2004) 126, 5962-5963; Momiyama, N, et al., J. Am. Chem. Soc. (2007) 129, 1190-1195). The substrate scope for these two examples is limited, and the development of a practical, asymmetric synthetic procedure to access enantiopure functionalized tetrahydro-1,2-oxazines from acyclic starting materials is highly desirable.

Accordingly, it is a further object of the present invention to provide a process that allows a simple formation of tetrahydro-1,2-oxazine compounds with potentially high enantio- and diastereoselectivity.

SUMMARY OF THE INVENTION

In a first aspect the invention relates to a process of enantioselectively forming an aminoxy compound of Formula (3)

(3)

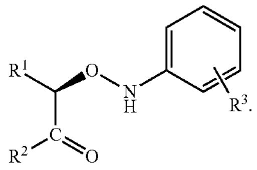

In formula (3) $R^1$ is one of an aliphatic group, an alicyclic group, an aromatic group, an arylaliphatic group and an arylalicyclic group. The respective aliphatic, alicyclic, aromatic, arylaliphatic or arylalicyclic group includes 0 to about 3 heteroatoms independently selected from the group consisting of N, O, S, Se and Si. $R^2$ is one of hydrogen, an aliphatic group and an alicyclic group. The respective aliphatic or alicyclic group includes 0 to about 3 heteroatoms independently selected from the group consisting of N, O, S, Se and Si. In some embodiments one of $R^1$ and $R^2$ defines an aliphatic, aromatic or arylaliphatic bridge that is linked to the respective other moiety of $R^2$ and $R^1$. Accordingly, $R^1$ and $R^2$ may in some embodiments define one common cyclic structure. $R^3$ is one of hydrogen, halogen, hydroxyl and an aliphatic group with a main chain having 1 to about 10 carbon atoms. The process includes contacting a carbonyl compound of Formula (1)

(1)

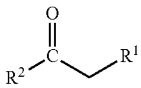

and a nitroso compound of Formula (2)

(2)

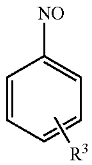

in the presence of a chiral catalyst. The moieties $R^1$, $R^2$ and $R^3$ in these formulas are as defined above. The chiral catalyst is a compound of Formula (IX)

(IX)

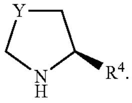

In this formula (IX) $R^4$ is one of COOH and

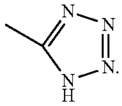

Y in formula (IX) is one of CHOH, O, S, Se, $CH_2$, CHOH, CHSH and CHSeH. The reaction of the process is carried out in an aqueous solution in the presence of a phase transfer catalyst.

In a further aspect the invention provides a process of enantioselectively forming an aminoxy compound of Formula (4)

(4)

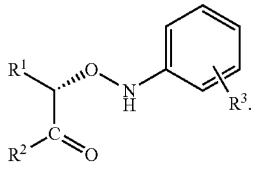

In formula (4) $R^1$ is one of an aliphatic group, an alicyclic group, an aromatic group, an arylaliphatic group and an arylalicyclic group. The respective aliphatic, alicyclic, aromatic, arylaliphatic or arylalicyclic group includes 0 to about 3 heteroatoms independently selected from the group consisting of N, O, S, Se and Si. $R^2$ in formula (4) is one of hydrogen, an aliphatic group and an alicyclic group. The respective aliphatic or alicyclic, group includes 0 to about 3 heteroatoms independently selected from the group consisting of N, O, S, Se and Si. In some embodiments one of $R^1$ and $R^2$ define an aliphatic or arylaliphatic bridge that is linked to the respective other moiety of $R^2$ and $R^1$. Accordingly, $R^1$ and $R^2$ may in some embodiments define one common cyclic structure. $R^3$ is one of hydrogen, halogen, hydroxyl and an aliphatic group with a main chain having 1 to about 10 carbon atoms. The process includes contacting a carbonyl compound of Formula (1)

(1)

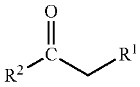

and a nitroso compound of Formula (2)

(2)

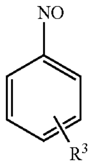

in the presence of a chiral catalyst. The moieties $R^1$, $R^2$ and $R^3$ in these formulas are as defined above. The chiral catalyst is a compound of Formula (V)

(V)

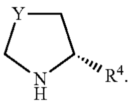

In this formula (V) $R^4$ is one of COOH and

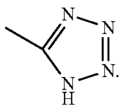

Y in formula (V) is one of CHOH, O, S, Se, $CH_2$, CHOH, CHSH and CHSeH. The reaction of the process is carried out in an aqueous solution in the presence of a phase transfer catalyst.

In yet a further aspect the invention provides a process of enantioselectively forming an 1,2-oxazine compound of Formula (13)

(13)

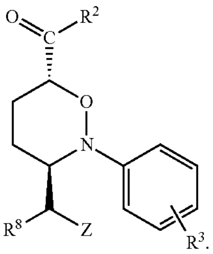

In Formula (XIII) $R^2$ is one of hydrogen, an aliphatic group and an alicyclic group. The respective aliphatic or alicyclic, group includes 0 to about 3 heteroatoms independently selected from the group consisting of N, O, S, Se and Si. $R^3$ is one of hydrogen, halogen, $OR^6$, an aliphatic group with a main chain having 1 to about 10 carbon atoms. In Formula (13) $R^8$ is one of hydrogen, $NO_2$, CN, $C(R^{40})O$, $COOR^{40}$, and $CONR^{40}R^{41}$, an aliphatic group, an alicyclic group, an aromatic group, an arylaliphatic group and an arylalicyclic group. The respective aliphatic, alicyclic, aromatic, arylaliphatic or arylalicyclic group includes 0 to about 3 heteroatoms independently selected from the group consisting of N, O, S, Se and Si. Moieties $R^{40}$ and $R^{41}$ are independent from one another one of hydrogen, an aliphatic group, an alicyclic group, an aromatic group, an arylaliphatic group and an arylalicyclic group. The respective aliphatic, alicyclic, aromatic, arylaliphatic or arylalicyclic group includes 0 to about 3 heteroatoms independently selected from the group consisting of N, O, S, Se and Si. In Formula (13) Z is one of $NO_2$, CN, $C(R^{42})O$, $COOR^{42}$, and $CONR^{42}R^{43}$. Moieties $R^{42}$ and $R^{43}$ are independent from one another one of hydrogen, an aliphatic group, an alicyclic group, an aromatic group, an arylaliphatic group and an arylalicyclic group. The respective aliphatic, alicyclic, aromatic, arylaliphatic or arylalicyclic group includes 0 to about 3 heteroatoms independently selected from the group consisting of N, O, S, Se and Si. The process includes contacting a carbonyl compound of Formula (11)

(11)

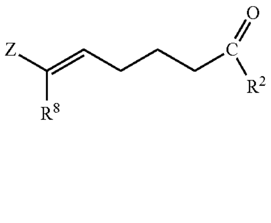

and a nitroso compound of Formula (2)

(2)

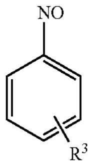

in the presence of a chiral catalyst. The moieties $R^2$, $R^3$ and $R^8$ in these formulas are as defined above. The chiral catalyst is a compound of Formula (IX)

(IX)

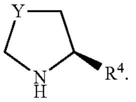

In this formula (IX) $R^4$ is one of COOH and

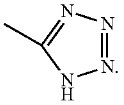

Y in formula (IX) is one of CHOH, O, S, Se, $CH_2$, CHOH, CHSH and CHSeH. By contacting carbonyl compound and the nitroso compound in the presence of the chiral catalyst a reaction mixture is formed. The carbonyl compound of Formula (1) and the nitroso compound of Formula (2) are allowed to react in the reaction mixture. Thereby the formation of the 1,2-oxazine compound of Formula (13) is allowed to occur.

BRIEF DESCRIPTION OF THE DRAWINGS

The invention will be better understood with reference to the detailed description when considered in conjunction with the non-limiting examples and the accompanying drawings.

FIG. 4 illustrates the catalyst screening in the reaction between a carbonyl compound of formula 1a and a nitroso compound of formula 2a in the formation of an aminoxy compound of formula 9a. Conditions: Nitrosobenzene (0.3 mmol), propanal (3 equiv), catalyst (30 mol %), tetra-butylammonium bromide (2 equiv) and water (0.10 mL) were added at 0° C. and then warmed to rt (23° C.) unless otherwise stated. a: Isolated yields. b: Determined by chiral phase HPLC.

FIG. 6 illustrates the generality of reaction of α-aminoxylation in the presence of water. Conditions: Nitrosobenzene (0.3 mmol), propanal (3 equiv), catalyst (20 mol %), tetrabutylammonium bromide (2 equiv) and water (0.10 mL) was added at 0° C. and stirred at rt (23° C.) unless otherwise stated. a: Isolated yields. b: Determined by chiral phase HPLC. c: Nitrosotoluene was used instead of nitrosobenzene.

FIG. 7A depicts further examples of catalysts the use of which is contemplated. $R^1$, $R^{1'}$ and $R^{1''}$ are independently selected moieties as defined for $R^1$ in the description. In (1×g) and (IXh) n is an integer from 1 to about 20.

FIG. 8 illustrates the screening of reaction conditions of an organocatalytic domino α-aminoxylation/aza-Michael reaction of the invention yielding an aminoxy compound 33a. Reaction conditions: 2a (1.0 equiv; 1 M), 31a (1.5 equiv), and catalyst IX at room temperature (23° C.) in the indicated solvent. a: Yield of isolated product. b: Determined by chiral HPLC analysis. c: Determined by $^1H$ NMR methods. d: Used 3 equiv of 31a. e: Reaction was conducted at 0° C. f: Reaction was conducted at −20° C. g: 0.1 M of 2a. h: Added 1.0 equiv of TEAB. i: In situ reduction was performed using $NaBH_4$ to provide the corresponding alcohol. n.d.=not determined.

FIG. 12A illustrates the DFT-calculated lowest energy transition state for the aza-Michael addition/protonation in $CH_3CN$ (see also the examples below). FIG. 12B depicts schematically the transition state as confirmed by DF calculations.

FIG. 13 depicts a catalyst and Solvent Screening in a tandem aminoxylation/aza-Michael reaction using an aldehyde 21a with a dicarboxyl moiety as the carbonyl compound. In all cases, 0.2 equiv of catalyst was used in 0.1 M of nitrosobenzene solution. a: Isolated yields. b: Ee and dr determined by HPLC employing a Daicel Chiracel AS-H column. c: 2 equiv of PTC added, PTC) tetraethylammonium bromide.

FIG. 14 illustrates identified optimized conditions for the tandem aminoxylation/aza-Michael reaction. Conditions: nitrosobenzene (0.1 mmol) was added to the solution of aldehyde and catalyst in 1 mL of $CH_3CN$ at −78° C., then stirred at various temperatures. a: Equiv is mol ratio of aldehyde/nitrosobenzene. b: Catalyst loading=proline/nitrobenzene. c: Isolated yields. d: Ee and dr determined by HPLC employing a Daicel Chiracel AS-H column. e: Reduction in situ was performed to provide the corresponding alcohol. Dr was determined by $^1H$ NMR.

FIG. 15 depicts the synthesis of hydrazine derivative 50i, to analyse the stereochemistry of the tandem aminoxylation/aza-Michael reaction.

FIG. 17 depicts the X-ray crystal structure of 50i.

FIG. 20 depicts a HPLC spectrum of a racemic mixture of compound 33a (A) in comparison to the obtained product 33a (B).

FIG. 23 depicts a HPLC spectrum of a racemic mixture of compound 33e (A) in comparison to the obtained product 33e (B).

FIG. 25 depicts a HPLC spectrum of a racemic mixture of compound 33g (A) in comparison to the obtained product 33g (B).

FIG. 29 depicts a HPLC spectrum of a racemic mixture of compound 33j (A) in comparison to the obtained product 33j (B).

FIG. 31 depicts a HPLC spectrum of a racemic mixture of compound 331 (A) in comparison to the obtained product 331 (B).

FIG. 37 a representation of the crystal data of compound 33d (deposition number: CCDC 670447)

FIG. 38 depicts an HPLC spectrum of a racemic mixture of compound 23a.

FIG. 39 depicts an HPLC spectrum of obtained compound 23a.

DETAILED DESCRIPTION OF THE INVENTION

Figure 1A:
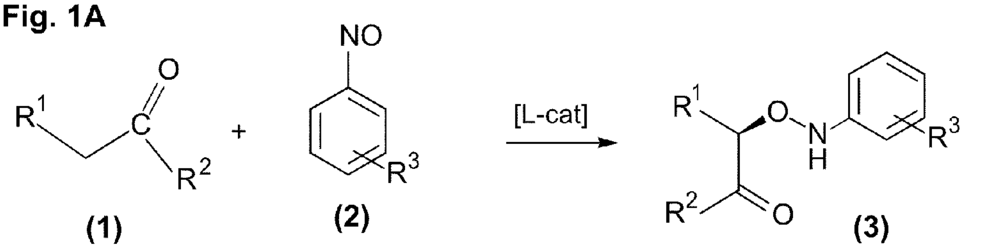
FIG. 1A illustrates the reaction of a carbonyl compound of Formula (1) with a nitroso compound of Formula (2) in the formation of an aminoxy compound of Formula (3). The reaction is catalysed by a chiral compound in the L form.
Figure 1B:
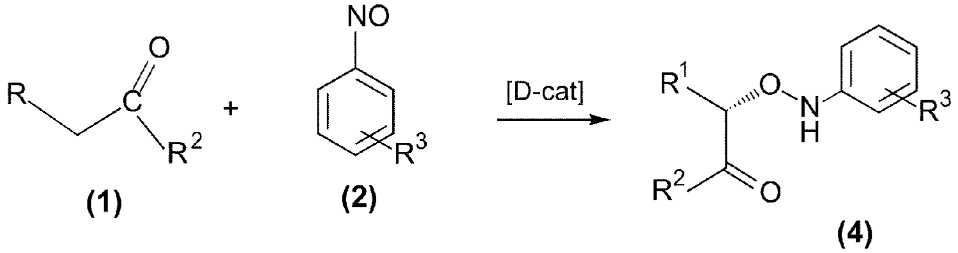
FIG. 1B illustrates the reaction of a carbonyl compound of Formula (1) with a nitroso compound of Formula (2) in the formation of an aminoxy compound of Formula (4). The reaction is catalysed by a chiral compound in the D form.
Figure 2A:
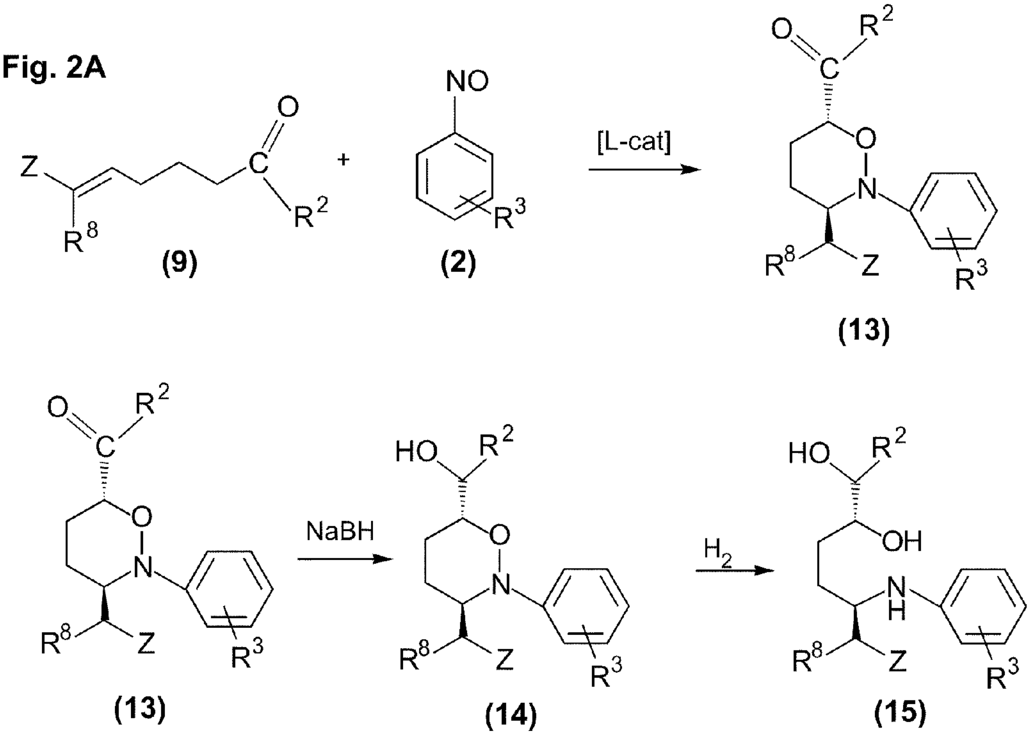
FIG. 2A illustrates a process that includes as a first step the reaction of a carbonyl compound of Formula (11) with a nitroso compound of Formula (2) in the formation of an 1,2-oxazine compound of Formula (13). The reaction is catalysed by a chiral compound in the L form. The depicted process includes a further step in which the carbonyl group of the 1,2-oxazine compound of Formula (13) is reduced, thereby forming 1,2-oxazine compound (14). If desired the 1,2-oxazine compound may be cleaved to yield an amine (15), which is a 1,2-diol.
Figure 2B:
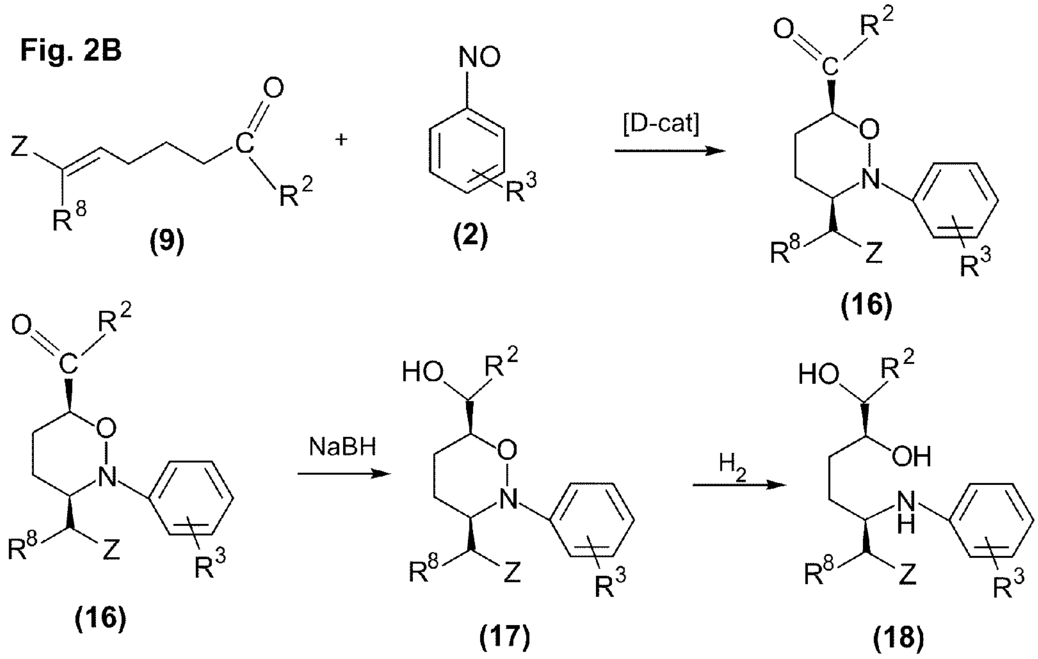
FIG. 2B illustrates the corresponding process where in the first step a chiral compound in the D form is used, resulting the formation of an 1,2-oxazine compound of Formula (16).
Figure 3A:
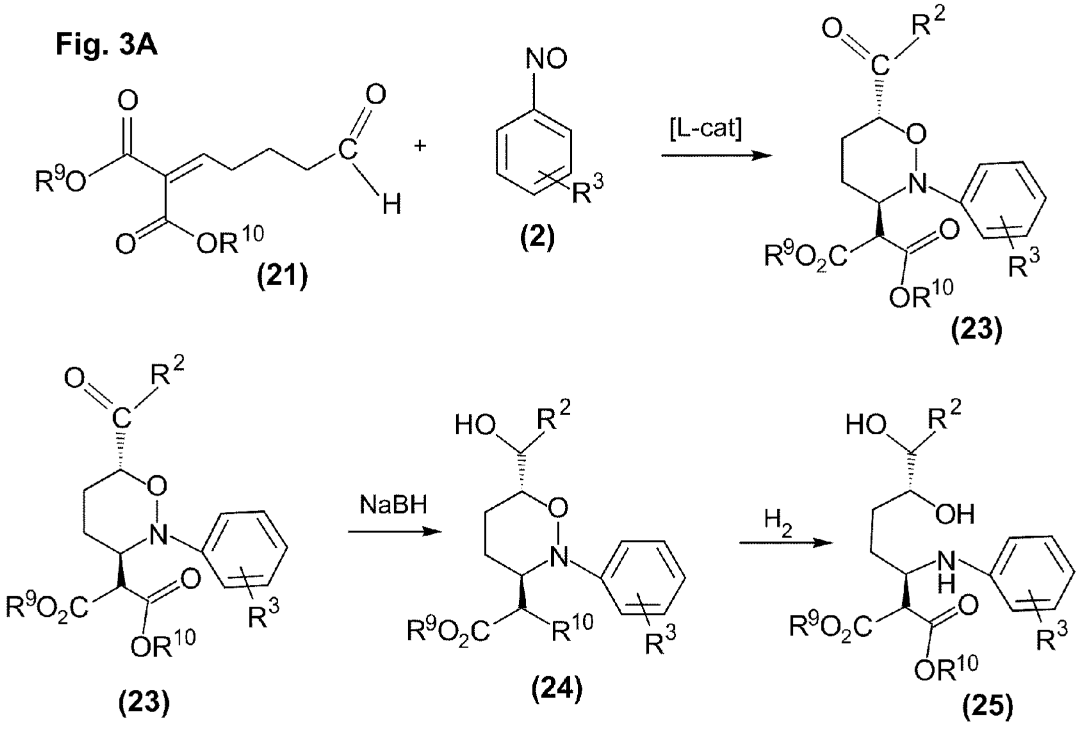
FIG. 3A shows an illustrative embodiment of the process depicted in FIG. 2A. Each of moieties Z and $R^8$ is in this example an ester group. The 1,2-oxazine compound of Formula (13) formed accordingly carries two ester groups.
Figure 3B:
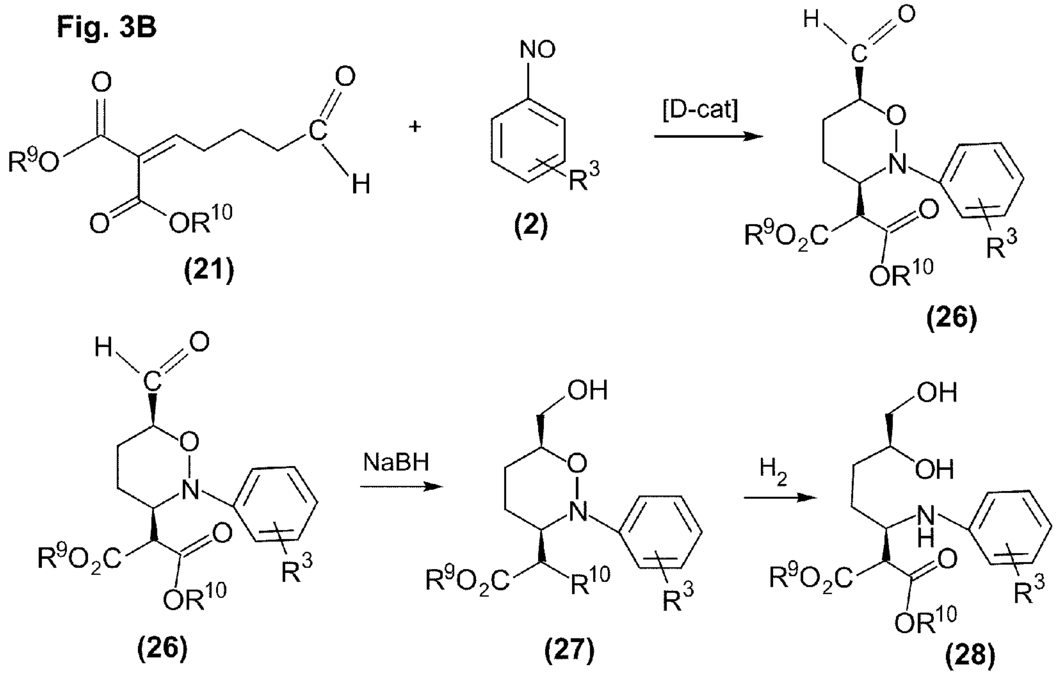
FIG. 3B illustrates the corresponding process where in the first step a chiral compound in the D form is used, thus defining an embodiment of the process depicted in FIG. 2B.
Figure 3C:
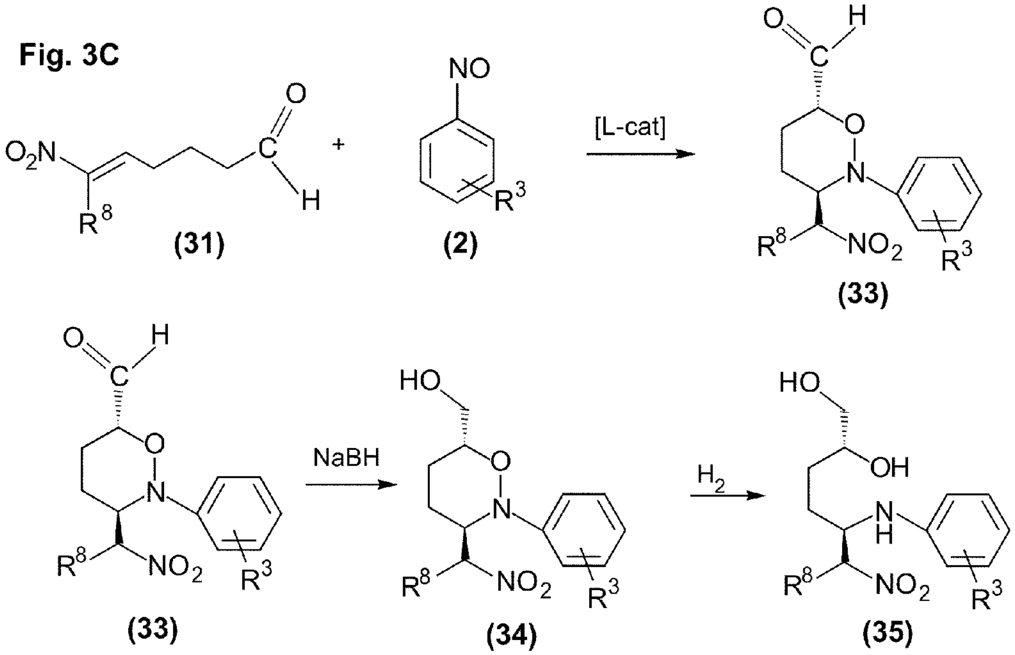
FIG. 3C depicts a further illustrative embodiment of the process depicted in FIG. 2A. Moiety Z is in this example a nitro group, so that an 1,2-oxazine compound of Formula (33) is formed.

The invention provides a process that involves forming a 2-aminoxy carbonyl compound. A 2-aminoxy carbonyl compound is typically rather labile and will therefore generally within weeks, days, hours or minutes—depending on the temperature and other conditions under which it is stored—be further processed in organic synthesis. Nevertheless, if suitable inert conditions are maintained, a 2-aminoxy carbonyl compound can be stored for extended periods of time. A simple further processing step often referred to in the following is the conversion to the corresponding 2-aminoxy alcohol. Using the process of the invention this conversion can be conveniently carried out in situ.

The 2-aminoxy carbonyl compound is of one of the general formulae (3) and (4):

(3)

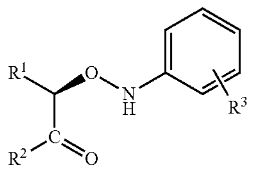

(4)

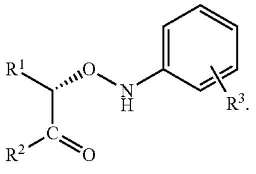

Whether a 2-aminoxy carbonyl compound of formula (3) or of formula (4) is obtained, is determined by the catalyst used (see below). The 2-aminoxy alcohol is of one of the general formulae (9) and (29):

(9)

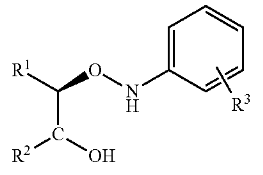

(29)

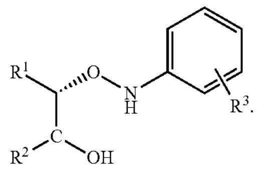

In formulae (3), (4), (9) and (29) $R^1$ is one of an aliphatic group, an alicyclic group, an aromatic group, an arylaliphatic group and an arylalicyclic group.

The term “aliphatic” means, unless otherwise stated, a straight or branched hydro-carbon chain, which may be saturated or mono- or poly-unsaturated and include heteroatoms. The term “heteroatom” as used herein means an atom of any element other than carbon or hydrogen. An unsaturated aliphatic group contains one or more double and/or triple bonds (alkenyl or alkinyl moieties). The branches of the hydrocarbon chain may include linear chains as well as non-aromatic cyclic elements. The hydrocarbon chain, which may, unless otherwise stated, be of any length, and contain any number of branches. Typically, the hydrocarbon (main) chain includes 1 to 5, to 10, to 15 or to 20 carbon atoms. Examples of alkenyl radicals are straight-chain or branched hydrocarbon radicals which contain one or more double bonds. Alkenyl radicals generally contain about two to about twenty carbon atoms and one or more, for instance two, double bonds, such as about two to about ten carbon atoms, and one double bond. Alkynyl radicals normally contain about two to about twenty carbon atoms and one or more, for example two, triple bonds, such as two to ten carbon atoms, and one triple bond. Examples of alkynyl radicals are straight-chain or branched hydrocarbon radicals which contain one or more triple bonds. Examples of alkyl groups are methyl, ethyl, propyl, butyl, pentyl, hexyl, heptyl, octyl, nonyl, decyl, the n isomers of these radicals, isopropyl, isobutyl, isopentyl, sec-butyl, tert-butyl, neopentyl, 3,3 dimethylbutyl. Both the main chain as well as the branches may furthermore contain heteroatoms as for instance N, O, S, Se or Si or carbon atoms may be replaced by these heteroatoms.

The term “alicyclic” may also be referred to as “cycloaliphatic” and means, unless stated otherwise, a non-aromatic cyclic moiety (e.g. hydrocarbon moiety), which may be saturated or mono- or poly-unsaturated. The cyclic hydrocarbon moiety may also include fused cyclic ring systems such as decalin and may also be substituted with non-aromatic cyclic as well as chain elements. The main chain of the cyclic hydrocarbon moiety may, unless otherwise stated, be of any length and contain any number of non-aromatic cyclic and chain elements. Typically, the hydrocarbon (main) chain includes 3, 4, 5, 6, 7 or 8 main chain atoms in one cycle. Examples of such moieties include, but are not limited to, cyclopentyl, cyclohexyl, cycloheptyl, or cyclooctyl. Both the cyclic hydrocarbon moiety and, if present, any cyclic and chain substituents may furthermore contain heteroatoms, as for instance N, O, S, Se or Si, or a carbon atom may be replaced by these heteroatoms. The term "alicyclic" also includes cycloalkenyl moieties that are unsaturated cyclic hydrocarbons, which generally contain about three to about eight ring carbon atoms, for example five or six ring carbon atoms. Cycloalkenyl radicals typically have a double bond in the respective ring system. Cycloalkenyl radicals may in turn be substituted. Examples of such moieties include, but are not limited to, cyclohexenyl, cyclooctenyl or cyclodecenyl.

In contrast thereto, the terms "aromatic" and "aryl" mean an at least essentially planar cyclic hydrocarbon moiety of conjugated double bonds, which may be a single ring or include multiple condensed (fused) or covalently linked rings, for example, 2, 3 or 4 fused rings. The term aromatic also includes alkylaryl. Typically, the hydrocarbon (main) chain includes 5, 6, 7 or 8 main chain atoms in one cycle. Examples of such moieties include, but are not limited to, cyclopentadienyl, phenyl, napthalenyl-, [10]annulenyl-(1,3,5,7,9-cyclodecapentaenyl-), [12]annulenyl-, [8]annulenyl-, phenalene (perinaphthene), 1,9-dihydropyrene, chrysene (1,2-benzophen-anthrene). An example of an alkylaryl moiety is benzyl. The main chain of the cyclic hydrocarbon moiety may, unless otherwise stated, be of any length and contain any number of heteroatoms, as for instance N, O and S. Such a heteroaromatic moietie may for example be a 5- to 7-membered unsaturated heterocycle which has one or more heteroatoms from the series O, N, S. Examples of such heteroaromatic moieties (which are known to the person skilled in the art) include, but are not limited to, furanyl-, thiophenyl-, naphtyl-, naphthofuranyl-, anthrathiophenyl-, pyridinyl-, pyrrolyl-, quinolinyl, naphthoquinolinyl-, quinoxalinyl-, indolyl-, benzindolyl-, imidazolyl-, oxazolyl-, oxo-ninyl-, oxepinyl-, benzoxepinyl-, azepinyl-, thiepinyl-, selenepinyl-, thioninyl-, azecinyl-, (aza-cyclodecapentaenyl-), diazecinyl-, azacyclododeca-1,3,5,7,9,11-hexaene-5,9-diyl-, azozinyl-, diazocinyl-, benzazocinyl-, azecinyl-, azaundecinyl-, thia [11]annulenyl-, oxacyclotrideca-2,4,6,8,10,12-hexaenyl- or triazaanthracenyl-moieties.

The term "arylaliphatic" means a hydrocarbon moiety, in which one or more aromatic moieties are substituted with one or more aliphatic groups. Thus the term "arylaliphatic" also includes hydrocarbon moieties, in which two or more aryl groups are connected via one or more aliphatic chain or chains of any length, for instance a methylene group. Typically, the hydrocarbon (main) chain includes 5, 6, 7 or 8 main chain atoms in each ring of the aromatic moiety. Examples of arylaliphatic moieties such as alkylaryl moieties include, but are not limited, to 1-ethyl-naphthalene, 1,1'-methylenebis-benzene, 9-isopropylanthracene, 1,2,3-trimethyl-benzene, 4-phenyl-2-buten-1-ol, 7-chloro-3-(1-methylethyl)-quinoline, 3-heptyl-furan, 6-[2-(2,5-diethyl-phenyl)ethyl]-4-ethyl-quinazoline or, 7,8-dibutyl-5,6-diethyl-isoquinoline.

The term "arylalicyclic" means a hydrocarbon moiety in which an alicyclic moiety is substituted with one or more aryl group. Three illustrative example of an arylalicyclic moiety are "phenylcyclohexyl", "phenylcyclopentyl" or "naphthyl-cyclohexyl". In typical embodiments an arylalicyclic moiety has a main chain of more than about 10 carbon atoms. In some embodiments an arylalicyclic moiety has a main chain of up to about 30 carbon atoms.

Each of the terms "aliphatic", "alicyclic", "aromatic", "arylaliphatic" and "arylalicyclic" as used herein is meant to include both substituted and unsubstituted forms of the respective moiety. Substituents my be any functional group, as for example, but not limited to, amino, amido, azido, carbonyl, carboxyl, cyano, isocyano, dithiane, halogen, hydroxyl, nitro, organometal, organoboron, seleno, silyl, silano, sulfonyl, thio, thiocyano, trifluoromethyl sulfonyl, p-toluenesulfonyl, bromobenzenesulfonyl, nitrobenzenesulfonyl, and methanesulfonyl.

In formulae (3), (4), (9) and (29) $R^2$ is one of hydrogen, an aliphatic group and an alicyclic group. The aliphatic and alicyclic groups of $R^1$ and $R^2$ may have a main chain of about 1 to about 30 carbon atoms, such as 2 to about 30 carbon atoms or 2 to about 25 carbon atoms, including about 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. The respective aliphatic, alicyclic, aromatic or arylaliphatic moiety of $R^1$, $R^2$ or $R^3$ may have 0 to about 5 heteroatoms, such as 0 to about 4 or 0 to about 3, e.g. 0, 1, 2, 3, 4 or 5 heteroatoms. A respective heteroatom may be independently selected one of N, O, S, Se and Si.

$R^3$ in formulae (3), (4), (9) and (29) is one of hydrogen, hydrogen, halogen (e.g. F, Cl, Br or I), hydroxyl and an aliphatic group. Where $R^3$ is an aliphatic group it has a main chain of 1 to about 10 carbon atoms, such as 1 to about 8 carbon atoms, 2 to about 10 carbon atoms, 3 to about 10 carbon atoms or 1 to about 5 carbon atoms, e.g. 1, 2, 3, 4, 5, 6, 7, 8, 9 or 10 carbon atoms. Further, such an aliphatic or alicyclic group may have 0, 1, 2 or 3 heteroatoms independently selected from the group consisting of N, O, S, Se and Si $R^3$ in formulae (3), (4), (9) and (29) may be bonded to any position of the aromatic ring relative to the nitrogen atom, e.g. in ortho, meta or para position. The same applies to $R^3$ in aromatic rings of other compounds named herein, such as formulae (2), (4), (13), (14), (15), (25) or (33).

In the present process of the invention a contacting a carbonyl compound of Formula (1) is provided:

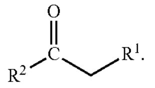

(1)

In formula (1) $R^1$ and $R^2$ are independently selected moieties as defined above.

Further, a nitroso compound of Formula (2) is provided:

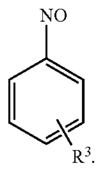

(2)

In formula (2) $R^3$ is as defined above. Further, a chiral catalyst is provided. The chiral catalyst is in some embodiments a compound of Formula (IX)

(IX)

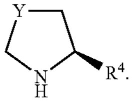

$R^4$ in formula (IX) may be a carboxyl group or the moiety

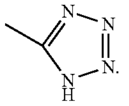

Y in formula (IX) is one of CHOH, O, S, Se, $CH_2$, CHOH, CHSH and CHSeH. Accordingly, a catalyst of formula (IX) may for example be one of the following compounds:

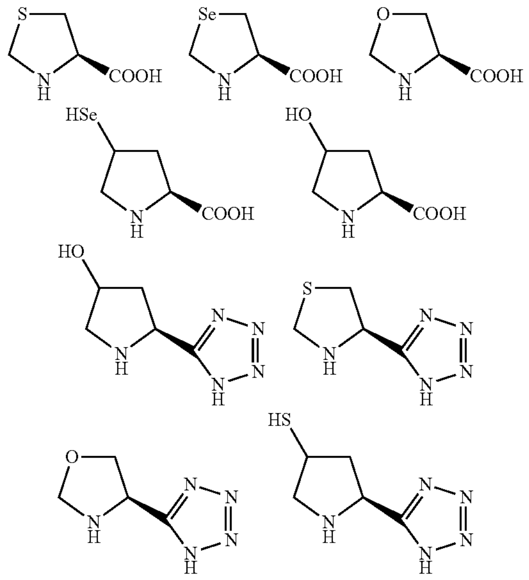

The chiral catalyst is in some embodiments a compound of Formula (V)

(V)

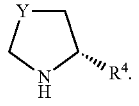

$R^4$ in formula (V), $R^5$ in formula (VI) and Y in formula (V) are as defined above (see for formulae (IX) and (X)). In embodiments where a catalyst of Formula (IX) is employed, a product of formula (3) is obtained. In embodiments where a catalyst of Formula (V) is employed, a product of formula (4) is obtained.

The reaction of the carbonyl compound of Formula (1) and the nitroso compound of Formula (2) is allowed to start by contacting these two compounds in the presence of the chiral catalyst of Formula (IX) or of Formula (V). Hence the reaction generally starts once all the three compounds are brought in contact with each other. A reaction mixture may be formed upon contacting the carbonyl compound of Formula (1) and the nitroso compound of Formula (2) in the presence of the chiral catalyst of Formulae (V) or (IX). The reaction mixture may be formed at any temperature at which the three compounds, i.e. the two reactants of formulae (1) and (2) and the catalyst are at least essentially stable enough to undergo an aminoxylation reaction. The present process of the invention is carried out in an aqueous solution. Accordingly the reaction mixture is typically formed at a temperature from about 0° C. to about 100° C., including from about 0° C. to about 80° C., from about 10° C. to about 80° C., from about 20° C. to about 80° C., from about 30° C. to about 80° C., from about 20° C. to about 50° C., from about 30° C. to about 50° C. or from about 5° C. to about 30° C., such as ambient temperature, e.g. about 18° C. The carbonyl compound of Formula (1) and the nitroso compound of Formula (2) are allowed to react in the reaction mixture at a temperature from about 5° C. to about 100° C., such as from about 10° C. to about 80° C., from about 20° C. to about 80° C., from about 20° C. to about 60° C., from about 30° C. to about 60° C., from about 20° C. to about 40° C., from about 10° C. to about 30° C. or from about 10° C. to about 25° C., including at or below about ambient temperature, e.g. at or below about 18° C.

The carbonyl compound of Formula (1) and the nitroso compound of Formula (2) are allowed to react in the reaction mixture for a period of time sufficient to allow the formation of a product of Formula (3) or of formula (4), respectively. In some embodiments the occurrence of the respective product is monitored using a suitable spectrometric and/or chromatographic technique. In some embodiments the reaction is allowed to proceed for a predetermined period of time. Such a predetermined period of time may for instance be based on optimization experiments carried out in advance. In some embodiments the carbonyl compound of Formula (1) and the nitroso compound of Formula (2) are allowed to react for a period of time selected in the range from about 10 minutes to about 48 hours, such as from about 15 minutes to about 24 hours, from about 15 minutes to about 16 hours or from about 15 minutes to about 12 hours, such as e.g. about 1, about 2, about 3, about 4, about 5, or about 6 hours.

The present process is carried out in the presence of a phase transfer catalyst. Examples of a suitable phase transfer catalyst include, but are not limited to, a quaternary ammonium salt, a quaternary phosphonium salt, a polyethylene glycol and a crown ether. Examples of a quaternary ammonium salt include, but are not limited to, tetra-n-butylammonium bromide, methyltrioctylammonium chloride, benzyltributylammonium bromide, benzyltributyl-ammonium chloride, benzyltributylammonium iodide, benzyltriethylammonium iodide, benzyl-trimethylammonium bromide, benzyltripropylammonium chloride, (2-bromoethyl)trimethyl-ammonium bromide, 2-chloroethyl)trimethylammonium chloride, (3-bromopropyl)trimethyl-ammonium bromide, (2-aminoethyl)trimethylammonium chloride, (3-carboxypropyl)trimethyl-ammonium chloride, (3-chloro-2-hydroxypropyl)trimethylammonium chloride, (4-nitrobenzyl)-trimethylammonium chloride, (5-bromopentyl) trimethylammonium bromide, (vinylbenzyl)trimethylammonium chloride, acetylcholine chloride, acetylcholine iodide, benzalkonium chloride, benzyldimethyl(2-hydroxyethyl)ammonium chloride, Benzethonium chloride, Betaine hydrochlo-ride, Carbamoylcholine chloride, benzyldimethyloctylammonium chloride, benzyldimethylde-cylammonium chloride, benzyldimethyldodecylammonium chloride, benzyldimethylhexadecyl-ammonium chloride, benzyldimethylstearylammonium chloride, benzyldodecyldimethylammo-nium bromide, bis(triphenylphosphoranylidene)ammonium chloride, Cetyltrimethylammonium chloride, Cetyltrimethylammonium hydrogensulfate, Domiphen bromide, Choline chloride, diallyldimethylammonium chloride, didecyldimethylammonium bromide, didodecyldimethyl-ammonium bromide, dihexadecyldimethylammonium bromide, dimethyldioctadecylammonium bromide, dimethyloctadecyl[3-(trimethoxysilyl)propyl] ammonium chloride, methyltrioctade-cylammonium bromide, methyltrioctylammonium iodide, tetradodecylammonium chloride, tetra-butylammonium acetate, tetramethylammonium acetate, tetrabutylammonium benzoate, tetraethylammonium trifluoroacetate, tetrabutylammonium difluorotriphenylsilicate, tetrabutylammo-nium fluorosulfate, tetrabutylammonium methanesulfonate, tetrabutylammonium nonafluoro-butanesulfonate, tetrabutylammonium nitrite, tetramethylammonium hydrogenphthalate, tetra-octylammonium hydrogen sulphate, 1,1-dimethyl-4-phenylpiperazinium iodide, 1,1'-dibenzyl-4,4'-bipyridinium dichloride, 1,2,3-trimethylimidazolium methyl sulphate, 1,3-didecyl-2-methylimidazolium chloride, 3-(2-hydroxyethyl) thiazolium bromide, 3-benzyl-5-(2-hydroxy-ethyl)-4-methylthiazolium chloride, 5-(2-Hydroxyethyl)-3,4-dimethylthiazolium iodide or Dequalinium chloride. Examples of a quaternary phosphonium salt include, but are not limited to, tetrabutylphosphonium bromide, tetrabutylphosphonium chloride, tetraoctylphosphonium bromi-de, tetraphenylphosphonium bromide, tetrabutylphosphonium hexafluorophosphate, tetrabutyl-phosphonium methanesulfonate, tetraethylphosphonium bromide, tetraethylphosphornium tetra-fluoroborate, tributyl-tetradecylphosphonium chloride, tributylhexadecylphosphonium bromide, trihexyltetradecylphosphonium bromide, 1,12-dodecanediylbis(tributylphosphonium) dibromide, benzyltriphenylphosphonium chloride, bis[tetrakis(hydroxymethyl) phosphonium] sulphate, butyl-triphenylphosphonium bromide, dimethyldiphenylphosphonium iodide, methyltriphenoxyphos-phonium iodide, ethyltriphenylphosphonium bromide, trimethylphenylphosphornium iodide and tetrakis [tris(dimethylamino)phosphoranylidenamino]phosphonium chloride.

As already mentioned, the present reaction of the present process of the invention is carried out in an aqueous solution. So far α-aminoxylation is usually carried out in organic solvents such as acetonitrile (Y. Hayashi, et al., Tetrahedron Lett. (2003) 44, 8293; A. Córdova, et al., Chem. Eur. J. (2004) 10, 3673), chloroform (S. P. Brown, et al., J. Am. Chem. Soc. (2003) 125, 10808), dichloromethane (D. B. Ramachary & I. C. F. Barbas, Org. Lett. (2005) 7, 1577), dimethylformamide (S.-G. Kim & T.-H. Park, Tetrahedron Lett. (2006) 47, 9067) and dimethylsulfoxide (G. Zhong, Angew. Chem., Int. Ed. (2003) 42, 4247; M. Lu, et al., Angew. Chem., Int. Ed., (2008) 47, 10187; D. Zhu, et al., Org. Lett. (2008) 10, 4585; G. Zhong & Y. Yu, Org. Lett. (2004) 6, 1637; G. Zhong, Chem. Commun. (2004) 606; X. Zhu, et al., J. Mol. Biol. (2004) 343, 1269; B. Tan, et al., Org. Lett. (2008) 10, 2437; B. Tan, et al., Org. Lett. (2008) 10, 3425; S. K. David, et al., Chem. Commun. (2006) 3211; H. Sundén, et al., Tetrahedron Lett. (2005) 46, 3385; W. Wang, et al., Tetrahedron Lett. (2004) 45, 7235). The use of such solvents contributes to the organic waste, whereas the process of the invention provides a more environmentally friendly protocol. Water, no doubt, is the most inexpensive and environmentally benign solvent. Further advantages that accompany the use of water as a solvent are an acceleration of reaction rates and enhancement of reaction selectivities; elimination of tedious protection-deprotection processes for certain acidic-hydrogen containing functional groups and the recycling of water-soluble catalysts after separation from water-insoluble organic products.

As explained above, the obtained carbonyl compound of formula (3) or of formula (4) may be further reduced to the corresponding 2-aminoxy alcohol of formula (9) or of formula (29), respectively, for example as disclosed by Zhong (Angew. Chem. Int. Ed (2003) 42, 4247-4250). Catalytic hydrogenation using a suitable catalyst such as Adam's catalyst may be used to cleave the O—N bond of the aminoxy compound (9) or (29), thereby yielding a diol of formula (8) or (38), respectively (ibid.)

(8)

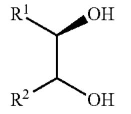

(38)

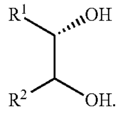

In a further aspect of the invention a process is provided, in which a 1,2-oxazine compound of Formula (13) is formed.

(13)

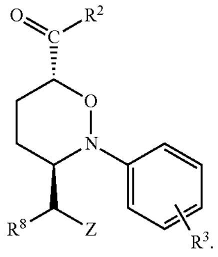

In the 1,2-oxazine compound of Formula (13) $R^2$ and $R^3$ are as defined above (see formulae (3), (4), (9) and (29)). $R^8$ is one of hydrogen, $NO_2$, CN, $C(O)R^{40}O$, $COOR^{40}$, and $CONR^{40}R^{41}$, an aliphatic group, an alicyclic group, an aromatic group, an arylaliphatic group and an arylalicyclic group. Where $R^8$ is an aliphatic, an alicyclic, an aromatic, an arylaliphatic or an arylalicyclic group it may include 0, 1, 2 or about 3 heteroatoms. Such a heteroatom may be independently selected from the group consisting of N, O, S, Se and Si. A respective aliphatic, alicyclic, aromatic, arylaliphatic or arylalicyclic group may have 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms.

Where $R^8$ is $C(O)R^{40}$, $COOR^{40}$, or $CONR^{40}R^{41}$, the moieties $R^{40}$ and $R^{41}$ are independent from one another one of hydrogen, an aliphatic group, an alicyclic group, an aromatic group, an arylaliphatic group and an arylalicyclic group. A respective aliphatic, alicyclic, aromatic, arylaliphatic or arylalicyclic group may have 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. Further, such an aliphatic, alicyclic, aromatic, arylaliphatic or arylalicyclic group may have 0, 1, 2 or 3 heteroatoms independently selected from the group consisting of N, O, S, Se and Si.

Z in Formula (13) is one of $NO_2$, CN, $C(O)R^{42}$, $COOR^{42}$, and $CONR^{42}R^{43}$. The moieties $R^{42}$ and $R^{43}$ are independent from one another one of hydrogen, an aliphatic group, an alicyclic group, an aromatic group, an arylaliphatic group and an arylalicyclic group. A respective aliphatic, alicyclic, aromatic, arylaliphatic or arylalicyclic group may have 1 to about 20 carbon atoms, about 2 to about 20 carbon atoms, about 3 to about 20 carbon atoms, about 1 to about 15 carbon atoms, about 2 to about 15 carbon atoms, about 1 to about 10 carbon atoms, about 2 to about 10 carbon atoms or about 1 to about 10 carbon atoms, such as 1, 2, 3, 4, 5, 6, 7, 8, 9, 10, 11, 12, 13, 14, 15, 16, 17, 18, 19 or 20 carbon atoms. Further, such an aliphatic, alicyclic, aromatic, arylaliphatic or arylalicyclic group may have 0, 1, 2 or 3 heteroatoms independently selected from the group consisting of N, O, S, Se and Si.

The process of forming a 1,2-oxazine compound of Formula (13) includes providing a carbonyl compound of Formula (11):

(11)

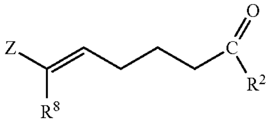

In Formula (11) $R^2$ and $R^8$ are as defined above. The process further includes providing a nitroso compound of Formula (2), as defined above. Further, a chiral catalyst is provided. The chiral catalyst is a compound of Formula (IX) or of Formula (X), as already defined above. The reaction of the carbonyl compound of Formula (11) and the nitroso compound of Formula (2) is allowed to start by contacting these two compounds in the presence of the chiral catalyst of Formula (IX) or of Formula (X). Hence the reaction generally starts once all the three compounds are brought in contact with each other. The carbonyl compound of Formula (11) is contacted with a nitroso compound of Formula (2) in the presence of the chiral catalyst of Formula (IX) or of Formula (X). Thereby a reaction mixture is formed. The reaction mixture may be formed at any temperature at which the three compounds, i.e. the two reactants of formulae (11) and (2) and the catalyst are at least essentially stable enough to undergo an aminoxylation reaction. The reaction mixture may for instance be formed at a temperature from about −180° C. to about 200° C., including from about −120° C. to about 200° C., from about −80° C. to about 200° C., from about −180° C. to about 150° C., from about −120° C. to about 160° C., from about −80° C. to about 140° C., from about −80° C. to about 100° C., from about −80° C. to about 60° C. or from about −80° C. to about 30° C., such as at about −70° C., at about −20° C., at about 0° C. or at ambient temperature, e.g. about 18° C.

The reaction of the present process of the invention is generally carried out in the liquid phase. Any solvent may be used, as long as the compounds used dissolve therein sufficiently. Solvents used may be polar or non-polar liquids, including aprotic non-polar liquids. Examples of non-polar liquids include, but are not limited to mineral oil, hexane, heptane, cyclohexane, benzene, toluene, dichloromethane, chloroform, carbon tetrachloride, carbon disulfide, dioxane, diethyl ether, diisopropylether, methyl propyl ketone, methyl isoamyl ketone, methyl isobutyl ketone, cyclohexanone, isobutyl isobutyrate, ethylene glycol diacetate, and a non-polar ionic liquid. Examples of a non-polar ionic liquid include, but are not limited to, 1-ethyl-3-methylimidazolium bis[(trifluoromethyl)sulfonyl]amide bis(triflyl)amide, 1-ethyl-3-methylimidazolium bis[(trifluoromethyl)sulfonyl]amide trifluoroacetate, 1-butyl-3-methylimidazolium hexafluorophosphate, 1-hexyl-3-methylimidazolium bis(trifluoromethylsulfonyl)imide, 1-butyl-3-methylimidazolium bis(trifluoromethylsulfonyl)imide, trihexyl(tetradecyl) phosphonium bis[oxa-late(2-)]borate, 1-hexyl-3-methyl imidazolium tris(pentafluoroethyl)trifluorophosphate, 1-butyl-3-methyl-imidazolium hexafluorophosphate, tris(pentafluoroethyl)trifluorophosphate, trihexyl-(tetradecyl)phosphonium, N"-ethyl-N,N,N',N'-tetramethylguanidinium, 1-butyl-1-methylpyrro-ledinium tris(pentafluoroethyl) trifluorophosphate, 1-butyl-1-methylpyrrolidinium bis(trifluoro-methylsulfonyl) imide, 1-butyl-3-methyl imidazolium hexafluorophosphate, 1-ethyl-3-methyl-imidazolium bis(trifluoromethylsulfonyl)imide and 1-n-butyl-3-methylimidazolium. Exemplary aprotic non-polar liquids include hexane, heptane, cyclohexane, benzene, toluene, pyridine, dichloromethane, chloroform, carbon tetrachloride, carbon disulfide, dioxane, diethyl ether, diisopropylether, ethylene glycol monobutyl ether and tetrahydrofuran.

Examples of a polar solvent include, but are not limited to, dioxane, diethyl ether, diisopropylether, ethylene glycol monobutyl ether, tetrahydrofuran, methyl propyl ketone, methyl isoamyl ketone, methyl isobutyl ketone, cyclohexanone, isobutyl isobutyrate, ethylene glycol diacetate, and a polar ionic liquid. Examples of a polar ionic liquid include, but are not limited to, 1-ethyl-3-methylimidazolium tetrafluoroborate, N-butyl-4-methylpyridinium tetrafluoroborate, 1,3-dialkylimidazolium-tetrafluoroborate, 1,3-dialkylimidazolium-hexafluoroborate, 1-ethyl-3-methylimidazolium bis(pentafluoroethyl)phosphinate, 1-butyl-3-methylimidazolium tetrakis(3,5-bis(trifluoromethylphenyl)borate, tetrabutyl-ammonium bis(trifluoromethyl)imide, ethyl-3-methylimidazolium trifluoromethanesulfonate, 1-butyl-3-methylimidazolium methylsulfate, 1-n-butyl-3-methylimidazolium ([bmim]) octylsulfate, and 1-n-butyl-3-methylimidazolium tetra-fluoroborate.

A polar protic solvent that may be used can be a solvent that has, for example, a hydrogen atom bound to an oxygen atom as in a hydroxyl group or a nitrogen as in an amine group. More generally, any molecular solvent which contains dissociable $H^+$, such as hydrogen fluoride, is called a protic solvent. The molecules of such solvents can donate an $H^+$ (proton). The examples of polar solvents named above with the exception of ionic liquids are aprotic solvents. In some embodiments the solvent used in the reaction of the present process of the invention is an aprotic polar liquid. In some embodiments the solvent used is a polar protic solvent. Examples of polar protic solvents include, but are not limited to, water, an alcohol or a carboxylic acid. Examples of an alcohol include, but are not limited to, methanol, ethanol, 1,2-ethanediol (ethylene glycol), 1,3-propanediol (β-propylene glycol), 1,2-propanediol, n-propanol, iso-propanol, n-butanol, iso-butanol, tert-butanol, 2-butanol, 2,3-butanediol (dimethylethylene glycol), 2-methyl-1,3-propanediol, 1-pentanol (amyl alcohol), 2-pentanol, 2-methyl-3-butanol, 3-methyl-1-butanol (iso-pentanol), 3-pentanol (sec-amyl alcohol), 2,4-pentanediol (2,4-amylene glycol), 4-methyl-1,7-heptanediol, 1,9-nonanediol, cyclohexanol, propoxymethanol and 2-ethoxyethanol (ethylene glycol ethyl ether). As four illustrative examples of a carboxylic acid may serve acetic acid, propionic acid, valeric acid and caproic acid. In one embodiment of the present invention water may be used. Various protic ionic liquids may be tested for their suitability as a solvent for carrying out a method of the invention. Protic ionic liquids are formed through the combination of a Brønsted acid and Brønsted base (see Greaves, T. L., & Drummond, C. J., Chem. Rev. (2008) 108, 206-237).

The carbonyl compound of Formula (11) and the nitroso compound of Formula (2) may be allowed to react in the reaction mixture at any desired temperature, including at a temperature from about −200° C. to about 200° C., depending on the boiling point of the solvent selected. The reaction may for example be allowed to proceed at a temperature in the range from about −120° C. to about 180° C., from about −100° C. to about 180° C., from about −80° C. to about 200° C., from about −80° C. to about 170° C., from about −80° C. to about 120° C. or from about −80° C. to about 100° C., such as at about −70° C., at about −20° C., at about −10° C. or at about 0° C., including at or below about ambient temperature, e.g. at or below about 18° C. or at or below 25° C.

By allowing the carbonyl compound of Formula (1) and the nitroso compound of Formula (2) to react in the reaction mixture, the formation of the 1,2-oxazine compound of Formula (13) is allowed to occur. In some embodiments the occurrence of the respective product is monitored using a suitable spectrometric and/or chromatographic technique. In some embodiments the reaction is allowed to proceed for a predetermined period of time. Such a predetermined period of time may for instance be based on optimization experiments carried out in advance. In some embodiments the carbonyl compound of Formula (11) and the nitroso compound of Formula (2) are allowed to react for a period of time selected in the range from about 10 minutes to about 48 hours, such as from about 15 minutes to about 48 hours, from about 15 minutes to about 24 hours, from about 15 minutes to about 16 hours or from about 15 minutes to about 12 hours, such as e.g. about 1, about 2, about 3, about 4, about 5, or about 6 hours.

The reaction of the present process of the invention provides a direct tandem α-aminoxylation/aza-Michael reaction of carbonyl compounds such as aldehydes. The reaction is highly diastereo- and enantioselective. In some embodiments it bears a remote enemalonate as Michael acceptor at the δ-position for the synthesis of functionalized tetrahydro-1,2-oxazines (THOs), among which both C—O and C—N bonds can be formed in excellent stereoselectiy. On a general basis this process provides a useful tool in synthesis strategy as illustrated by an exemplary use of an aldehyde with an 1,3-dicarboxyl moiety, nitrosobenzene and L-proline as the catalyst, in the following general illustration:

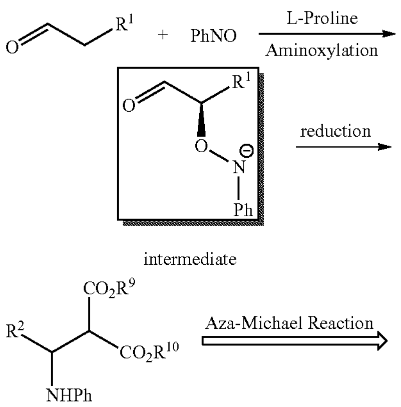

-continued

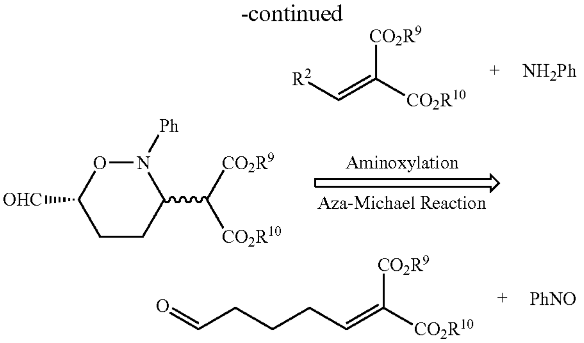

Figure 7B:
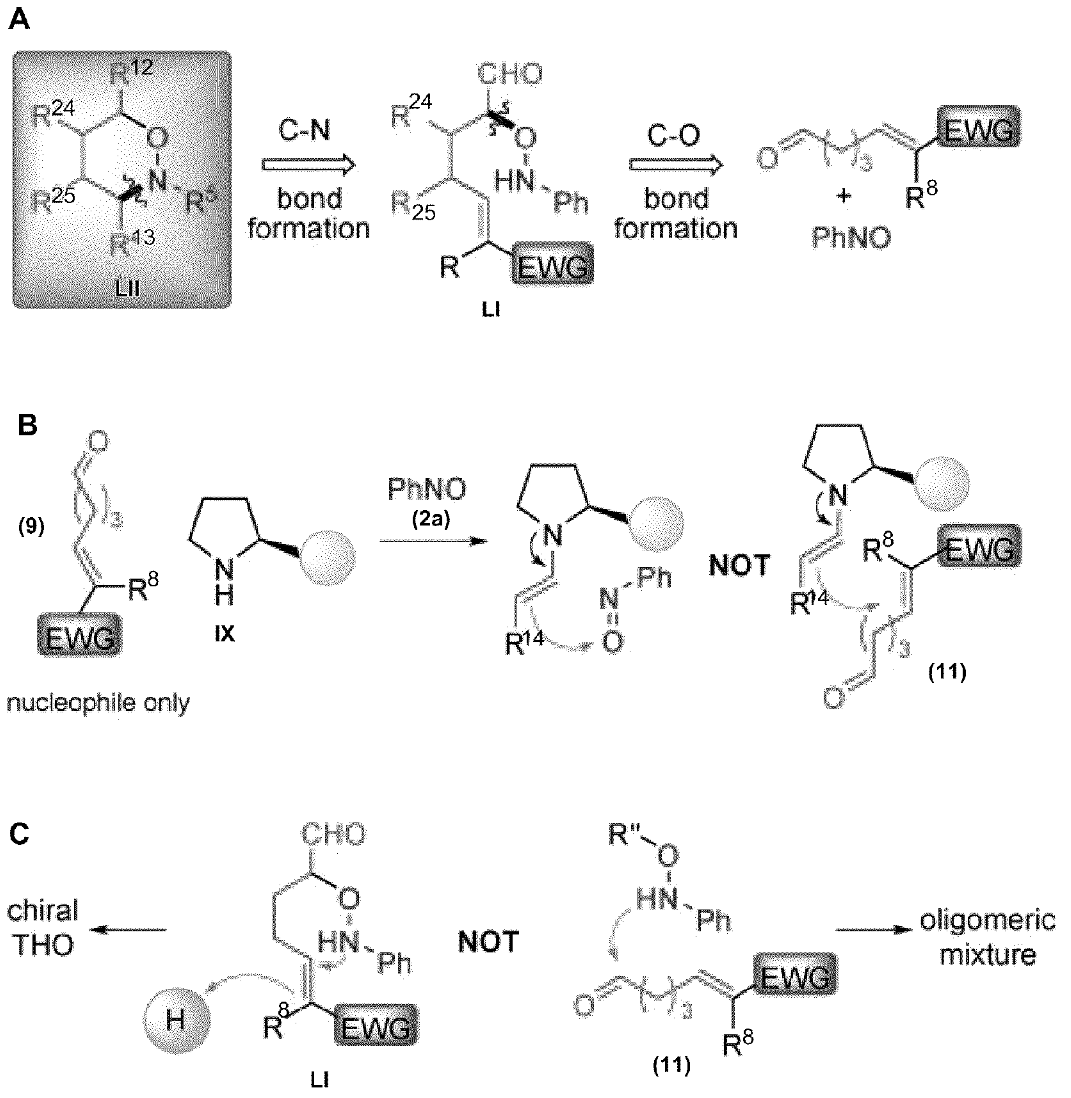
FIG. 7B illustrates by means of a scheme the synthesis of chiral for tetrahydro-1,2-oxazines LII. a) Enantioselective organocatalytic tetrahydro-1,2-oxazine synthesis by a C—O/C—N sequence. b) Enamine-catalyzed α-aminoxylation versus Michael addition. c) Aza-Michael addition versus nucleophilic attack on the C═O group and subsequent asymmetric protonation. EWG=electron-withdrawing group.

As illustrated in FIG. 7B, on a general basis the structure of a tetrahydro-1,2-oxazine could for instance be assembled by using two reactions to form both the C—O and C—N bonds. For example, a potential route could be the α-aminoxylation of alkenal (9) with nitrosobenzene (2a) and subsequent nucleophilic attack of the in situ generated amine on Michael acceptor (LI). As can be taken from the various possible reaction routes and the various stereochemical possibilities, the reaction of the process of the invention surprisingly proceeds in a highly controlled manner. Without being bound by theory it is believed that aza-Michael addition and protonation take place in a concerted manner by a preferred transition state.

In order that the invention may be readily understood and put into practical effect, particular embodiments will now be described by way of the following non-limiting examples.

Exemplary Embodiments of the Invention

EXAMPLE 1

α-Aminoxylation of Aldehydes

To probe the feasibility of the α-aminoxylation of aldehydes in aqueous media and phase-transfer catalyst, we first performed α-aminoxylation of propanal to nitrosobenzene in the presence of L-proline IXa, tetrabutylammonium bromide and water at 0° C. and then warmed to room temperature. To our disappointment, the yield obtained in this initial reaction was rather low, despite the high enantioselectivity achieved. This prompted us to screen more catalysts IXb-IXd, Xa and XL (FIG. 4, entries 2-6). Among all the catalysts investigated, only L-thiaproline IXd gave a higher yield than IXa. Although IXd took a longer reaction time and gave a slightly lower enantioselectivity than IXa, we believed that higher enantioselectivity could be achieved with the optimization of reaction conditions. This is the first instance where L-thiaproline IXd was used as a catalyst in α-aminoxylation. The use of IXd will potentially reduce much hassle for stereo-selective reactions as it is commercially available.

Figure 5:
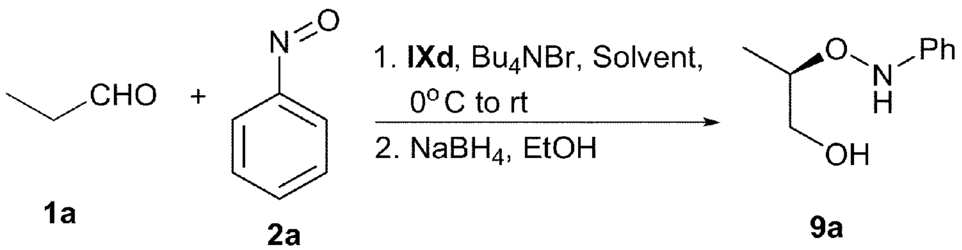
FIG. 5 illustrates the optimisation of reaction conditions of the reaction depicted in FIG. 4, using catalyst IXd. Conditions: Nitrosobenzene (0.3 mmol), propanal (3 equiv), catalyst (20 mol %), tetrabutylammonium bromide (2 equiv) and water (0.10 mL) were added at 0° C. and stirred at rt (23° C.) unless otherwise stated. a: Isolated yields. b: Determined by chiral phase HPLC. c: 10 mol % of VI. d: 30 mol % of VI. e: No $Bu_4NBr$ added. f: 1 equiv $Bu_4NBr$ added. g: 1 equiv propanal added. h: 2 equiv propanal added.

For the optimisation of reaction condition, we first investigated the effect of catalyst loading on the reaction (FIG. 5, entries 1-3). Highest yield and enantioselectivity were obtained when 20 mol % of catalyst was used. The results of the reaction did not improve when neat condition was used (FIG. 5, entry 4). Screenings of various organic solvents revealed that chloroform and dimethyl sulfoxide, preferred solvents for many α-aminoxylation reactions, were not the best solvents when VI was employed as catalyst (FIG. 5, entries 5-6). Although acetonitrile gave comparable enantioselectivity, its lower yield and longer reaction time made water the preferred choice of solvent for this reaction (FIG. 5, entry 7). We discovered that 0.10 mL of water is the optimum amount of water added to the system to attain the highest yield and enantioselectivity achievable (FIG. 5, entries 8-10). Both the yield and enantioselectivity dropped when the amount of phase transfer catalyst was reduced (FIG. 5, entries 11-12). Similar trend was also observed with decreasing amounts of propanal (FIG. 5, entries 13-14).

With optimal reaction conditions established, we probed the scope of the reaction for a variety of aldehydes. The results are summarized in FIG. 6. In the cases investigated, the α-aminoxy alcohols were obtained in good to high yields (74-88%) and excellent enantioselectivies (93->99%). The L-thiaproline α-aminoxylation reaction between nitrosobenzene and propanal was completed in 2 h with good yield (84%) and excellent enantioselectivity (96%) (FIG. 6, entry 1). Not only propanal, but linear chain aldehydes such as n-butanal, n-pentanal and n-hexanal react with nitrosobenzene, affording α-aminoxy alcohols in good yield with excellent enantioselectivities (FIG. 6, entries 2-4). Branched aldehydes such as 3-methylbutanal are also suitable substrates as it was also successfully converted to the □-aminoxy alcohols in good yield with excellent enantioselectivity (FIG. 6, entry 5). Aldehydes containing an aromatic moiety such as phenylacetaldehyde and 3-phenylpropanal were successfully employed in this reaction (FIG. 6, entries 6 and 7). It is interesting to note that the reaction time for phenylacetylaldehyde was significantly reduced. This may be due to the activating effect of the benzene ring on the α-position of the phenylacetylaldehyde. The introduction of a terminal double bond on the aldehyde does not drastically affect the yield and enantioselevitvity of the reaction (FIG. 6, entry 8). The reaction also proceeded smoothly with protective groups such as benzyl ethers and tert-butoxycarbonyl carbamates to afford the □-aminoxy leohols in good yield with excellent enantioselectivities (FIG. 6, entries 9-10). The scope of nitroso compounds was briefly tested by replacing nitrosobenzene with nitrosotoluene. When nitrosotoluene was treated with propanal under the optimised conditions, the corresponding α-aminoxy alcohol was obtained in 83% yield with an enantioselecitivity of 97%, which is consistent with the results of nitrosobenzene.

Conclusions

In conclusion, L-thiaproline catalyzed α-aminoxylation of aldehydes in aqueous media and phase-transfer catalyst afforded the respective α-aminoxy alcohols in good to high yields (74-88%) and excellent enantioselectivies (93->99%). This reaction protocol may find potential use for industrial-scale preparation due to its simple operation procedures, wide scope, excellent enantioselectivities and environmental friendliness. Further investigation on the application of L-thioproline in asymmetric catalysis is in progress.

General Experimental Information

Analytical thin layer chromatography (TLC) was performed using Merck 60 F254 precoated silica gel plate (0.2 mm thickness). Subsequent to elution, plates were visualized using UV radiation (254 nm) on Spectroline Model ENF-24061/F 254 nm. Further visualization was possible by staining with basic solution of potassium permanganate or acidic solution of ceric molybdate. Flash chromatography was performed using Merck silica gel 60 with freshly distilled solvents. Columns were typically packed as slurry and equilibrated with the appropriate solvent system prior to use.

Proton nuclear magnetic resonance spectra ($^1$H NMR) were recorded on Bruker AMX 400 spectrophotometer ($CDCl_3$ as solvent). Chemical shifts for $^1$H NMR spectra are reported as δ in units of parts per million (ppm) downfield from $SiMe_4$ (δ 0.0) and relative to the signal of $SiMe_4$ (δ 0.0, singlet). Multiplicities were given as: s (singlet), d (doublet), t (triplet), dd (doublets of doublet) or m (multiplets). The number of protons (n) for a given resonance is indicated by nH. Coupling constants are reported as a J value in Hz. Carbon nuclear magnetic resonance spectra ($^{13}$C NMR) are reported as 6 in units of parts per million (ppm) downfield from $SiMe_4$ (δ 0.0) and relative to the signal of chloroform-d (δ 77.03, triplet).

Enantioselectivities were determined by High Performance Liquid Chromatography (HPLC) analysis employing a Daicel Chirapak AD-H (0.46 cm×25 cm), OD-H (0.46 cm×25 cm) or OJ-H (0.46 cm×25 cm) column.

Optical rotations were measured in $CHCl_3$ on a Schmidt+Haensdch polarimeter (Polartronic MH8) with a 1 cm cell (c given in g/100 mL). Absolute configuration of the products was determined by comparison with compounds previously published.

Aldehydes 1i and 1j were prepared according to literature procedures (preparation of 1i: Iyengar, R, et. al., *J. of Org. Chem.* (2005) 70, 10645; preparation of 1j: More, J D, & Finney, N S, *Org. Lett.* (2002) 4, 3001). The enantiomers used to determine the ee values were synthesized with DL-proline as catalyst. All other reagents were available from commercial sources and used without further purification.

Typical Procedure for the α-Aminoxylation of Aldehydes to Nitrosobenzene in the Presence of Water Water (0.10 mL) and tetrabutylammonium bromide (193.4 mg, 0.6 mmol) was added to a 5 mL drum vial containing nitrosobenzene 2 (32.1 mg, 0.3 mmol), corresponding aldehyde 1 (e.g. 1a) (0.9 mmol) and a magnetic stirring bar. After stirring for 5 min at 0° C., L-thiaproline (8 mg, 0.06 mmol) was then added. The reaction was first stirred at this temperature for about 10 min and then at room temperature until the green solution turned yellow which indicated complete consumption of the nitrosobenzene. As the α-aminoxy aldehyde product is rather labile, isolation and characterization was performed after conversion to the corresponding α-aminoxy alcohol 9a by treatment of the reaction mixture with $NaBH_4$. The excess $NaBH_4$ was quenched by the addition of water and then extracted with $CH_2Cl_2$ (3×30 ml). The combined organic extracts were dried with $Na_2SO_4$ and concentrated in vacuo. The crude oil was purified by flash column chromatography (hexane/EtOAc=9/1~7/3) yielding pure α-aminoxy alcohols 9a.

Relative and absolute configurations of the products were compared with the known $^1$H NMR, chiral HPLC analysis, and optical rotation values. The compounds in FIG. 6 as such have previously been disclosed in the art.

In the following exemplary data on the formation of a series of amineoxy compounds are provided. Following the foregoing protocol products were obtained, isolated and characterized.

Experimental data of Compounds 9a-9k (R)-2-(N-Phenylaminoxy)propan-1-ol (3a) [Hayashi, Y, et al., *J. Org. Chem.* (2004) 69, 5966]

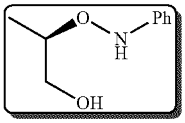

α-Aminoxy alcohol 9a was prepared according to the general procedure from propanal (0.07 mL, 0.9 mmol) to provide the title compound as a pale yellow liquid (42.3 mg, 84% yield) after flash column chromatography on silica gel (hexane/EtOAc=9/1~7/3). Prepared according to the general procedure to provide the title compound (96% yield).

$^1$H-NMR (400 MHz, $CDCl_3$) δ 7.29-7.25 (2H, m), 7.04-6.96 (3H, m), 4.16-4.08 (1H, m), 3.80-3.70 (2H, m), 2.56 (1H, brs), 1.25 (3H, d, J=6.4 Hz).

$^{13}$C-NMR (100 MHz, $CDCl_3$) δ 148.5, 129.0, 122.4, 114.7, 80.0, 66.5, 15.4.

HPLC: Chiralpak AD-H (hexane/i-PrOH, 90/10, flow rate 1 mL/min, λ=230 nm), $t_R$ (minor)=10.6 min, $t_R$ (major)=12.1 min; 96% ee.

$[\alpha]_D^{25}$=+2.9 (c=1.0, $CHCl_3$).

(R)-2-(N-Phenylaminoxy)butan-1-ol (9b) [Hayashi, Y, et al., *J. Org. Chem.* (2004) 69, 5966]

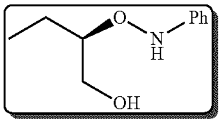

α-Aminoxy alcohol 9b was prepared according to the general procedure from butanal (0.08 mL, 0.9 mmol) to provide the title compound as a pale yellow liquid (40.9 mg, 75% yield) after flash column chromatography on silica gel (hexane/EtOAc=9/1~7/3).

$^1$H-NMR (400 MHz, $CDCl_3$) δ 7.29-7.25 (2H, m), 7.07-6.96 (2H, m), 3.91-3.74 (3H, m), 2.67 (1H, brs), 1.78-1.53 (2H, m), 1.01 (3H, t, J=7.5 Hz).

$^{13}$C-NMR (100 MHz, $CDCl_3$) δ 148.4, 129.0, 122.4, 114.8, 85.3, 64.9, 22.9, 10.1.

HPLC: Chiralpak AD-H (hexane/i-PrOH, 90/10, flow rate 1 mL/min, λ=230 nm), $t_R$ (minor)=10.2 min, $t_R$ (major)=11.6 min; 98% ee.

$[\alpha]_D^{23}$=+36.0 (c=1.0, $CHCl_3$).

(R)-2-(N-Phenylaminoxy)pentan-1-ol (9c) [Hayashi, Y, et al., *J. Org. Chem.* (2004) 69, 5966]

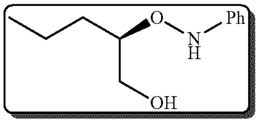

α-Aminoxy alcohol 9c was prepared according to the general procedure from pentanal (0.10 mL, 0.9 mmol) to provide the title compound as a pale yellow liquid (46.0 mg, 79% yield) after flash column chromatography on silica gel (hexane/EtOAc=9/1~7/3).

$^1$H-NMR (400 MHz, $CDCl_3$) δ 7.28-7.15 (3H, m), 6.98-6.94 (2H, m), 3.94-3.91 (1H, m), 3.85-3.82 (1H, m), 3.75-3.71 (1H, m), 2.93 (1H, brs), 1.67-1.61 (1H, m), 1.54-1.33 (3H, m), 0.97-0.89 (3H, m).

HPLC: Chiralpak AD-H (hexane/i-PrOH, 90/10, flow rate 1 mL/min, λ=230 nm), $t_R$ (minor)=10.0 min, $t_R$ (major)=11.4 min; 97% ee.

$[\alpha]_D^{23}$=+28.6 (c=1.0, $CHCl_3$).

(R)-2-(N-Phenylaminoxy)hexan-1-ol (9d) [Córdova, A, et al., *Chem. Eur. J.* (2004) 10, 3673]

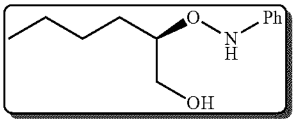

α-Aminoxy alcohol 9d was prepared according to the general procedure from hexanal (0.11 mL, 0.9 mmol) to provide the title compound as a pale yellow liquid (46.4 mg, 74% yield) after flash column chromatography on silica gel (hexane/EtOAc=9/1~7/3).

$^1$H NMR (400 MHz, $CDCl_3$): δ 7.29-7.26 (2H, m), 7.06-6.96 (3H, m), 3.98-3.92 (1H, m), 3.87-3.84 (1H, m), 3.79-3.72 (1H, m), 2.68 (1H, brs), 1.69-1.50 (1H, m), 1.47-1.30 (4H, m), 0.92 (3H, t, J=7.1 Hz).

$^{13}$C NMR (100 MHz, $CDCl_3$): 148.4, 129.0, 122.5, 114.9, 84.0, 65.4, 29.6, 27.9, 22.0, 14.0.

HPLC: Chiralpak AD-H (hexane/i-PrOH, 90/10, flow rate 1 mL/min, λ=230 nm), $t_R$ (minor)=9.5 min, $t_R$ (major)=11.4 min; 96% ee.

$[\alpha]_D^{23}$=+22.5 (c=1.2, $CHCl_3$).

(R)-3-Methyl-2-(N-phenylaminooxy)butan-1-ol (9e) (Córdova, A, et al., Chem. Eur. J. (2004) 10, 3673)

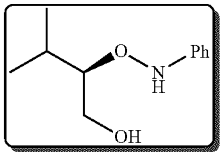

α-Aminoxy alcohol 9e was prepared according to the general procedure from 3-methylbutanal (0.10 mL, 0.9 mmol) to provide the title compound as a pale yellow liquid (44.8 mg, 76% yield) after flash column chromatography on silica gel (hexane/EtOAc=9/1~7/3).

$^1$H NMR (400 MHz, $CDCl_3$): δ 7.30-7.26 (2H, m), 7.03-6.99 (3H, m), 3.88-3.87 (2H, m), 3.76-3.74 (1H, m), 2.07-1.99 (1H, m), 1.05 (3H, d, J=6.9 Hz), 1.01 (3H, d, J=6.9 Hz).

$^{13}$C NMR (100 MHz, $CDCl_3$): 148.3, 129.0, 122.5, 115.0, 88.6, 63.6, 28.7, 18.7, 18.6.

HPLC: Chiralpak AD-H (hexane/i-PrOH, 90/10, flow rate 1 mL/min, λ=230 nm), $t_R$ (minor)=9.0 min, $t_R$ (major)=10.1 mins; 97% ee.

$[\alpha]_D^{22}$=+33.4 (c=1.0, $CHCl_3$).

(R)-2-Phenyl-2-(N-phenylaminooxy)ethanol (90 [Hayashi, Y, et al., *J. Org. Chem.* (2004) 69, 5966]

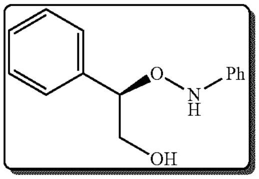

α-Aminoxy alcohol 9f was prepared according to the general procedure from 2-phenylacetaldehyde (0.11 mL, 0.9 mmol) to provide the title compound as a pale yellow liquid (53.5 mg, 78% yield) after flash column chromatography on silica gel (hexane/Ether=9/1~7/3).

$^1$H NMR (400 MHz, $CDCl_3$): δ 7.39-7.31 (5H, m), 7.28-7.20 (2H, m), 6.99-6.94 (3H, m), 5.00 (1H, dd, J=3.5, 8.1 Hz), 3.99-3.92 (1H, m), 3.83-3.78 (1H, m), 2.58 (1H, brs).

$^{13}$C NMR (100 MHz, $CDCl_3$): 147.9, 137.7, 129.0, 128.7, 128.5, 127.0, 122.5, 115.0, 86.4, 66.4.

HPLC: Chiralpak OD-H (hexane/i-PrOH, 95/5, flow rate 1 mL/min, λ=230 nm), $t_R$ (major)=25.8 mins, $t_R$ (minor)=30.2 min; 93% ee.

$[\alpha]_D^{24}$=−85.5 (c=1.1, $CHCl_3$).

(R)-3-Phenyl-2-(N-phenylaminooxy)propan-1-ol (3 g) [Hayashi, Y, et al., *J. Org. Chem.* (2004)

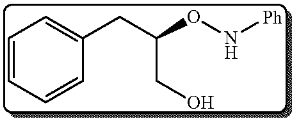

α-Aminoxy alcohol 9g was prepared according to the general procedure from 3-phenylpropanal (0.12 mL, 0.9 mmol) to provide the title compound as a pale yellow liquid (55.9 mg, 77% yield) after flash column chromatography on silica gel (hexane/Ether=9/1~7/3).

$^1$H NMR (400 MHz, $CDCl_3$): δ 7.32-7.18 (6H, m), 7.08 (1H, brs), 6.94 (1H, t, J=7.3 Hz), 6.82 (2H, d, J=8.0 Hz), 4.16-4.10 (1H, m), 3.85 (1H, d, J=11.8 Hz), 3.04 (1H, dd, J=6.8, 13.7 Hz), 2.84 (1H, dd, J=7.0, 13.7 Hz), 2.62 (1H, brs).

$^{13}$C NMR (100 MHz, $CDCl_3$): 148.3, 137.8, 129.4, 128.9, 128.5, 126.4, 122.3, 114.6, 85.0, 64.1, 36.4.

HPLC: Chiralpak OD-H (hexane/i-PrOH, 91/9, flow rate 1 mL/min, λ=230 nm), $t_R$ (major)=57.9 min, $t_R$ (minor)=62.4 min; >99% ee.

$[\alpha]_D^{22}$=+55.2 (c=1.3, $CHCl_3$).

(R)-2-(N-Phenylaminooxy)pent-4-en-1-ol (9h)(Córdova, A, et al., 2004, supra)

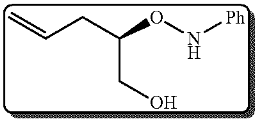

α-Aminoxy alcohol 3h was prepared according to the general procedure from 4-pentenal (0.09 mL, 0.9 mmol) to provide the title compound as a pale yellow liquid (51.0 mg, 88% yield) after flash column chromatography on silica gel (hexane/EtOAc=9/1~7/3).

$^1$H NMR (400 MHz, $CDCl_3$): δ 7.29-7.26 (2H, m), 7.06-6.96 (3H, m), 5.93-5.82 (1H, m), 5.18-5.11 (2H, m), 4.05-4.00 (1H, m), 3.87-3.75 (2H, m), 2.54-2.32 (3H, m), 1.66 (1H, brs).

$^{13}$C NMR (100 MHz, $CDCl_3$): 148.3, 134.0, 129.0, 122.5, 117.8, 114.8, 83.3, 64.6, 34.6.

HPLC: Chiralpak AD-H (hexane/i-PrOH, 90/10, flow rate 1 mL/min, λ=230 nm), $t_R$ (minor)=10.5 min, $t_R$ (major)=12.5 min; 96% ee.

$[\alpha]_D^{23}$=−22.9 (c=1.0, $CHCl_3$).

(R)-4-(Benzyloxy)-2-(N-phenylaminooxy)butan-1-ol (new compound) (9i)

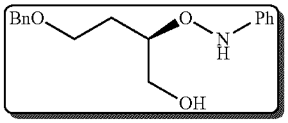

α-Aminoxy alcohol 9i was prepared according to the general procedure from 4-(benzyloxy)butanal (0.16 mL, 0.9 mmol) to provide the title compound as a pale yellow liquid (73.8 mg, 86% yield) after flash column chromatography on silica gel (hexane/EtOAc=9/1~7/3).

$^1$H NMR (400 MHz, $CDCl_3$): δ 7.34-7.23 (6H, m), 7.05 (1H, brs), 6.98-6.94 (3H, m), 4.54-4.52 (2H, m), 4.14-4.11 (1H, m), 3.93-3.87 (1H, m), 3.81-3.77 (1H, m), 3.66 (2H, t, J=5.7 Hz), 2.81 (1H, t, J=5.9 Hz), 2.06-1.89 (2H, m).

$^{13}$C NMR (100 MHz, $CDCl_3$): 148.3, 138.0, 129.0, 128.5, 127.8, 122.4, 116.1, 114.8, 81.5, 73.2, 66.7, 64.8, 30.3.

HPLC: Chiralpak AD-H (hexane/i-PrOH, 91/9, flow rate 1 mL/min, λ=230 nm), $t_R$ (minor)=18.8 min, $t_R$ (major)=24.1 min; 97% ee.

$[\alpha]_D^{22}$=+15.5 (c=1.1, $CHCl_3$).

HRMS (ESI) calcd for $C_{17}H_{21}NO_3$, m/z 288.1600, found 288.1599.

(R)-tert-Butyl 3-hydroxy-2-(N-phenylaminooxy) propylcarbamate (new compound) (9j)

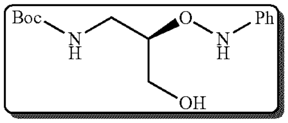

α-Aminoxy alcohol 9j was prepared according to the general procedure from tert-butyl-3-oxopropylcarbamate (0.16 mL, 0.9 mmol) to provide the title compound as a pale yellow liquid (67.2 mg, 79% yield) after flash column chromatography on silica gel (hexane/EtOAc=9/1~7/3).

$^1$H NMR (400 MHz, $CDCl_3$): δ 7.32-7.24 (3H, m), 6.98-6.94 (2H, m), 5.02 (1H, brs), 3.94-3.92 (1H, m), 3.80 (2H, s), 3.50-3.36 (2H, m), 1.45 (9H, s).

$^{13}$C NMR (100 MHz, $CDCl_3$): 157.1, 148.3, 129.0, 122.4, 114.6, 82.4, 80.0, 61.3, 39.6, 28.3.

HPLC: Chiralpak OJ-H (hexane/i-PrOH, 95/5, flow rate 1 mL/min, λ=230 nm), $t_R$ (minor)=24.8 min, $t_R$ (major)=26.6 min; 93% ee.

$[\alpha]_D^{22}$=−8.2 (c=1.3, $CHCl_3$).

HRMS (ESI) calcd for $C_{14}H_{23}N_2O_4$, m/z 282.1658, found 282.1659.

(R)-2-(p-Toluidinooxy)propan-1-ol (new compound) (9k)

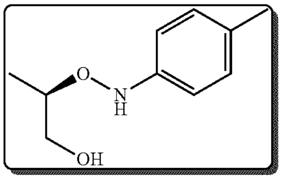

α-Aminoxy alcohol 9k was prepared according to the general procedure from propanal (0.07 mL, 0.9 mmol) and nitrosotoluene (36.3 mg, 0.3 mmol) to provide the title compound as a pale yellow liquid (45.0 mg, 83% yield) after flash column chromatography on silica gel (hexane/EtOAc=9/1~7/3).

$^1H$ NMR (400 MHz, $CDCl_3$): δ 7.07 (2H, d, J=8.1 Hz), 6.99 (1H, brs), 6.88 (2H, d, J=8.3 Hz), 4.13-4.07 (1H, m), 3.78-3.68 (2H, m), 2.28 (3H, s), 1.22 (3H, d, J=6.5 Hz).

$^{13}C$ NMR (100 MHz, $CDCl_3$): 145.8, 132.0, 129.5, 115.3 79.8, 66.6, 20.6, 15.4.

HPLC: Chiralpak AD-H (hexane/i-PrOH, 90/10, flow rate 1 mL/min, λ=230 nm), $t_R$ (minor)=10.9 min, $t_R$ (major)=12.4 min; 97% ee.

$[\alpha]_D^{25}$=+5.5 (c=1.5, $CHCl_3$).

HRMS (ESI) calcd for $C_{10}H_{16}NO_2$, m/z 182.1181, found 182.1181.

EXAMPLE 2

Formation of Functionalized Tetrahydro-1,2-oxazines via α-Aminoxylation of Aldehydes and Aza-Michael Reaction Nitroalkenes are among the most reactive Michael acceptors (for a review, see: Berner, OM, et al., Eur. J. Org. Chem. (2002) 1877-1894), so investigations were started by using 31a under the previously established conditions (Zhong, G, Angew. Chem. Int. Ed. (2003) 42, 4247-4250) (nitroalkenal 31a (1.5 equiv), nitrosobenzene (1.0 equiv), and 1-proline (20 mol %) in DMSO). The domino strategy was facile at room temperature and was complete within 30 minutes (FIG. 8). The course of the reaction was easily monitored by observing the change in the colour of the solution from green to orange. After the workup, pure tetrahydro-1,2-oxazine (THO) 33a was isolated in 46% yield with 99% enantiomeric excess (ee) and a diastereomeric ratio (d.r.) greater than 99:1 (FIG. 8, entry 1). This reaction led to the first successful isolation of a stable aldehyde after the α-aminoxylation, and the rare case of an inactivated amine undergoing a conjugate addition with an aliphatic nitroalkene with high stereoinduction (for selected examples of diaseteroselective aza-Michael additions to nitroalkenes, see: a) P. L. Southwick, J. E. Anderson, J. Am. Chem. Soc. (1957) 79, 6222-6229; b) A. Kamimura, A. Kadowaki, Y. Nagata, H. Uno, Tetrahedron Lett. (2006) 47, 2471-2473; c) D. Enders, J. Wiedemann, Synthesis (1996) 1443-1450; d) D. Lucent, P. Heyse, A. Gissot, T. Le Gall, C. Mioskowski, Eur. J. Org. Chem. (2000) 3575-3579). A preliminary screening indicated that the catalytic activity and the asymmetric induction were dependent on the solvent. Excellent enantio- and diastereoselectivities were obtained in polar, protophilic solvents, such as DMSO and DMF (FIG. 8, entries 1 and 2). A halogenated solvent possessing a lower polarity was also tolerated (FIG. 8, entry 4), whereas an ethereal solvent (THF) and water had deleterious effects on the reactivity (FIG. 8, entries 5 and 6).

Among the solvents tested, polar, protophobic acetonitrile was found to be best with respect to the chemical yield and optical purity (FIG. 8, entry 3). It is also noteworthy that although IXa proved to be an excellent catalyst in the aminoxylation, pyrrolidine-based tetrazole IXb (a) N. Momiyama, H. Torii, S. Saito, H. Yamamoto, Proc. Natl. Acad. Sci. USA (2004) 101, 5374-5378; b) A. J. A. Cobb, D. A. Longbottom, D. M. Shaw, S. V. Ley, Chem. Commun. (2004) 1808-1809; c) A. Hartikka, P. I. Arvidsson, Tetrahedron: Asymmetry (2004) 15, 1831-1834) induced reaction with lower conversion (FIG. 8, entry 7). Performing the reaction with a larger excess of 31a led to complete conversion, and 33a was isolated in 59% yield (FIG. 8, entry 8). The temperature effect on the transformation was also examined. Notably, considerable side reactions can be detected at 0° C. (FIG. 8, entry 9), but suppression of the homodimerization was accomplished at −20° C. (FIG. 8, entry 10). To avoid making intractable byproducts, the reaction mixture was diluted (FIG. 8, entry 11).

Next, the effect of the catalyst loading was evaluated. Remarkably, in the presence of tetraethylammonium bromide (TEAB) (FIG. 8, entry 12) (The addition of a phase transfer catalyst (PTC) such as TEAB greatly enhanced the solubility of L-proline, which helped to make a homogeneous solution; this increase in the catalyst concentration resulted in a positive effect on reactivity of the substrates.) a catalyst loading as low as 0.5 mol % could be used without any loss in the ee values or the d.r. numbers (FIG. 8, entry 14). For operational convenience 5 mol % 1-proline, under otherwise identical reaction times, ensured high levels of reaction efficiency and enantioselectivity (FIG. 8, entry 13). Notably, after the in situ reduction, the d.r. of the corresponding alcohol significantly dropped to 90:10 (FIG. 8, entry 15), albeit the ee value was not affected. This result implied that 1-proline played an important role in diastereocontrol.

Figure 9:
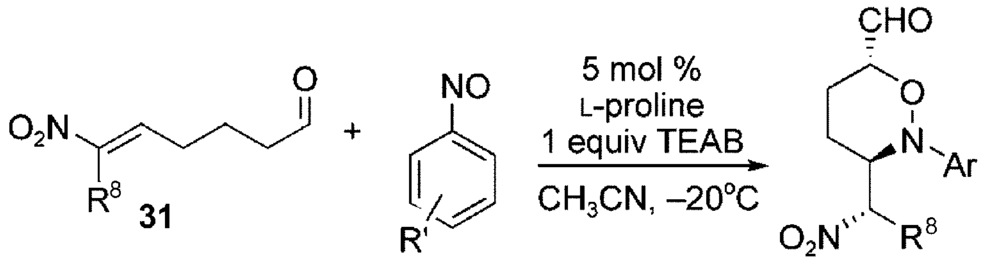
FIG. 9 illustrates an analysis of the substrate scope of the organocatalytic domino α-aminoxylation/aza-Michael reactions. Reaction conditions: 2a (1.0 equiv; 0.1m), 31a (3.0 equiv), TEAB (1.0 equiv), and IXa (5 mol %) at −20° C. in $CH_3CN$. a: Yield of isolated product. b: Determined by chiral HPLC analysis. c: Determined by $^1H$ NMR methods.

The scope of these transformations was furthermore explored by using the optimized reaction conditions. The method was applied to a variety of nitroalkenal substrates, and as shown in FIG. 9 different substituents were well-tolerated at the a position to the nitro group. The $R^8$ group of component 31 ranges from simple to sterically demanding groups, as well as valuable functional groups. Good yields were observed although there was some fluctuation depending on the substituents. The variation of the steric effects (FIG. 9, entries 4 -8) or the electronic effects (FIG. 9, entries 9-16) had only a small impact on the introduction of the third chiral center, which was evidenced by the uniformly high ee and d.r. values. Furthermore, this method was applicable to various aromatic nitroso compounds; for example, 2-methyl-, 4-methyl- and 4-bromo-nitrosobenzene (FIG. 9, entries 2, 3, and 17). The fact that the $R^8$ and R' groups of precursors 31 and 2, respectively, can be varied demonstrates the versatility of the approach of the invention.

This domino reaction generates up to three stereogenic centers and forms only one out of eight possible stereoisomers. The origin of the high stereoselectivity derives from the α-aminoxylation reaction, which is known to proceed with high enantioselectivity (For mechanistic studies, see: a) S. P. Mathew, H. Iwamura, D. G. Blackmond, Angew. Chem.

Figure 10:
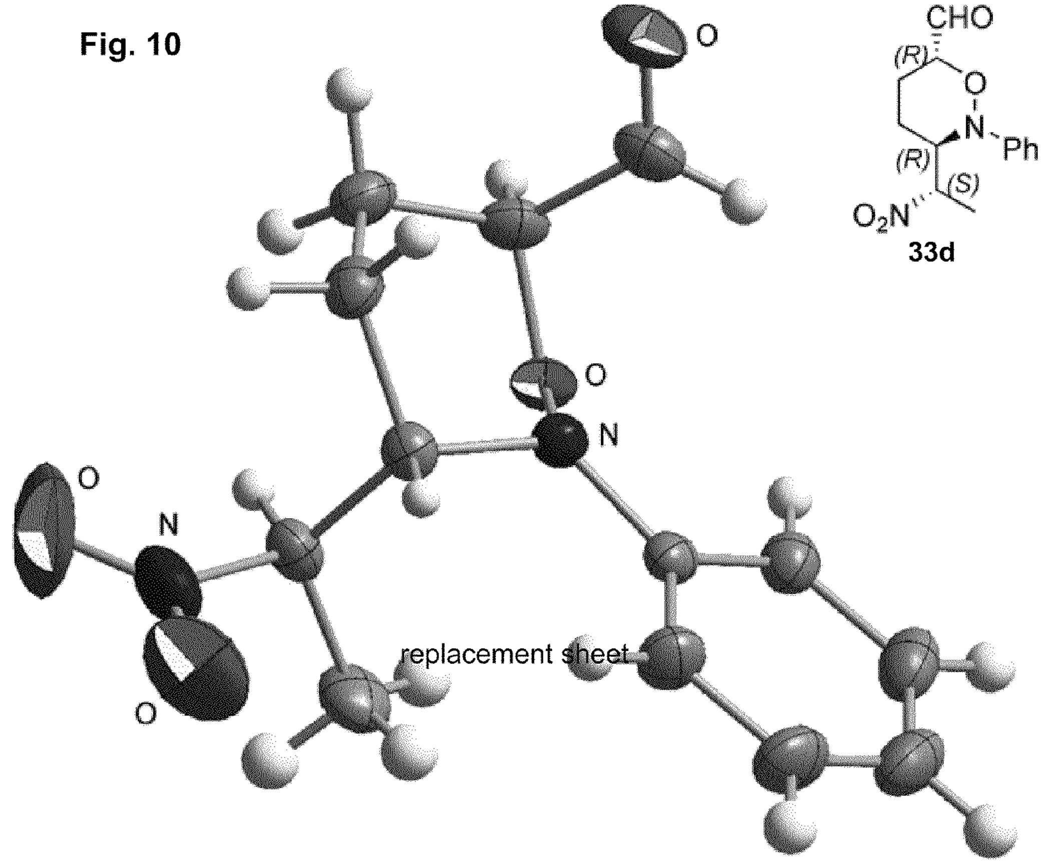
FIGS. 10 shows the X-ray crystal structure of 33d. The crystal structure has been deposited at the Cambridge Crystallographic Data Centre and allocated the deposition number: CCDC 670447.

(2004) 116, 3379-3383; Angew. Chem. Int. Ed. (2004) 43, 3317-3321; b) P. H.-Y. Cheong, K. N. Houk, J. Am. Chem. Soc. (2004) 126, 13912-13913; c) H. Iwamura, D. H. Wells, Jr., S. P. Mathew, M. Klussmann, A. Armstrong, D. G. Blackmond, J. Am. Chem. Soc. (2004) 126, 16312-16313.). This selectivity is maintained in the second step by going through a sterically favored transition state (see below). The relative and absolute configurations of THO 33d were determined by $^{1}$H NMR nuclear Overhauser effect (NOE) experiments and X-ray crystallography (FIG. 10) and compared with respective related α-aminoxylations Mathew et al., 2004, supra; Cheong et al., 2004, supra; Iwamura et al., 2004, supra; CCDC 670447 (33d) contains the supplemantary crystallographic data. These data can be obtained free of charge from The Cambdridge Crystallographic Data Center via www.ccdc.cam.ac.uk/data request/cif. The X-ray crystal structure of 33d showed the relative configuration. The absolute configuration was assigned for the α-aminoxy carbon center as R based on previous reports and mechanism studies.).

Figure 11:
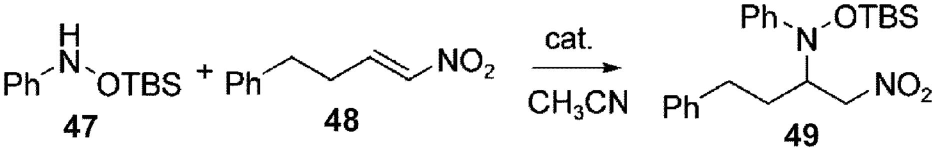
FIG. 11 depicts data of preliminary mechanistic investigations on the catalysis of the aza-Michael addition step. Reaction conditions: 47 (1.0 equiv, 0.1m), 48 (1.0 equiv), and the corresponding catalyst at room temperature in $CH_3CN$. a: Determined by $^1H$ NMR methods. TBS=tert-butyldimethylsilyl; n.r.=no reaction.

Since the aldehyde group and the a-methylnitro group are trans and pointing away from each other in the crystal structure of 33d, it is unlikely that 1-proline participates in the reaction by covalent bond catalysis in the transition state of the aza-Michael addition/protonation step. To get some mechanistic insight into this domino reaction, a series of control experiments were carried out (FIG. 11). We chose O-(tert-butyldimethylsilyl)-N-phenylhydroxylamine (47) and (E)-(4-nitrobut-3-enyl)benzene (48) as mimics of the in situ generated amine substrate and the nitroalkenyl reactant, respectively. In the absence of any catalyst, the reaction did not proceed after 2 days at −20° C. (FIG. 11, entry 1). Elevating the temperature to room temperature provided similar results (FIG. 11, entry 2), and when 1 equivalent of TEA was used as a Lewis base in the reaction it proceeded sluggishly with a 31% conversion. This experiment revealed that the tertiary amine itself was not sufficient to enhance the reactivity of 47 (FIG. 11, entry 3). The introduction of a hydrogen-bond donor (For selected recent reviews on hydrogen-bonding catalysis, see: a) A. D. Doyle, E. N. Jacobsen, Chem. Rev. 2007, 107, 5713-5743; b) P. R. Schreiner, Chem. Soc. Rev. 2003, 32, 289-296; c) P. M. Pihko, Angew. Chem. Int. Ed. (2004) 43, 2062-2064; d) Y. Takemoto, Org. Biomol. Chem. (2005) 3, 4299-4306; e) C. Bolm, T. Rantanen, I. Schiffers, L. Zani, Angew. Chem. Int. Ed. (2005) 44, 1758-1763; f) T. Akiyama, Chem. Rev. (2007) 107, 5744-5758; g) M. S. Taylor, E. N. Jacobsen, Angew. Chem. Int. Ed. 2006, 45, 1520-1543; h) S. J. Connon, Angew. Chem. Int. Ed. (2006) 45, 3909-3912; i) T. Marcelli, J. H. van Maarseveen, H. Hiemstra, Angew. Chem. Int. Ed. (2006) 45, 7496-7504), 20 mol % of quinine, resulted in full conversion within 18 hours. These observations indicate that the aza-Michael addition step is catalyzed by hydrogen-bonding interactions. Combined with the fact that intermediates cannot be detected in the $^{1}$H NMR spectra recorded during the course of the reaction or upon product isolation, a concerted mechanism is proposed. After the α-aminoxylation step, the aza-Michael addition/protonation (For timely examples on organocatalytic asymmetric protonation, see: a) C. H. Cheon, H. Yamamoto, J. Am. Chem. Soc. (2008) 130, 9246-9247; b) D. Leow, S. Lin, S. K. Chittimalla, X. Fu, C.-H. Tan, Angew. Chem. Int. Ed. (2008) 47, 5641-5645) proceeds in a synergistic way and is assisted by a molecule of water which participates in two hydrogen bonds; the hydrogen bonds are formed between the water molecule and both the in situ generated amine moiety and the nitro group (FIG. 12A). DFT calculations of the lowest energy transition state also confirm this assumption.

In summary, a novel, practical, and enantio- and diastereoselective domino reaction is provided for the synthesis of functionalized THOs, based on the use of a simple amine catalyst. The results disclosed herein demonstrate the ability to control the regio- and stereochemistry of the reaction for the synthesis of THOs from acyclic substrates. It is expected that α-aminoxylation directed domino reactions will have great potential in the field of organocatalysis. The reaction, which is easy to perform, proceeds cleanly with complete stereocontrol and does not require a change in the reaction conditions or adding reagents. This invention is likely to be used in synthetic applications, especially since the α-aminoxylation reaction can be combined with existing domino methods. Applications of this methodology to total syntheses and detailed mechanistic studies will be described in due course.

General Experimental Information

Analytical thin layer chromatography (TLC) was performed using Merck 60 F254 precoated silica gel plate (0.2 mm thickness). Subsequent to elution, plates were visualized using UV radiation (254 nm) on Spectroline Model ENF-24061/F 254 nm. Further visualization was possible by staining with basic solution of potassium permanganate or acidic solution of ceric molybdate.

Flash chromatography (FC) was performed using Merck silica gel 60 with freshly distilled solvents. Columns were typically packed as slurry and equilibrated with the appropriate solvent system prior to use.

$^{1}$H and $^{13}$C NMR spectra were recorded on Bruker AMX 300, 400 and 500 spectrophotometers at ambient temperature as noted. Chemical shifts for $^{1}$H NMR spectra are reported as 6 in units of parts per million (ppm) downfield from $SiMe_4$ (δ 0.0) and relative to the signal of chloroform-d (δ 7.2600, singlet). Multiplicities were given as: s (singlet), d (doublet), t (triplet), dd (doublets of doublet) or m (multiplets). The number of protons (n) for a given resonance is indicated by nH. Coupling constants are reported as a J value in Hz. Data for $^{13}$C NMR are reported as 6 in ppm downfield from $SiMe_4$ (δ 0.0) and relative to the signal of chloroform-d (δ 77.00, triplet).

Enantioselectivities were determined by High performance liquid chromatography (HPLC) analysis employing a Daicel Chirapak AS-H column. Optical rotations were measured in $CHCl_3$ on a Schmidt+Haensch polarimeter (Polartronic MH8) with a 10 cm cell (c given in g/100 mL). Absolute configuration of the products was determined by comparison with compounds previously published.

High resolution mass spectrometry (HRMS) was recorded on Finnigan MAT 95×P spectrometer.

Nitroalkanes 112a-c, nitrosobenzene 2a, 2-nitrosotoluene 2b, D,L- and L-proline were purchased from Sigma-Aldrich of highest purity and used without further purification. 5,5-Dimethoxypentanal 131, Nitroalkanes 112d-g, 1-bromo-4-nitrosobenzene 2c and 4-nitrosotoluene 2d were prepared according to literature procedures [for the preparation of 5,5-dimethoxypentanal 131, see: Aggarwal, V K, et al., *Org. Lett.* (2002) 4, 1227; for the preparation of nitroalkane 31d, see: Kornblum, N, & Weaver, W M, *J. Am. Chem. Soc.* (1958) 80, 4333; for the preparation of nitroalkane 31e-g, see: Kodukulla, RPK, et al., *Synth. Commun.* (1994) 24, 819; for the preparation of 1-bromo-4-nitrosobenzene 2c and 4-nitrosotoluene 2d, see: Defoin, A, *Synthesis* (2004) 706]. The racemic products used to determine the e.e. values were synthesized using D,L-proline as catalyst.

Typical Procedure for the Preparation of Nitroalkenals

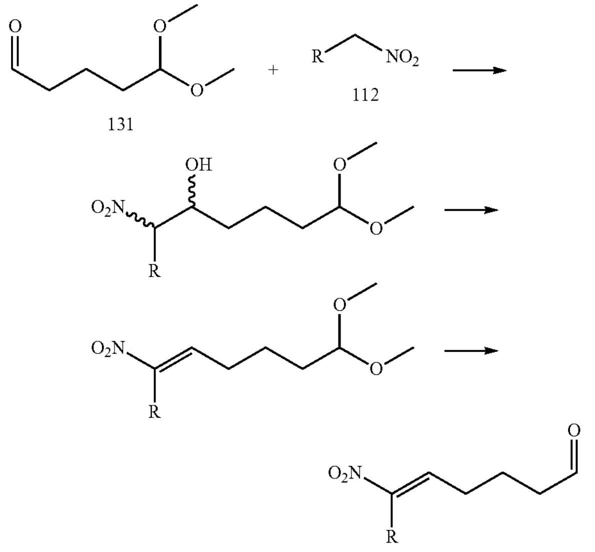

131 112 31

Procedure A

A mixture of the corresponding nitroalkane 112 (80.0 mmol), aldehyde 131 (16.0 mmol) and triethylamine (3.2 mmol) was stirred at 0° C. for 30 min and allowed to reach room temperature (r.t.) for 6-24 h. The volatiles were removed by evaporation in vacuo. The nitroaldol thus obtained as a mixture of diastereomers was dissolved in anhydrous dichloromethane (32 mL) and cooled to −70° C. Methanesulfonyl chloride (19.0 mmol) was added dropwise followed by dropwise addition of a solution of N,N-diisopropylethylamine (39.0 mmol) in anhydrous dichloromethane (8 mL), keeping the reaction mixture below −60° C. The mixture was stirred at −70° C. for 2-3 h and then allowed to reach r.t. The solution was washed with water, HCl 1N (a.q) and brine, dried over anhydrous $Na_2SO_4$ and evaporated in vacuo. The crude nitroalkene was dissolved in THF (60 mL) at 0° C., followed by addition of HCl 2N (15 mL, a.q.).

The solution was stirred at 0° C. for 30 min and allowed to reach r.t. for 6-8 h. The mixture was extracted with $Et_2O$. The organic phase was combined, washed with saturated $NaHCO_3$ (a.q.), brine, and dried over anhydrous $Na_2SO_4$. The volatiles were evaporated in vacuo and the crude nitroalkenal was purified by FC (EtOAc/Hexane) to give the pure product 31 as exclusively E isomer.

Procedure B

To a stirred solution of tetra-n-butylammonium fluoride (TBAF) (1M in THF, 22.0 mmol) in THF (300 mL) at 0° C., was added the corresponding nitroalkane 112 (24.0 mmol) in THF (40 mL) and, after 5 min, a solution of aldehyde 131 (16.0 mmol) in THF (80 mL). After stirring at 0° C. for 0.5-4 h, the mixture was poured onto saturated $NaHCO_3$ (a.q.) and extracted with $Et_2O$. The organic extracts were then washed with brine, dried over anhydrous $Na_2SO_4$, filtered through a short plug of Celite and evaporated in vacuo. The nitroaldol thus obtained as a mixture of diastereomers was dissolved in anhydrous dichloromethane (32 mL) and cooled to −50° C. Tri-fluoroacetic anhydride (16.0 mmol) was added dropwise followed by dropwise addition of a solution of N,N-diisopropylethylamine (24.0 mmol) in anhydrous dichloromethane (8 mL), keeping the reaction mixture below −40° C. After the mixture was stirred at −50° C. for 3-4 h, a solution of 1,8-diazabicycloundec-7-ene (DBU) (16.0 mmol) in anhydrous dichloromethane (8 mL) was added in one portion and the reaction mixture was allowed to reach r.t. The solution was washed with water, HCl 1N (a.q) and brine, dried over anhydrous $Na_2SO_4$ and evaporated in vacuo. The crude nitroalkene was dissolved in THF (40 mL) at 0° C., followed by addition of HCl 2N (10 mL, a.q.). The solution was stirred at 0° C. for 30 min and allowed to reach r.t. for 6-8 h. The mixture was extracted with $Et_2O$. The organic phase was combined, washed with saturated $NaHCO_3$ (a.q.), brine, and dried over anhydrous $Na_2SO_4$. The volatiles were evaporated in vacuo and the crude nitroalkenal was purified by FC (EtOAc/Hexane) to give the pure product 31 as exclusively E isomer except 31d.

(E)-6-nitrohex-5-enal 31a

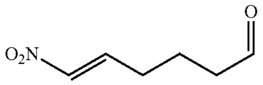

31a

Prepared according to the general procedure A from nitromethane 112a (80 mmol) and 5,5-dimethoxypentanal 131 (16 mmol) to provide the title compound as yellow oil (1.51 g, 66% yield) after silica gel chromatography (EtOAc/Hexane).

$^1H$ NMR (400 MHz, $CDCl_3$): δ 9.81 (s, 1H, CHO), 7.29-7.22 (m, 1H, $CH{=}CHNO_2$), 7.01 (d, J=13.6 Hz, 1H, $CHNO_2$), 2.57 (t, J=7.2 Hz, 2H, $CH_2CHO$), 2.35 (q, J=7.2 Hz, 2H, $CH_2CH$), 1.88 (m, 2H, $CH_2CH_2CH_2$).

$^{13}C$ NMR (100 MHz, $CDCl_3$): δ 200.8, 141.2, 141.1, 42.7, 27.6, 20.0.

(E)-6-nitrohept-5-enal 31b

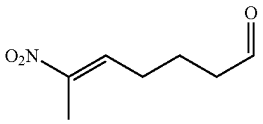

31b

Prepared according to the general procedure A from nitroethane 112b (80 mmol) and 5,5-dimethoxypentanal 131 (16 mmol) to provide the title compound as yellow oil (1.58 g, 63% yield) after silica gel chromatography (EtOAc/Hexane).

$^1H$ NMR (400 MHz, $CDCl_3$): δ 9.81 (s, 1H, CHO), 7.11 (t, J=8.0 Hz, 1H, $CH{=}C(CH_3)NO2$), 2.56 (t, J=7.2 Hz, 2H, $CH_2CHO$), 2.30 (q, J=7.2 Hz, 2H, $CH_2CH$), 2.18 (s, 3H, $CH_3$), 1.87 (m, 2H, $CH_2CH_2CH_2$).

$^{13}C$ NMR (100 MHz, $CDCl_3$): δ 201.1, 148.4, 134.6, 42.9, 27.2, 20.7, 12.5.

(E)-6-nitrooct-5-enal 31C

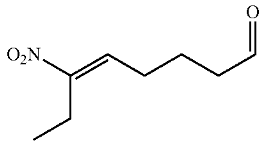

31c

Prepared according to the general procedure A from 1-nitropropane 112c (80 mmol) and 5,5-dimethoxypentanal 131 (16 mmol) to provide the title compound as yellow oil (1.51 g, 55% yield) after silica gel chromatography (EtOAc/Hexane).

$^1H$ NMR (400 MHz, $CDCl_3$): δ 9.82 (s, 1H, CHO), 7.03 (t, J=8.0 Hz, 1H, $CH{=}C(C_2H_5)NO_2$), 2.65-2.54 (m, 4H, $CH_2CHO+CH_2CH_3$), 2.30 (q, J=7.2 Hz, 2H, $CH_2CH$), 1.87 (m, 2H, $CH_2CH_2CH_2$), 1.13 (t, J=7.6 Hz, 3H, $CH_2CH_3$).

$^{13}C$ NMR (100 MHz, $CDCl_3$): δ 201.1, 153.9, 134.2, 42.9, 26.9, 20.9, 19.9, 12.7.

6-nitro-6-phenylhex-5-enal 31d

31d

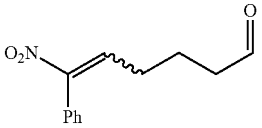

Prepared according to the general procedure B from 1-(nitromethyl)benzene 112d (24 mmol) and 5,5-dimethoxypentanal 131 (16 mmol) to provide the title compound as yellow oil (E/Z=6.7/1) (1.44 g, 41% yield) after silica gel chromatography (EtOAc/Hexane).

$^1H$ NMR (400 MHz, $CDCl_3$): δ 9.83-9.74 (1H, CHO), 7.49-7.26 (m, 5.13H, $ArH+CH{=}C(Ph)NO_2$ (E)), 6.03 (t, J=7.6 Hz, 0.87H, $CH{=}C(Ph)NO_2$(Z)), 2.63-2.46 (m, 2H, $CH_2CHO$), 2.43-2.17 (m, 2H, $CH_2CH$), 1.95-1.82 (m, 2H, $CH_2CH_2CH_2$).

$^{13}C$ NMR (100 MHz, $CDCl_3$): δ 201.4, 153.2, 131.2, 130.3, 129.8, 128.9, 128.6, 126.7, 126.3, 43.0, 27.7, 22.1, 21.0.

(E)-6-nitro-7-phenylhept-5-enal 31e

31e

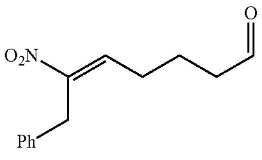

Prepared according to the general procedure B from 1-(2-nitroethyl)benzene 112e (24 mmol) and 5,5-dimethoxypentanal 131 (16 mmol) to provide the title compound as yellow oil (1.49 g, 40% yield) after silica gel chromatography (EtOAc/Hexane).

$^1H$ NMR (400 MHz, $CDCl_3$): δ 9.77 (t, J=2 Hz, 1H, CHO), 7.34-7.18 (m, 6H, $ArH+CH{=}C(CH_2)NO_2$), 3.99 (s, 2H, $CH_2Ph$), 2.56-2.52 (m, 2H, $CH_2CHO$), 2.41 (q, J=7.6 Hz, 2H, $CH_2CH$), 1.92-1.84 (m, 2H, $CH_2CH_2CH_2$).

$^{13}C$ NMR (100 MHz, $CDCl_3$): δ 201.0, 151.0, 136.3, 136.2, 128.8, 128.0, 127.0, 42.9, 32.0, 27.4, 20.8.

(E)-6-nitro-7-p-tolylhept-5-enal 31f

31f

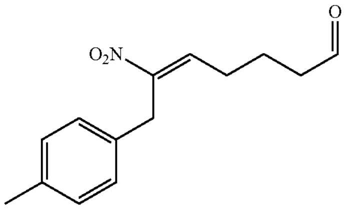

Prepared according to the general procedure B from 1-methyl-4-(2-nitroethyl)benzene 112f (24 mmol) and 5,5-dimethoxypentanal 131 (16 mmol) to provide the title compound as yellow oil (1.38 g, 35% yield) after silica gel chromatography (EtOAc/Hexane).

$^1H$ NMR (400 MHz, $CDCl_3$): δ 9.77 (s, 1H, CHO), 7.24-7.07 (m, 5H, $ArH+CH{=}C(CH_2)NO_2$), 3.95 (s, 2H, $CH_2Ar$), 2.53 (t, J=7H, $CH_2CHO$), 2.39 (q, J=7.2 Hz, 2H, $CH_2CH$), 2.33 (s, 1H, $CH_3Ar$), 1.91-1.83 (m, 2H, $CH_2CH_2CH_2$).

$^{13}C$ NMR (100 MHz, $CDCl_3$): δ 201.1, 151.2, 136.6, 136.1, 133.3, 129.4, 127.9, 42.9, 31.6, 27.4, 21.0, 20.8.

(E)-7-(4-chlorophenyl)-6-nitrohept-5-enal 31g

31g

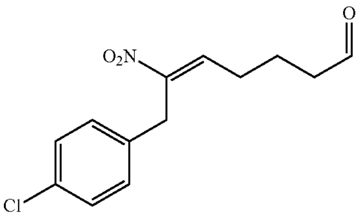

Prepared according to the general procedure B from 1-chloro-4-(2-nitroethyl)benzene 112g (24 mmol) and 5,5-dimethoxypentanal 131 (16 mmol) to provide the title compound as yellow oil (1.93 g, 45% yield) after silica gel chromatography (EtOAc/Hexane).

$^1H$ NMR (400 MHz, $CDCl_3$): δ 9.79 (s, 1H, CHO), 7.29-7.12 (m, 5H, $ArH+CH{=}C(CH_2)NO_2$), 3.95 (s, 2H, $CH_2Ar$), 2.56 (m, 2H, $CH_2CHO$), 2.41 (q, J=7.7 Hz, 2H, $CH_2CH$), 1.93-1.83 (m, 2H, $CH_2CH_2CH_2$).

$^{13}C$ NMR (100 MHz, $CDCl_3$): δ 200.8, 150.6, 136.5, 134.8, 132.9, 129.4, 128.9, 42.9, 31.4, 27.4, 20.8.

(E)-7-(4-bromophenyl)-6-nitrohept-5-enal 31h

31h

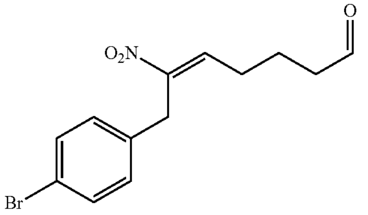

Prepared according to the general procedure B from 1-bromo-4-(2-nitroethyl)benzene 112h (24 mmol) and 5,5-dimethoxypentanal 131 (16 mmol) to provide the title compound as yellow oil (2.15 g, 43% yield) after silica gel chromatography (EtOAc/Hexane).

$^1$H NMR (300 MHz, $CDCl_3$): δ 9.79 (s, 1H, CHO), 7.49-7.06 (m, 5H, ArH+CH═C($CH_2$)$NO_2$), 3.92 (s, 2H, CHAr), 2.57 (t, J=7.0 Hz, 2H, $CH_2$CHO), 2.41 (q, J=7.5 Hz, 2H, $CH_2$CH), 1.93-1.84 (m, 2H, $CH_2CH_2CH_2$).

$^{13}$C NMR (75 MHz, $CDCl_3$): δ 200.9, 150.5, 136.6, 135.3, 131.9, 129.8, 120.9, 42.9, 31.5, 27.4, 20.8.

General Procedure for Domino Aminoxylation/Michael Reaction

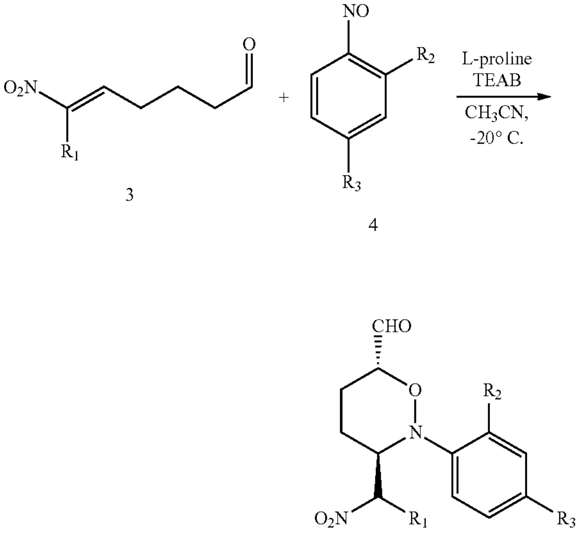

3 4 5

To a 25 mL vial equipped with a magnetic stir bar and charged with tetraethyl-ammonium bromide (TEAB) (105 mg, 0.5 mmol) was added $CH_3CN$ (5.0 mL), followed by the appropriate alkenal (1.5 mmol) and the solution was cooled to −20° C. for 10 min before nitroso-benzene (54 mg, 0.5 mmol) was added in one portion upon at which time the solution became green. To this green homogeneous solution was then added L-proline (3.0 mg, 0.025 mmol) in one portion. The resulting solution was then stirred at −20° C. until the limited reactants was fully consumed and the disappearance of green color in solution, resulting in a final yellow or orange homogeneous solution. The reaction mixture was quenched with half saturated aqueous $NH_4Cl$ solution, extracted with EtOAc, dried over anhydrous $Na_2SO_4$, filtered, and concentrated in vacuo. The resulting residue was then purified by FC (EtOAc/Hexane) to provide the title compounds.

Optimization of Reaction Conditions

1) Solvent Effect

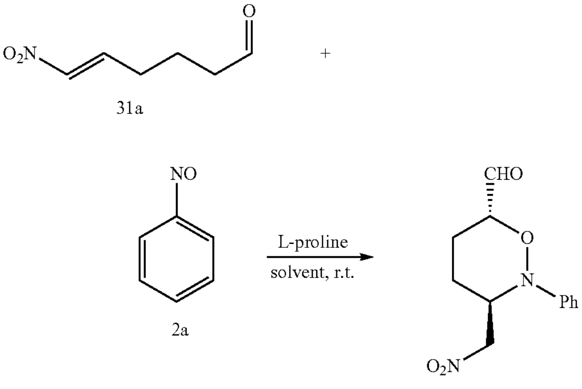

31a 2a 33a

| entry | solvent | time | % yield[b] | % e.e.[c] | d.r.[d] |
|---|---|---|---|---|---|
| 1 | DMSO | 0.5 h | 46 | 99 | >99:1 |
| 2 | DMF | 0.5 h | 44 | 99 | >99:1 |
| 3 | $CH_3CN$ | 0.5 h | 55 | 99 | >99:1 |
| 4 | $CHCl_3$ | 0.5 h | 53 | 98 | >99:1 |
| 5 | THF | 24 h | <20 | n.d. | n.d. |
| 6 | $H_2O$ | 48 h | <5 | n.d. | n.d. |
| 7 | NMP | 0.5 h | 54 | 98 | >99:1 |
| 8[e] | $CH_3CN$ | 0.5 h | 49 | 99 | >99:1 |

[a]Unless otherwise noted, reactions were conducted with 1.0 equiv of nitrosobenzene 2a (1M), 1.5 equiv of nitroalkenal 31a and 20 mol % L-proline at room temperature.

[b]Isolated yield.

[c]Determined by chiral HPLC analysis (Chiralcel AS—H).

[d]Determined by $^1$H NMR.

[e]Pyrrolidine-based tetrazole was used as catalyst.

The catalytic activity and asymmetric induction showed dependence on the solvent. Excellent enantio- and diastereo-selectivity could be achieved in highly polar and protophilic solvents, such as DMSO, DMF, and NMP (entries 1, 2, 7). Halogenated solvent possessing a similar but lower polarity was also tolerated (entry 4), whereas less polar ethereal solvent, such as THF and the most polar solvent water showed deleterious effect on reactivity (entries 5, 6). Among the solvents tested, the highly polar but protophobic acetonitrile was found to be the best with respect to the catalytic activity and the asymmetric induction (entry 3). In addition, it is also noteworthy that although proved to be an excellent catalyst in aminoxylation, pyrrolidine-based tetrazole induced reaction with lower conversion (entry 8).

2) Temperature Effect

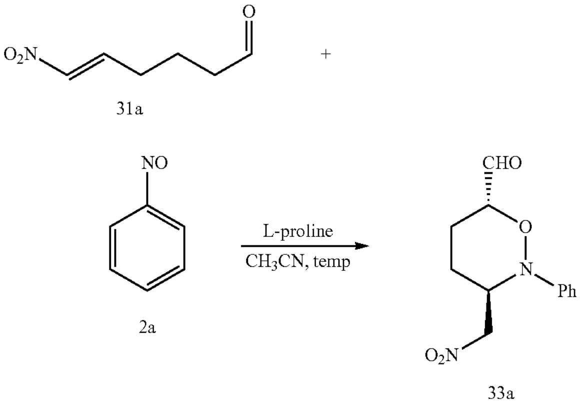

31a

2a

33a

| entry | temperature | time | % yield[b] | % e.e.[c] | d.r.[d] |
|---|---|---|---|---|---|
| 1 | r.t. | 0.5 h | 55 | 99 | >99:1 |
| 2 | 0° C. | 0.5 h | 59 | 99 | >99:1 |
| 3 | −20° C. | 1 h | 63 | >99 | >99:1 |
| 4[e] | −20° C. | 1 h | 67 | >99 | >99:1 |
| 5[e] | −40° C. | 4 h | 53 | >99 | >99:1 |
| 6[e] | −60° C. | 48 h | <5 | n.d. | n.d. |

[a]Unless otherwise noted, reactions were conducted with 1.0 equiv of nitrosobenzene 2a (1M), 1.5 equiv of nitroalkenal 31a and 20 mol % L-proline in $CH_3CN$.

[b]Isolated yield.

[c]Determined by chiral HPLC analysis (Chiralcel AS—H).

[d]Determined by $^1H$ NMR.

[e]3.0 equiv of 31a was used.

Considerable side reactions were detected when the reaction was conducted at r.t. or at 0° C. (entries 1, 2). Suppression of the homodimerization byproducts was accomplished at −20° C. (entry 3), while further lowering the temperature imparted a detrimental influence on reaction efficiency (entries 5, 6). Implementing excess of nitroalkenal 31a also contributed to higher chemical yield (entry 3 vs entry 4).

3) Concentration Effect

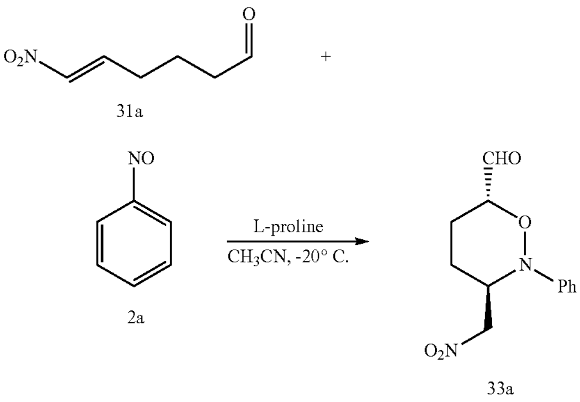

31a

2a

33a

| entry | concentration of 4a | time | % yield[b] | % e.e.[c] | d.r.[d] |
|---|---|---|---|---|---|
| 1 | 1M | 1 h | 67 | >99 | >99:1 |
| 2 | 0.5M | 4 h | 69 | >99 | >99:1 |
| 3 | 0.2M | 14 h | 71 | >99 | >99:1 |
| 4 | 0.1M | 24 h | 73 | >99 | >99:1 |
| 5 | 0.05M | 48 h | 70 | >99 | >99:1 |

-continued

[a]Unless otherwise noted, reactions were conducted with 1.0 equiv of nitrosobenzene 2a, 3.0 equiv of nitroalkenal 31a and 20 mol % L-proline in $CH_3CN$ at −20° C.

[b]Isolated yield.

[c]Determined by chiral HPLC analysis (Chiralcel AS—H).

[d]Determined by $^1H$ NMR.

Results revealed that lowering the concentration from 1 M to 0.1 M extensively suppressed the homodimerization of 2a, thus improved the chemical yield of 33a (entries 1-4). However, further decreased concentration only resulted in longer reaction time (entriy 5).

4) Survey of Additives

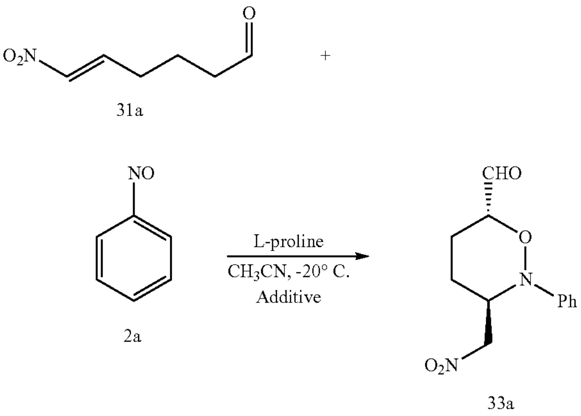

31a

2a

33a

| entry | additive | time | % yield[b] | % e.e.[c] | d.r.[d] |
|---|---|---|---|---|---|
| 1 | TEAB 0.1 eq | 22 h | 73 | >99 | >99:1 |
| 2 | TEAB 0.5 eq | 19 h | 78 | >99 | >99:1 |
| 3 | TEAB 1 eq | 14 h | 90 | >99 | >99:1 |
| 4 | TEAB 2 eq | 12 h | 89 | >99 | >99:1 |
| 5 | TBAB 1 eq | 15 h | 82 | >99 | >99:1 |
| 6 | TEAI 1 eq | 16 h | 80 | >99 | >99:1 |
| 7 | TBAI 1 eq | 16 h | 81 | >99 | >99:1 |
| 8 | none | 24 h | 73 | >99 | >99:1 |

[a]Unless otherwise noted, reactions were conducted with 1.0 equiv of nitrosobenzene 2a (0.1M), 3.0 equiv of nitroalkenal 31a and 20 mol % L-proline in $CH_3CN$ at −20° C.

[b]Isolated yield.

[c]Determined by chiral HPLC analysis (Chiralcel AS—H).

[d]Determined by $^1H$ NMR.

TBAB = tetra-n-butylammonium bromide,TEAI = tetraethylammonium iodide, TBAI = tetra-n-butyl-ammonium iodide.

The addition of phase transfer catalyst (PTC) such as TEAB greatly enhanced the solubility of L-proline which helped to make a homogeneous solution, thus presented positive effect on reactivity by increasing catalyst concentration in the reaction medium. The using of 1 equiv of TEAB was found to be the best option (entry 4), either changing it to other PTCs (entries 6-8) or using other equivalents (entries 1, 2, and 5) provided inferior results.

5) Survey of Catalyst Loading

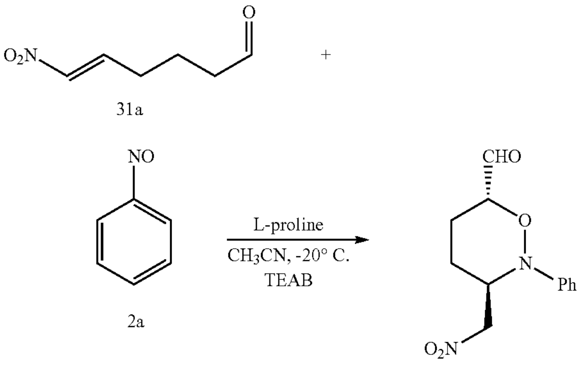

31a

2a

33a

| entry | mol % of cat. | time | % yield[b] | % e.e.[c] | d.r.[d] |
|---|---|---|---|---|---|
| 1 | 20 | 14 h | 90 | >99 | >99:1 |
| 2 | 10 | 18 h | 90 | >99 | >99:1 |
| 3 | 5 | 24 h | 90 | >99 | >99:1 |
| 4 | 1 | 30 h | 73 | >99 | >99:1 |
| 5 | 0.5 | 48 h | 65 | >99 | >99:1 |

[a]Unless otherwise noted, reactions were conducted with 1.0 equiv of nitrosobenzene 2a (0.1M), 3.0 equiv of nitroalkenal 31a, 1.0 equiv of TEAB and L-proline in $CH_3CN$ at −20° C.

[b]Isolated yield.

[c]Determined by chiral HPLC analysis (Chiralcel AS—H).

[d]Determined by $^1H$ NMR.

Next, we surveyed the catalyst loading with L-proline. Gratifyingly, we could decrease the catalyst loading to 0.5 mol % without any loss of asymmetric induction (entry 5). In terms of operational convenience, the use of 5 mol % L-proline ensures high levels of reaction efficiency and enantioselectivity while maintaining expedient reaction times (entry 3).

Substrate Scope (3R,6R)-3-(nitromethyl)-2-phenylmorpholine-6-carbaldehyde 33a

33a

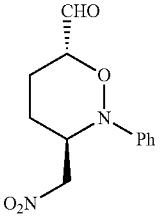

Prepared according to the general procedure from 31a (1.5 mmol) and nitrosobenzene (0.5 mmol) to provide the title compound as yellow oil (113 mg, 90% yield) after silica gel chromatography (EtOAc/Hexane).

$^1H$ NMR (500 MHz, $CDCl_3$) δ 9.75 (d, J=1.5 Hz, 1H, CHO), 7.38-7.09 (m, 5H, ArH), 4.82 (dd, J=12.5, 9.5 Hz, 1H, $CH_2NO_2$), 4.52-4.49 (m, 2H, $CH_2NO_2$+CHCHO), 4.43 (dd, J=6.7, 1.0 Hz, 1H, CHN), 2.25-2.12 (m, 2H, $CH_2CHCHO$), 2.12-2.06 (m, 2H, $CH_2CHN$).

$^{13}C$ NMR (100 MHz, $CDCl_3$): δ 202.5, 147.3, 129.4, 123.8, 115.8, 82.4, 71.8, 57.7, 21.9, 18.5.

HPLC: Chiralpak AS-H (hexane/i-PrOH, 85/15, flow rate 1 mL/min, λ=230 nm), $t_R$ (major)=15.8 min, $t_R$ (minor)=50.2 min; >99% ee.

$[\alpha]_D^{25}$=−213.7 (c=1.0, $CHCl_3$).

HRMS (EI) calcd for $C_{12}H_{14}O_4N_2$, m/z 250.0948, found 250.0944.

(3R,6R)-3-(nitromethyl)-2-o-tolylmorpholine-6-carbaldehyde 33b

33b

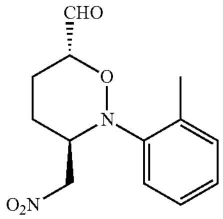

Prepared according to the general procedure from 31a (1.5 mmol) and 2-nitroso-toluene (0.5 mmol) to provide the title compound as yellow oil (105 mg, 79% yield) after silica gel chromatography (EtOAc/Hexane).

$^1H$ NMR (500 MHz, $CDCl_3$) δ 9.75 (d, J=1.0 Hz, 1H, CHO), 7.35-7.12 (m, 4H, ArH), 4.82 (m, 1H, $CH_2NO_2$), 4.61 (m, 1H, $CH_2NO_2$), 4.46 (m, 1H, CHCHO), 3.97-3.94 (m, 1H, CHN), 2.22 (s, 3H, $CH_3Ar$), 2.20-2.13 (m, 2H, $CH_2CHCHO$), 2.06-1.75 (m, 2H, $CH_2CHN$).

$^{13}C$ NMR (100 MHz, $CDCl_3$): δ 202.4, 145.8, 131.4, 126.6, 126.1, 119.9, 82.7, 71.9, 57.8, 22.8, 18.7, 17.5.

HPLC: Chiralpak AS-H (hexane/i-PrOH, 85/15, flow rate 1 mL/min, λ=220 nm), $t_R$ (major)=14.0 min, $t_R$ (minor)=16.8 min; 97% ee.

$[\alpha]_D^{25}$=−66.9 (c=0.8, $CHCl_3$).

HRMS (EI) calcd for $C_{13}H_{16}O_4N_2$, m/z 264.1105, found 264.1099.

(3R,6R)-2-(4-bromophenyl)-3-(nitromethyl)morpholine-6-carbaldehyde 33c

33c

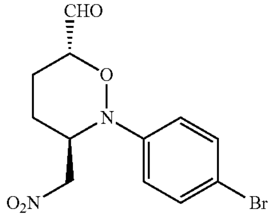

Prepared according to the general procedure from 31a (1.5 mmol) and 1-bromo-4-nitrosobenzene (0.5 mmol) to provide the title compound as yellow oil (145 mg, 88% yield) after silica gel chromatography (EtOAc/Hexane).

$^1H$ NMR (400 MHz, $CDCl_3$) δ 9.75 (s, 1H, CHO), 7.28 (dd, J=120, 8.4 Hz, 4H, ArH), 4.85-4.79 (m, 1H, $CH_2NO_2$), 4.53-4.49 (m, 2H, $CH_2NO_2$+CHCHO), 4.42 (m, 1H, CHN), 2.29-2.14 (m, 2H, $CH_2CHCHO$), 2.13-1.83 (m, 2H, $CH_2CHN$).

$^{13}C$ NMR (100 MHz, $CDCl_3$): δ 202.0, 146.4, 132.4, 117.5, 116.5, 82.5, 71.8, 57.6, 21.9, 18.4.

HPLC: Chiralpak AS-H (hexane/i-PrOH, 85/15, flow rate 1 mL/min, λ=254 nm), $t_R$ (major)=17.5 min, $t_R$ (minor)=44.9 min; >99% ee.

$[\alpha]_D^{25}$=−65.0 (c=0.8, $CHCl_3$).

HRMS (EI) calcd for $C_{12}H_{13}BrO_4N_2$, m/z 328.0053, found 328.0009; calcd for $C_{12}H_{13}BrO_4N_2$, m/z 330.0033, found 330.0031.

(3R,6R)-3-((S)-1-nitroethyl)-2-phenylmorpholine-6-carbaldehyde 33d

33d

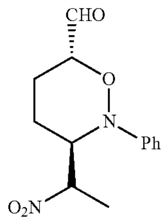

Prepared according to the general procedure from 31b (1.5 mmol) and nitrosobenzene (0.5 mmol) to provide the title compound as yellow solid (99 mg, 75% yield) after silica gel chromatography (EtOAc/Hexane).

$^1H$ NMR (500 MHz, $CDCl_3$) δ 9.66 (s, 1H, CHO), 7.37-7.01 (m, 5H, ArH), 5.38-5.33 (m, 1H, $CHNO_2$), 4.54-4.53 (m, 1H, CHCHO), 4.27-4.25 (m, 1H, CHN), 2.23-2.04 (m, 2H, $CH_2CHCHO$), 2.03-1.72 (m, 2H, $CH_2CHN$), 1.26 (d, J=7.0 Hz, 3H, $CH_3$).

$^{13}C$ NMR (100 MHz, $CDCl_3$): δ 202.7, 148.7, 129.3, 122.3, 114.1, 83.2, 82.2, 61.1, 22.7, 19.2, 18.6.

HPLC: Chiralpak AS-H (hexane/i-PrOH, 85/15, flow rate 1 mL/min, λ=230 nm), $t_R$ (major)=11.0 min, $t_R$ (minor)=20.6 min; 99% ee.

$[\alpha]_D^{25}$=−46.8 (c=1.1, $CHCl_3$)

HRMS (EI) calcd for $C_{13}H_{16}O_4N_2$, m/z 264.1105, found 264.1104.

(3R,6R)-2-(4-bromophenyl)-3-((S)-1-nitroethyl)morpholine-6-carbaldehyde 33e

33e

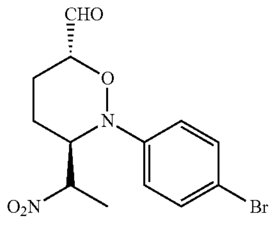

Prepared according to the general procedure from 31b (1.5 mmol) and 1-bromo-4-nitrosobenzene (0.5 mmol) to provide the title compound as yellow oil (125 mg, 73% yield) after silica gel chromatography (EtOAc/Hexane).

$^1H$ NMR (400 MHz, $CDCl_3$) δ 9.63 (s, 1H, CHO), 7.24 (dd, J=115, 8.8 Hz, 4H, ArH), 5.37-5.30 (m, 1H, $CHNO_2$), 4.53 (m, 1H, CHCHO), 4.22 (m, 1H, CHN), 2.23-2.04 (m, 2H, $CH_2CHCHO$), 2.03-1.71 (m, 2H, $CH_2CHN$), 1.27 (d, J=6.8 Hz, 3H, $CH_3$).

$^{13}C$ NMR (100 MHz, $CDCl_3$): δ 202.1, 147.8, 132.2, 115.8, 114.8, 83.2, 82.1, 61.0, 22.5, 19.1, 18.7.

HPLC: Chiralpak AS-H (hexane/i-PrOH, 85/15, flow rate 1 mL/min, λ=254 nm), $t_R$ (major)=14.3 min, $t_R$ (minor)=22.9 min; 99% ee.

$[\alpha]_D^{25}$=−44.2 (c=0.7, $CHCl_3$).

HRMS (EI) calcd for $C_{13}H_{15}BrO_4N_2$, m/z 342.0210, found 342.0209; calcd for $C_{13}H_{15}BrO_4N_2$, m/z 344.0189, found 344.0194.

(3R,6R)-3-((S)-1-nitropropyl)-2-phenylmorpholine-6-carbaldehyde 33f

33f

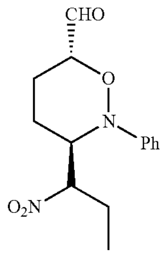

Prepared according to the general procedure from 31c (1.5 mmol) and nitrosobenzene (0.5 mmol) to provide the title compound as yellow oil (95 mg, 68% yield) after silica gel chromatography (EtOAc/Hexane).

$^1H$ NMR (400 MHz, $CDCl_3$) δ 9.66 (s, 1H, CHO), 7.37-7.00 (m, 5H, ArH), 5.21-5.15 (m, 1H, $CHNO_2$), 4.53 (m, 1H, CHCHO), 4.25 (m, 1H, CHN), 2.22-2.04 (m, 2H, $CH_2CHCHO$), 2.03-1.72 (m, 2H, $CH_2CHN$), 1.67-1.43 (m, 2H, $CH_2CH_3$), 0.81 (t, J=7.6 Hz, 3H, $CH_2CH_3$).

$^{13}C$ NMR (100 MHz, $CDCl_3$): δ 202.7, 148.6, 129.3, 122.3, 114.0, 89.1, 83.2, 60.3, 25.5, 22.7, 19.2, 10.4.

HPLC: Chiralpak AS-H (hexane/i-PrOH, 85/15, flow rate 1 mL/min, λ=230 nm), $t_R$ (major)=8.7 min, $t_R$ (minor)=16.9 min; >99% ee.

$[\alpha]_D^{25}$=−38.3 (c=0.8, $CHCl_3$).

HRMS (EI) calcd for $C_{14}H_{18}O_4N_2$, m/z 278.1261, found 278.1263.

(3R,6R)-2-(4-bromophenyl)-3-((S)-1-nitropropyl)morpholine-6-carbaldehyde 33g

33g

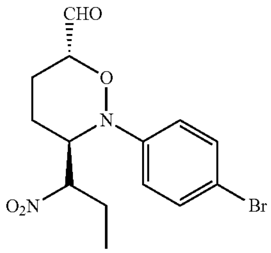

Prepared according to the general procedure from 31c (1.5 mmol) and 1-bromo-4-nitrosobenzene (0.5 mmol) to provide the title compound as yellow oil (107 mg, 60% yield) after silica gel chromatography (EtOAc/Hexane).

$^1H$ NMR (400 MHz, $CDCl_3$) δ 9.62 (s, 1H, CHO), 7.23 (dd, J=160, 9.2 Hz, 4H, ArH), 5.18-5.13 (m, 1H, $CHNO_2$), 4.53-

4.52 (m, 1H, CHCHO), 4.22-4.19 (m, 1H, CHN), 2.23-2.15 (m, 2H, $CH_2CHCHO$), 2.05-1.71 (m, 2H, $CH_2CHN$), 1.38-1.07 (m, 2H, $CH_2CH_3$), 0.83 (t, J=7.6 Hz, 3H, $CH_2CH_3$).

$^{13}C$ NMR (100 MHz, $CDCl_3$): δ 202.2, 147.9, 132.2, 115.6, 114.6, 89.0, 83.3, 60.2, 25.6, 22.6, 19.1, 10.4.

HPLC: Chiralpak AS-H (hexane/i-PrOH, 85/15, flow rate 1 mL/min, λ=254 nm), $t_R$ (major)=10.2 min, $t_R$ (minor)=18.0 min; >99% ee.

$[\alpha]_D^{25}$=−36.5 (c=0.7, $CHCl_3$).

HRMS (EI) calcd for $C_{14}H_{17}BrO_4N_2$, m/z 356.0366, found 356.0359.

(3R,6R)-3-((S)-nitro(phenyl)methyl)-2-phenylmorpholine-6-carbaldehyde 33h

33h

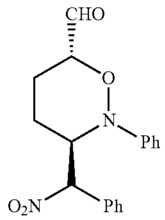

Prepared according to the general procedure from 31d (1.5 mmol) and nitrosobenzene (0.5 mmol) to provide the title compound as white solid (119 mg, 73% yield) after silica gel chromatography (EtOAc/Hexane).

$^1H$ NMR (400 MHz, $CDCl_3$) δ 9.61 (s, 1H, CHO), 7.29-6.64 (m, 10H, ArH), 6.32 (m, $CHNO_2$), 4.80-4.77 (m, 1H, CHCHO), 4.58 (m, 1H, CHN), 2.32-2.19 (m, 2H, $CH_2CHCHO$), 2.18-1.88 (m, 2H, $CH_2CHN$).

$^{13}C$ NMR (100 MHz, $CDCl_3$): δ 202.8, 148.0, 131.0, 129.6, 129.1, 128.2 128.2, 121.7, 115.0, 88.9, 83.2, 61.8, 23.3, 19.2.

HPLC: Chiralpak AS-H (hexane/i-PrOH, 85/15, flow rate 1 mL/min, λ=220 nm), $t_R$ (major)=11.9 min, $t_R$ (minor)=30.2 min; >99% ee.

$[\alpha]_D^{25}$=−66.5 (c=0.8, $CHCl_3$).

HRMS (EI) calcd for $C_{18}H_{18}O_4N_2$, m/z 326.1261, found 326.1262.

(3R,6R)-3-((S)-1-nitro-2-phenylethyl)-2-phenylmorpholine-6-carbaldehyde 33i

33i

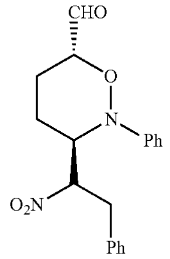

Prepared according to the general procedure from 31e (1.5 mmol) and nitrosobenzene (0.5 mmol) to provide the title compound as white solid (85 mg, 50% yield) after silica gel chromatography (EtOAc/Hexane).

$^1H$ NMR (400 MHz, $CDCl_3$) δ 9.70 (s, 1H, CHO), 7.40-6.98 (m, 10H, ArH), 5.50-5.44 (m, 1H, $CHNO_2$), 4.58-4.57 (m, 1H, CHCHO), 4.31 (m, 1H, CHN), 2.88-2.75 (m, 2H, $CH_2Ar$), 2.23-2.20 (m, 2H, $CH_2CHCHO$), 2.09-1.76 (m, 2H, $CH_2CHN$).

$^{13}C$ NMR (100 MHz, $CDCl_3$): δ 202.6, 148.6, 135.2, 129.5, 128.8, 128.5 127.5, 122.7, 114.4, 88.7, 83.2, 60.7, 38.5, 22.7, 19.2.

HPLC: Chiralpak AS-H (hexane/i-PrOH, 85/15, flow rate 1 mL/min, λ=230 nm), $t_R$ (major)=11.2 min, $t_R$ (minor)=35.2 min; >99% ee.

$[\alpha]_D^{25}$=−51.8 (c=0.7, $CHCl_3$).

HRMS (EI) calcd for $C_{19}H_{20}O_4N_2$, m/z 340.1418, found 340.1419.

(3R,6R)-2-(4-bromophenyl)-3-((S)-1-nitro-2-phenylethyl)morpholine-6-carbaldehyde 33j 33j

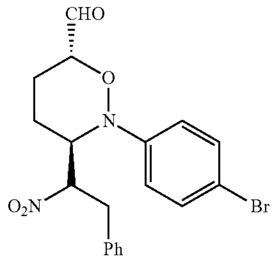

Prepared according to the general procedure from 31e (1.5 mmol) and 1-bromo-4-nitrosobenzene (0.5 mmol) to provide the title compound as white solid (138 mg, 66% yield) after silica gel chromatography (EtOAc/Hexane).

$^1H$ NMR (400 MHz, $CDCl_3$) δ 9.67 (s, 1H, CHO), 7.49-6.99 (m, 9H, ArH), 5.47-5.41 (m, 1H, $CHNO_2$), 4.58-4.56 (m, 1H, CHCHO), 4.28-4.25 (m, 1H, CHN), 2.89-2.77 (m, 2H, $CH_2Ar$), 2.23-2.19 (m, 2H, $CH_2CHCHO$), 2.11-1.78 (m, 2H, $CH_2CHN$).

$^{13}C$ NMR (100 MHz, $CDCl_3$): δ 202.0, 147.6, 134.9, 132.4, 128.9, 128.5 127.6, 116.0, 115.1, 88.5, 83.3, 60.4, 38.5, 22.4, 19.0.

HPLC: Chiralpak AS-H (hexane/i-PrOH, 85/15, flow rate 1 mL/min, λ=254 nm), $t_R$ (major)=12.4 min, $t_R$ (minor)=29.4 min; 99% ee.

$[\alpha]_D^{25}$=−31.3 (c=0.7, $CHCl_3$).

HRMS (EI) calcd for $C_{19}H_{19}BrO_4N_2$, m/z 418.0523, found 418.0521.

(3R,6R)-3-((S)-1-nitro-2-p-tolylethyl)-2-phenylmorpholine-6-carbaldehyde 33k

33k

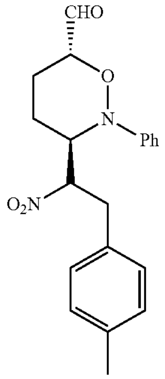

Prepared according to the general procedure from 31f (1.5 mmol) and nitrosobenzene (0.5 mmol) to provide the title compound as white solid (83 mg, 47% yield) after silica gel chromatography (EtOAc/Hexane).

$^1H$ NMR (400 MHz, $CDCl_3$) δ 9.70 (s, 1H, CHO), 7.39-6.86 (m, 9H, ArH), 5.47-5.41 (m, 1H, $CHNO_2$), 4.57 (m, 1H, CHCHO), 4.58 (m, 1H, CHN), 2.84-2.70 (m, 2H, $CH_2Ar$), 2.29 (s, 1H, $CH_3Ar$), 2.21-2.10 (m, 2H, $CH_2CHCHO$), 2.08-1.75 (m, 2H, $CH_2CHN$).

$^{13}C$ NMR (100 MHz, $CDCl_3$): δ 202.6, 148.6, 137.1, 132.1, 129.5, 128.4, 122.7 114.6, 114.4, 88.8, 83.2, 60.6, 38.1, 22.6, 21.0, 19.2.

HPLC: Chiralpak AS-H (hexane/i-PrOH, 85/15, flow rate 1 mL/min, λ=220 nm), $t_R$ (major)=10.2 min, $t_R$ (minor)=30.7 min; >99% ee.

$[\alpha]_D^{25}$=−19.3 (c=0.7, $CHCl_3$).

HRMS (EI) calcd for $C_{20}H_{22}O_4N_2$, m/z 354.1574, found 354.1578.

(3R,6R)-2-(4-bromophenyl)-3-((S)-1-nitro-2-p-tolylethyl)morpholine-6-carbaldehyde 331

331

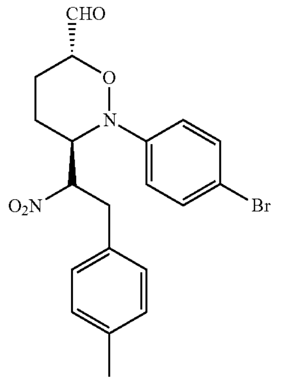

Prepared according to the general procedure from 31f (1.5 mmol) and 1-bromo-4-nitrosobenzene (0.5 mmol) to provide the title compound as white solid (97 mg, 45% yield) after silica gel chromatography (EtOAc/Hexane).

$^1H$ NMR (400 MHz, $CDCl_3$) δ 9.66 (s, 1H, CHO), 7.48-6.87 (m, 8H, ArH), 5.43-5.37 (m, 1H, $CHNO_2$), 4.57-4.55 (m, 1H, CHCHO), 4.26-4.24 (m, 1H, CHN), 2.85-2.72 (m, 2H, $CH_2Ar$), 2.30 (s, 1H, $CH_3Ar$), 2.21-2.19 (m, 2H, $CH_2CHCHO$), 2.10-1.78 (m, 2H, $CH_2CHN$).

$^{13}C$ NMR (100 MHz, $CDCl_3$): δ 202.1, 147.6, 137.3, 132.4, 131.7, 129.5 128.4, 116.0, 115.1, 88.6, 83.3, 60.4, 38.1, 22.4, 21.1, 19.0.

HPLC: Chiralpak AS-H (hexane/i-PrOH, 85/15, flow rate 1 mL/min, λ=254 nm), $t_R$ (major)=10.1 min, $t_R$ (minor)=21.9 min; >99% ee.

$[\alpha]_D^{25}$=−16.6 (c=0.6, $CHCl_3$).

HRMS (EI) calcd for $C_{20}H_{21}BrO_4N_2$, m/z 432.0679, found 432.0681.

(3R,6R)-3-((S)-2-(4-chlorophenyl)-1-nitroethyl)-2-phenylmorpholine-6-carbaldehyde 33m 33m

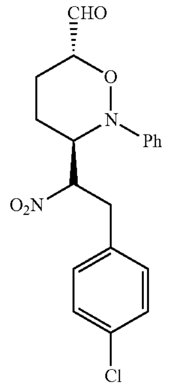

Prepared according to the general procedure from 31g (1.5 mmol) and nitrosobenzene (0.5 mmol) to provide the title compound as white solid (146 mg, 78% yield) after silica gel chromatography (EtOAc/Hexane).

$^1H$ NMR (400 MHz, $CDCl_3$) δ 9.70 (s, 1H, CHO), 7.40-6.91 (m, 9H, ArH), 5.47-5.41 (m, 1H, $CHNO_2$), 4.57 (m, 1H, CHCHO), 4.31 (m, 1H, CHN), 2.85-2.68 (m, 2H, $CH_2Ar$), 2.22-2.11 (m, 2H, $CH_2CHCHO$), 2.09-1.75 (m, 2H, $CH_2CHN$).

$^{13}C$ NMR (100 MHz, $CDCl_3$): δ 202.4, 148.5, 133.7, 133.4, 129.9, 129.5, 129.0 122.8, 114.3, 88.6, 83.2, 60.7, 37.8, 22.7, 19.1.

HPLC: Chiralpak AS-H (hexane/i-PrOH, 85/15, flow rate 1 mL/min, λ=220 nm), $t_R$ (major)=12.3 min, $t_R$ (minor)=48.2 min; >99% ee.

$[\alpha]_D^{25}$=−43.2 (c=0.7, $CHCl_3$).

HRMS (EI) calcd for $C_{19}H_{19}ClO_4N_2$, m/z 374.1028, found 374.1048; calcd for $C_{19}H_{19}{}^{37}ClO_4N_2$, m/z 376.0998, found 376.0990.

(3R,6R)-2-(4-bromophenyl)-3-((S)-2-(4-chlorophenyl)-1-nitroethyl)morpholine-6-carbaldehyde 33n 33n

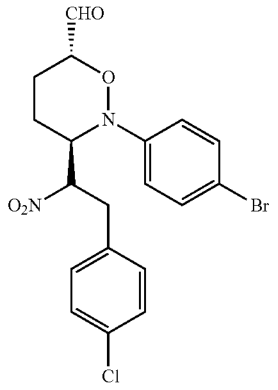

Prepared according to the general procedure from 31g (1.5 mmol) and 1-bromo-4-nitrosobenzene (0.5 mmol) to provide the title compound as white solid (179 mg, 78% yield) after silica gel chromatography (EtOAc/Hexane).

$^1H$ NMR (400 MHz, $CDCl_3$) δ 9.66 (s, 1H, CHO), 7.50-6.93 (m, 8H, ArH), 5.47-5.38 (m, 1H, $CHNO_2$), 4.57 (m, 1H, CHCHO), 4.28 (m, 1H, CHN), 2.86-2.71 (m, 2H, $CH_2Ar$), 2.23-2.09 (m, 2H, $CH_2CHCHO$), 2.07-1.75 (m, 2H, $CH_2CHN$).

$^{13}C$ NMR (100 MHz, $CDCl_3$): δ 201.9, 147.5, 133.6, 133.3, 132.5, 129.9 129.1, 115.8, 115.2, 88.4, 83.3, 60.4, 37.8, 22.5, 18.9.

HPLC: Chiralpak AS-H (hexane/i-PrOH, 85/15, flow rate 1 mL/min, λ=254 nm), $t_R$ (major)=14.6 min, $t_R$ (minor)=34.2 min; >99% ee.

$[\alpha]_D^{25}$=−17.5 (c=1.2, $CHCl_3$).

HRMS (EI) calcd for $C_{19}H_{18}BrClO_4N_2$, m/z 452.0133, found 452.0136.

(3R,6R)-3-((S)-2-(4-bromophenyl)-1-nitroethyl)-2-Phenylmorpholine-6-carbaldehyde 33o 33o

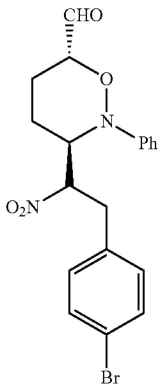

Prepared according to the general procedure from 31h (1.5 mmol) and nitrosobenzene (0.5 mmol) to provide the title compound as white solid (157 mg, 75% yield) after silica gel chromatography (EtOAc/Hexane).

$^1$H NMR (300 MHz, $CDCl_3$) δ 9.68 (s, 1H, CHO), 7.39-6.82 (m, 9H, ArH), 5.45-5.37 (m, 1H, $CHNO_2$), 4.55-4.54 (m, 1H, CHCHO), 4.28-4.26 (m, 1H, CHN), 2.83-2.63 (m, 2H, $CH_2Ar$), 2.21-2.15 (m, 2H, $CH_2CHCHO$), 2.11-1.71 (m, 2H, $CH_2CHN$).

$^{13}$C NMR (75 MHz, $CDCl_3$): δ 202.4, 148.5, 134.2, 131.9, 130.2, 129.5, 122.8, 121.7, 114.3, 88.5, 83.2, 60.7, 37.8, 22.7, 19.1.

HPLC: Chiralpak AS-H (hexane/i-PrOH, 85/15, flow rate 1 mL/min, λ=220 nm), $t_R$ (major)=13.3 min, $t_R$ (minor)=49.1 min; >99% ee.

$[\alpha]_D^{25}$=−26.7 (c=1.2, $CHCl_3$).

HRMS (EI) calcd for $C_{19}H_{19}BrO_4N_2$, m/z 418.0523, found 418.0530.

(3R,6R-2-(4-bromophenyl)-3-0S)-2-(4-bromophenyl)-1-nitroethyl)morpholine-6-carbaldehyde 33p 33p

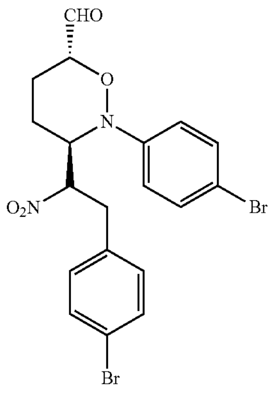

Prepared according to the general procedure from 31h (1.5 mmol) and 1-bromo-4-nitrosobenzene (0.5 mmol) to provide the title compound as white solid (34.8 mg, 70% yield) after silica gel chromatography (EtOAc/Hexane).

$^1$H NMR (400 MHz, $CDCl_3$) δ 9.66 (s, 1H, CHO), 7.50-6.87 (m, 8H, ArH), 5.44-5.38 (m, 1H, $CHNO_2$), 4.57 (m, 1H, CHCHO), 4.27 (m, 1H, CHN), 2.84-2.69 (m, 2H, $CH_2Ar$), 2.22-2.18 (m, 2H, $CH_2CHCHO$), 2.11-1.75 (m, 2H, $CH_2CHN$).

$^{13}$C NMR (100 MHz, $CDCl_3$): δ 201.9, 147.5, 133.8, 132.5, 132.0, 130.2, 121.7, 116.2, 115.8, 88.3, 83.3, 60.4, 37.9, 22.5, 18.9.

HPLC: Chiralpak AS-H (hexane/i-PrOH, 85/15, flow rate 1 mL/min, λ=220 nm), $t_R$ (major)=15.1 min, $t_R$ (minor)=32.7 min; 99% ee.

$[\alpha]_D^{25}$=−24.1 (c=1.3, $CHCl_3$).

HRMS (EI) calcd for $C_{19}H_{18}Br_2O_4N_2$, m/z 495.9637, found 495.9641.

(3R,6R)-3-(nitromethyl)-2-p-tolylmorpholine-6-carbaldehyde 33q

33q

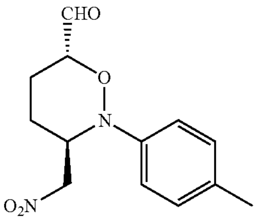

Prepared according to the general procedure from 31a (1.5 mmol) and 4-nitrosotoluene (0.5 mmol) to provide the title compound as white solid (119 mg, 90% yield) after silica gel chromatography (EtOAc/Hexane).

$^1$H NMR (500 MHz, $CDCl_3$) δ 9.77 (d, J=1.0 Hz, 1H, CHO), 7.20-7.06 (m, 4H, ArH), 4.85-4.81 (m, 1H, $CHNO_2$), 4.54-4.50 (m, 2H, $CHNO_{2+}CHCHO$), 4.40-4.38 (m, 1H, CHN), 2.35 (s, 3H, $ArCH_3$), 2.33-2.11 (m, 2H, $CH_2CHCHO$), 2.10-1.85 (m, 2H, $CH_2CHN$).

$^{13}$C NMR (125 MHz, $CDCl_3$): δ 202.6, 145.0, 133.5, 129.9, 116.0, 82.4, 71.9, 58.0, 22.0, 20.7, 18.6.

HPLC: Chiralpak AS-H (hexane/i-PrOH, 85/15, flow rate 1 mL/min, λ=230 nm), $t_R$ (major)=13.4 min, $t_R$ (minor)=33.8 min; >99% ee.

$[\alpha]_D^{25}$=−227.5 (c=0.9, $CHCl_3$).

HRMS (EI) calcd for $C_{13}H_{16}O_4N_2$, m/z 264.1105, found 264.1099.

Survey the Catalysis in the Michael Addition Step

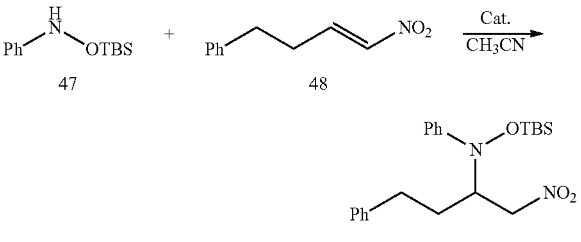

47 + 48 → 49

| entry | cat. (mol %) | temperature | time | % yield[b] |
|---|---|---|---|---|
| 1 | none | r.t. | 48 h | n.r. |
| 2 | none | −20° C. | 96 h | n.r. |
| 3 | TEA (100) | r.t. | 48 h | 31 |
| 4 | Quinine (20) | r.t. | 12 h | 95 |

[a]Unless otherwise noted, reactions were conducted with 1.0 equiv of 47 (1M), 1.0 equiv of 48 in $CH_3CN$.
[b]Isolated yield.

A control experiment was designed to investigate the second Michael addition step by using 47 and 48 as mimics of the in situ generated amine moiety and nitroalkene part respectively. Without catalyst, the reaction did not proceed even after 2 days (entry 1); for the case at −20° C., similar result was obtained (entry 2). In the presence of 1 equiv of TEA as general base, the reaction gave 31% of Michael product after 48 h (entry 3), which revealed that tertiary amine itself was not efficient to enhance the reactivity of this transformation. When we changed to a catalyst with H bond donating ability such as Quinine, the reaction went on smoothly, providing 49 in excellent yield (entry 8). These observations implied that the second Michael addition step may be promoted through H-bonding catalysis. Combined with the fact that no intermediates can be detected by NMR experiments of reaction mixture or isolated, we propose a concerted mechanism for this tandem reaction: After the first aminoxylation step, which is known to proceed with high enantio-selectivity; clearly this selectivity is kept in the second step via a sterically favorable transition state (vide infra), and the final protonation was actually conducted in a concerted route assisted by a molecule of water through double H-bonding with in situ generated amine and the nitro group (cf. FIG. 12B). The proposed transition state is confirmed by DFT calculations (vide infra).

Computational Details.

DFT calculations were carried out with the Gaussian 03 package[5]. The transition structures are fully optimized by B3LYP[6] method using 6-31G(d) basis set and have been confirmed to be a saddle point by the harmonic frequencies calculations at the same level of theory. Transition state geometries are also optimized in $CH_3CN$ solution with PCM model (Cossi, M, et al., J. Chem. Phys. (2002) 117, 43-54) in Gaussian 03.

Figure 19A:
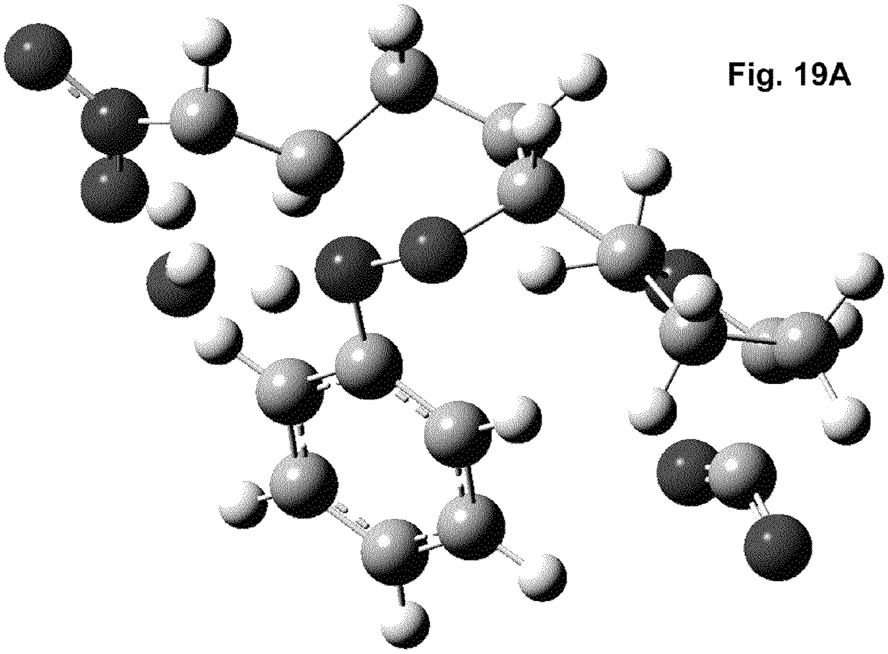
FIG. 19A depicts the transition state for N—H adding to the C═C bond in the course of the reaction in the gas phase, and FIG. 19B the transition state for N—H adding to the C═C bond in $CH_3CN$ solution.
Figure 19B:
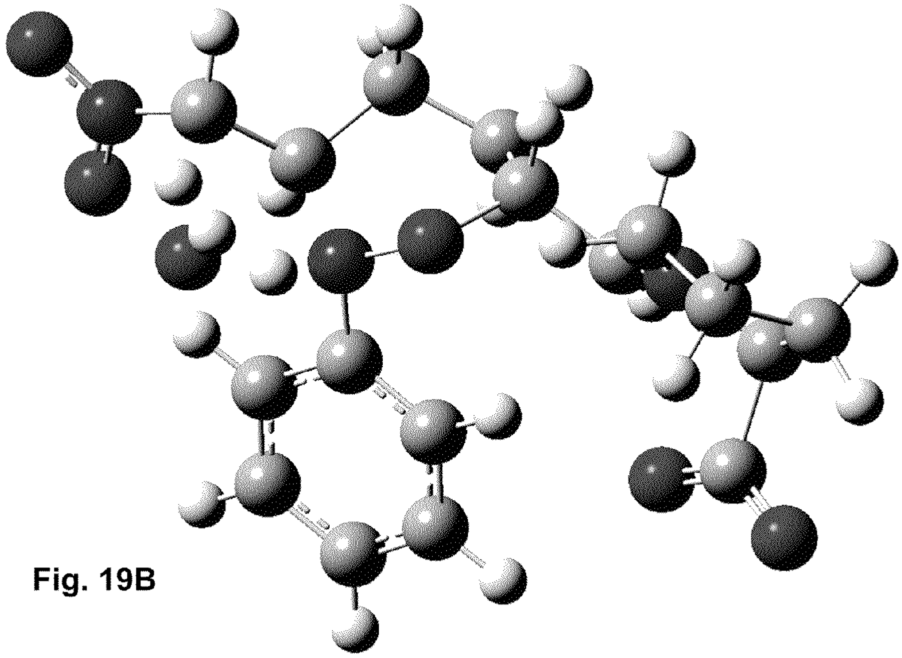
Figure 21A:
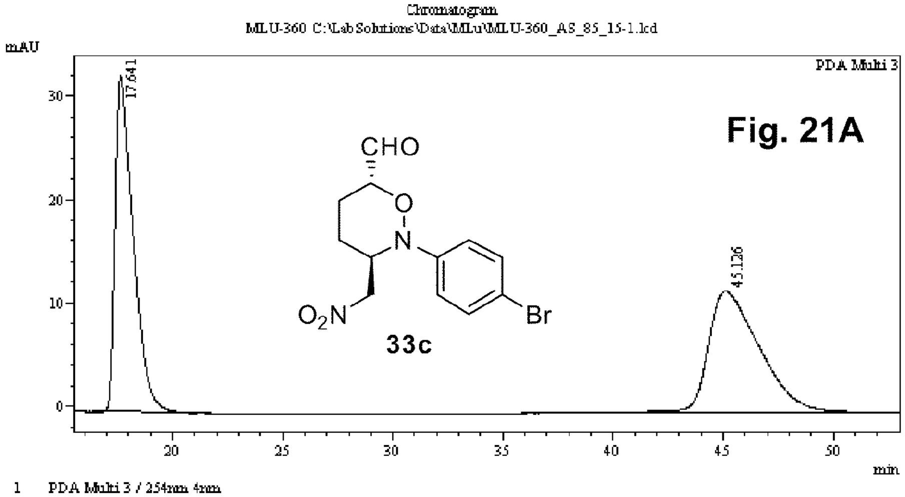
FIG. 21 depicts a HPLC spectrum of a racemic mixture of compound 33c (A) in comparison to the obtained product 33c (B).
Figure 21B:
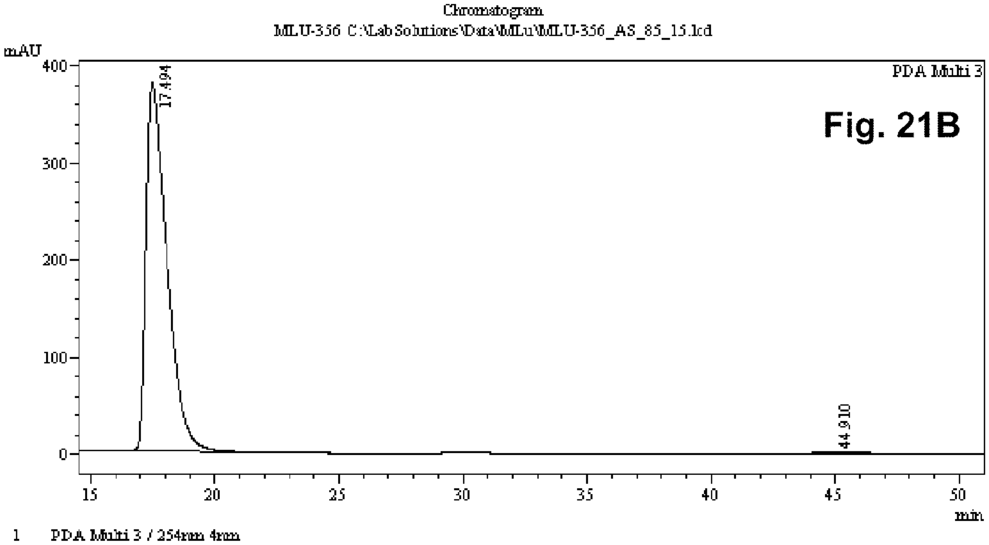
Figure 22A:
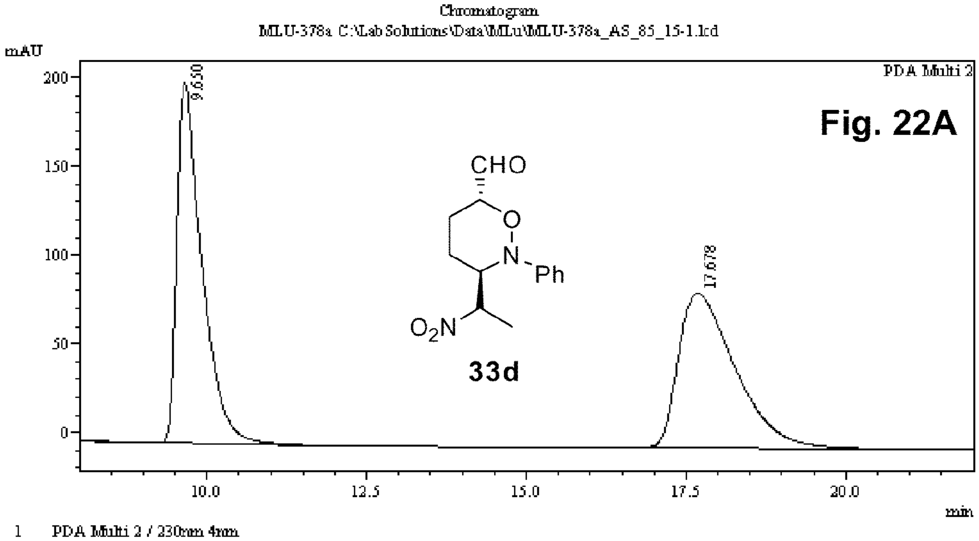
FIG. 22 depicts a HPLC spectrum of a racemic mixture of compound 33d (A) in comparison to the obtained product 33d (B).
Figure 22B:
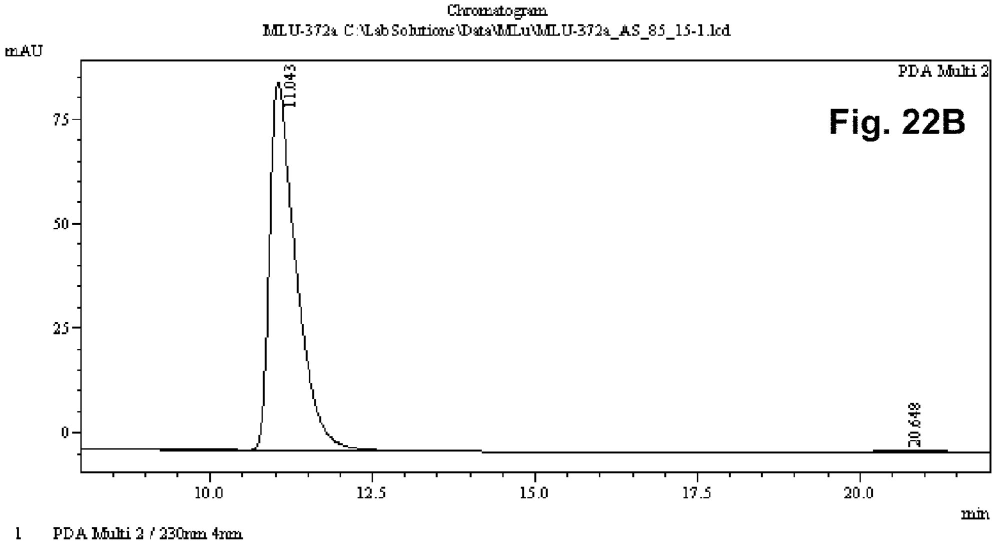
Figure 24A:
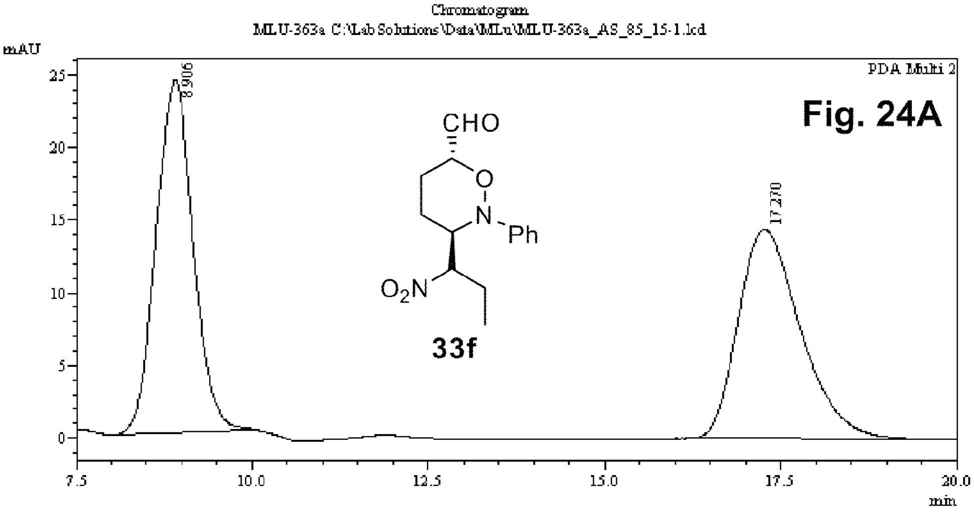
FIG. 24 depicts a HPLC spectrum of a racemic mixture of compound 33f (A) in comparison to the obtained product 33f (B).
Figure 24B:
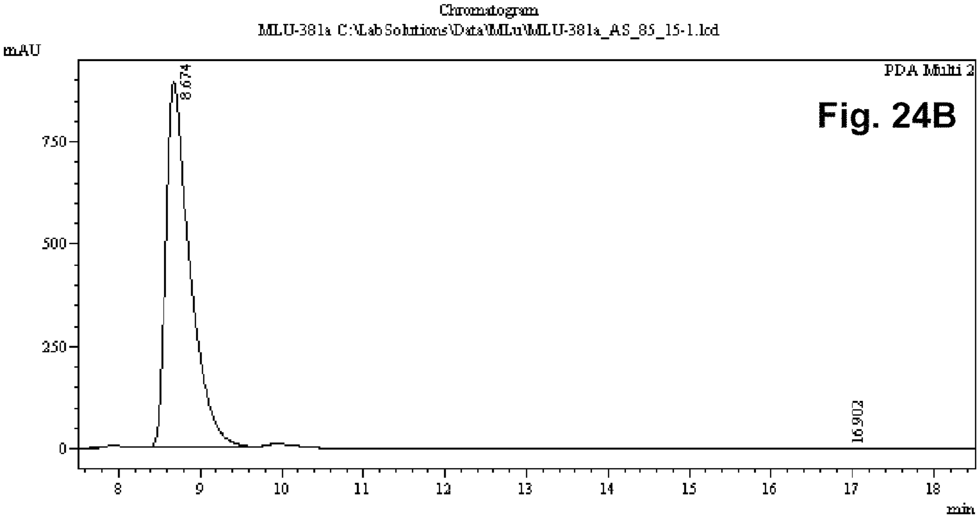
Figure 26A:
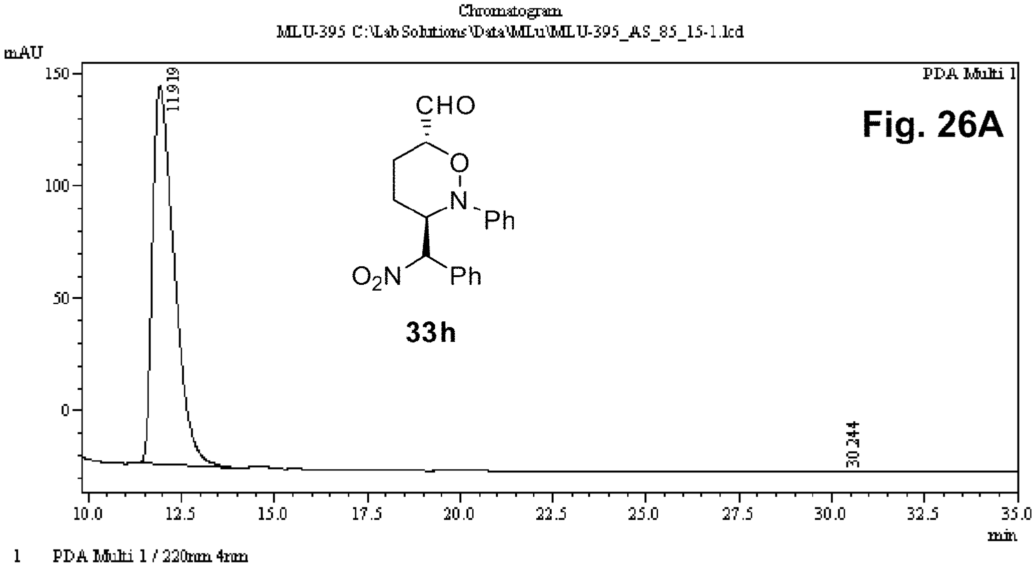
FIG. 26 depicts a HPLC spectrum of a racemic mixture of compound 33h (A) in comparison to the obtained product 33h (B).
Figure 26B:
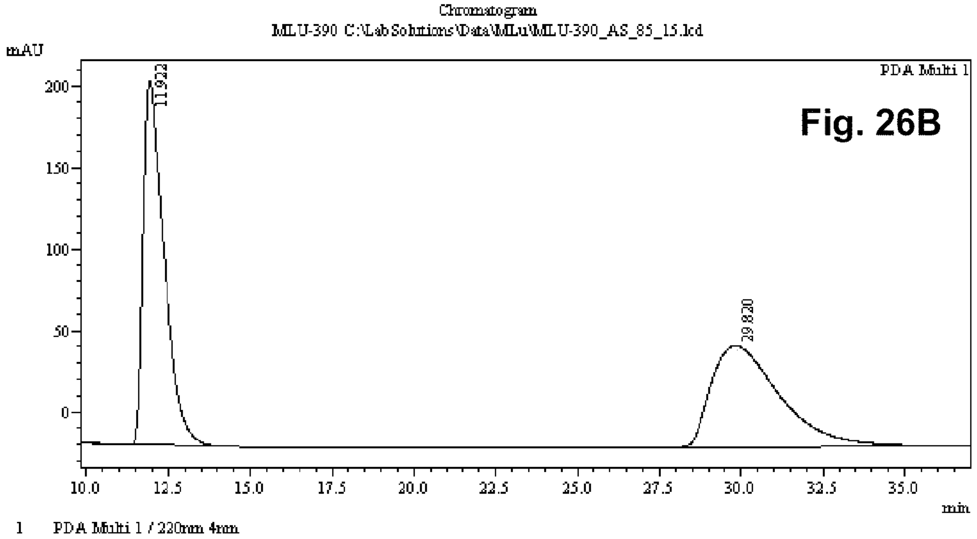
Figure 27:
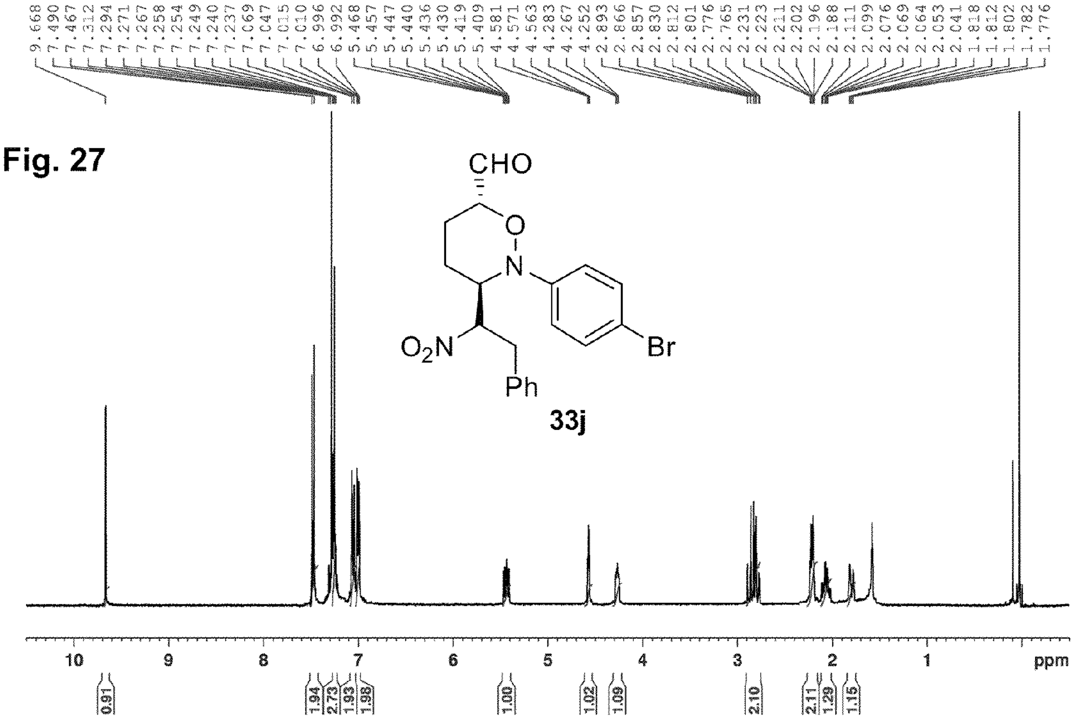
FIG. 27 depicts a $^{1}H$ NMR spectrum of compound 33j.
Figure 28:
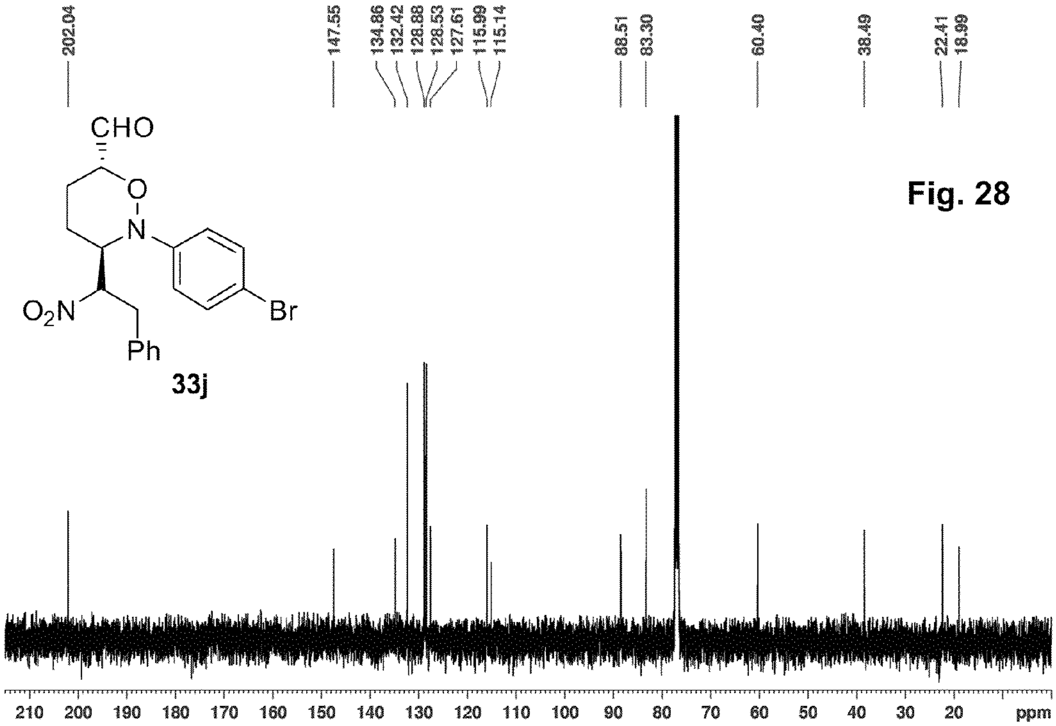
FIG. 28 depicts a $^{13}C$ NMR spectrum of compound 33j.
Figure 30A:
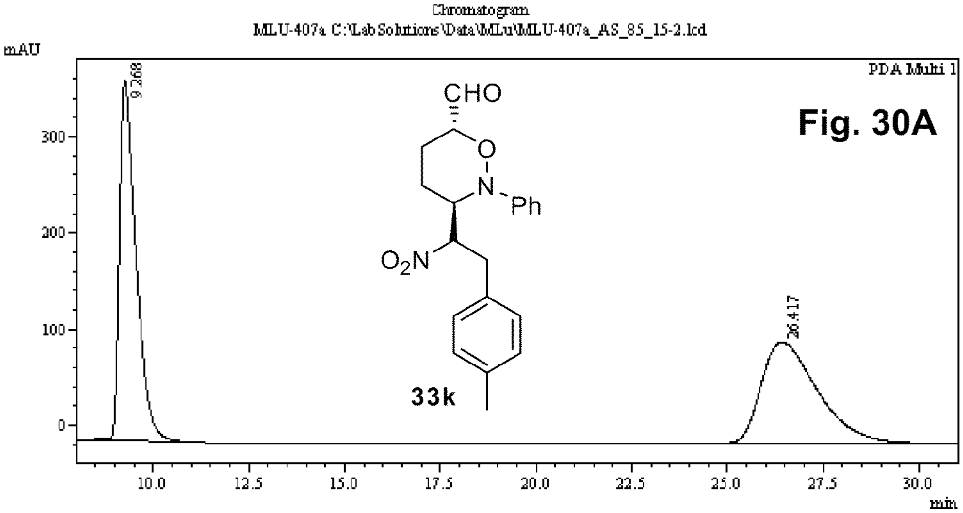
FIG. 30 depicts a HPLC spectrum of a racemic mixture of compound 33k (A) in comparison to the obtained product 33k (B).
Figure 30B:
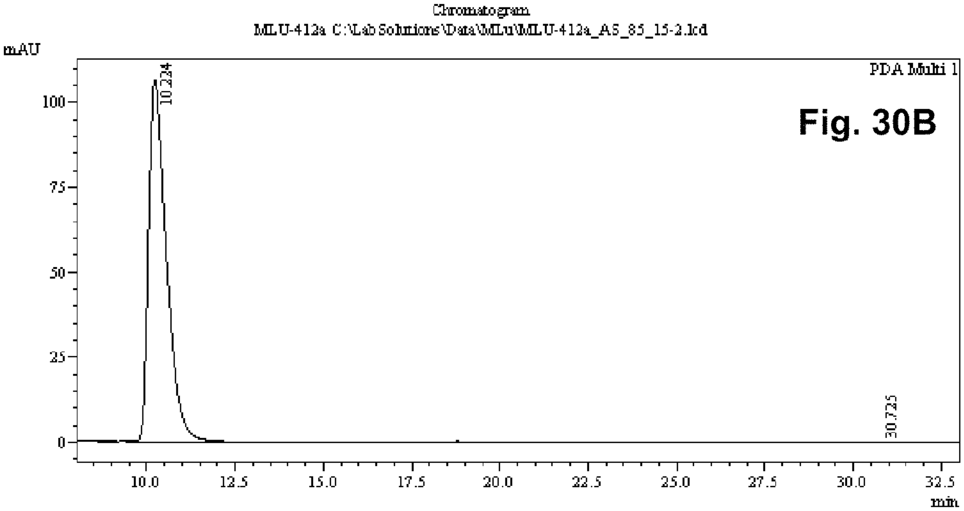
Figure 32A:
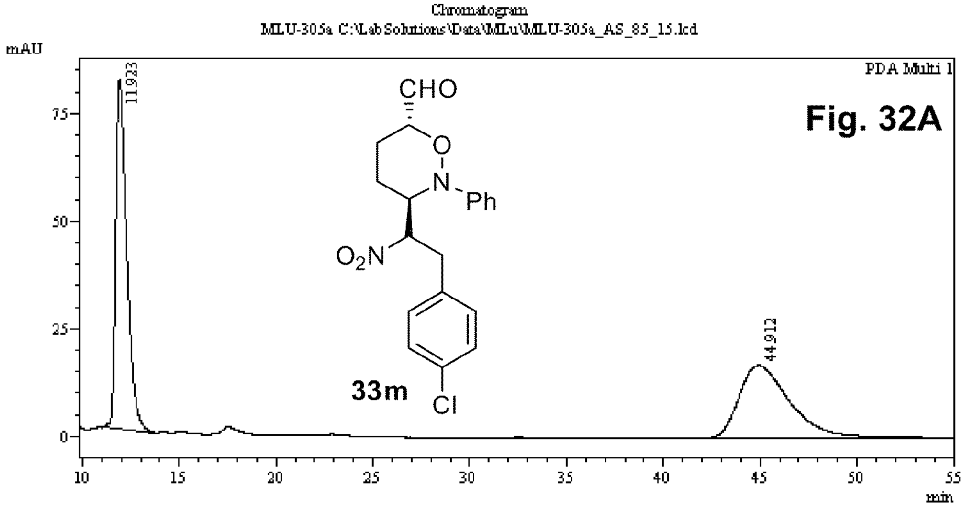
FIG. 32 depicts a HPLC spectrum of a mixture of compound 33m (A) in comparison to the obtained product 33m (B).
Figure 32B:
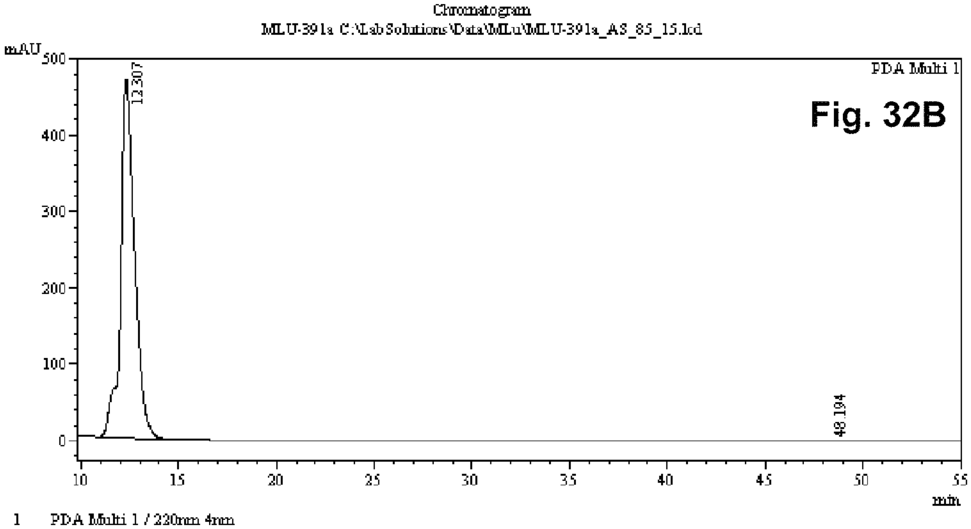
Figure 33A:
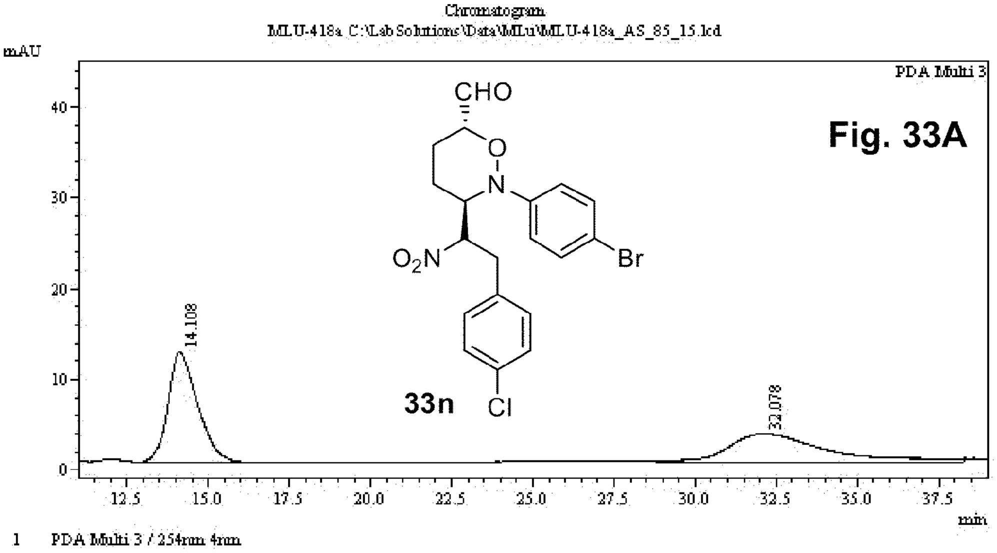
FIG. 33 depicts a HPLC spectrum of a mixture of compound 33n (A) in comparison to the obtained product 33n (B).
Figure 33B:
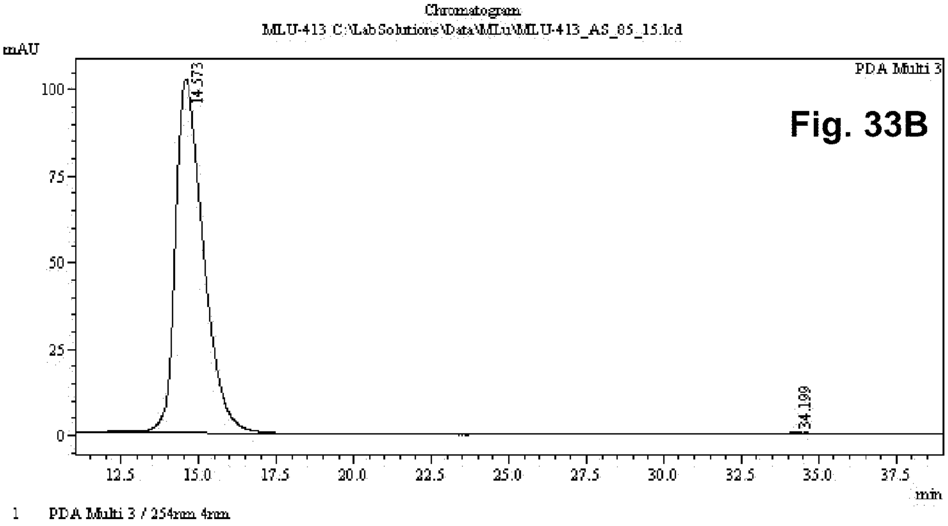
Figure 34A:
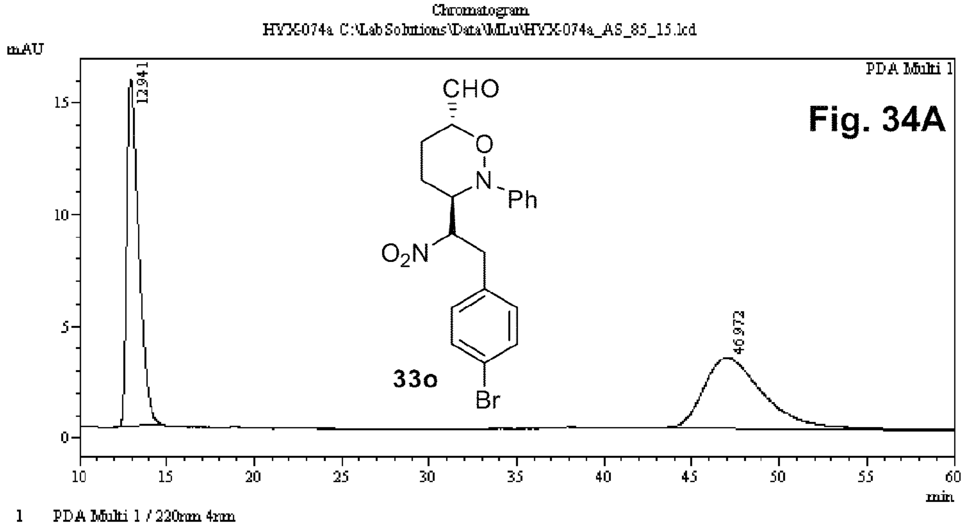
FIG. 34 depicts a HPLC spectrum of a mixture of compound 33o (A) in comparison to the obtained product 33o (B).
Figure 34B:
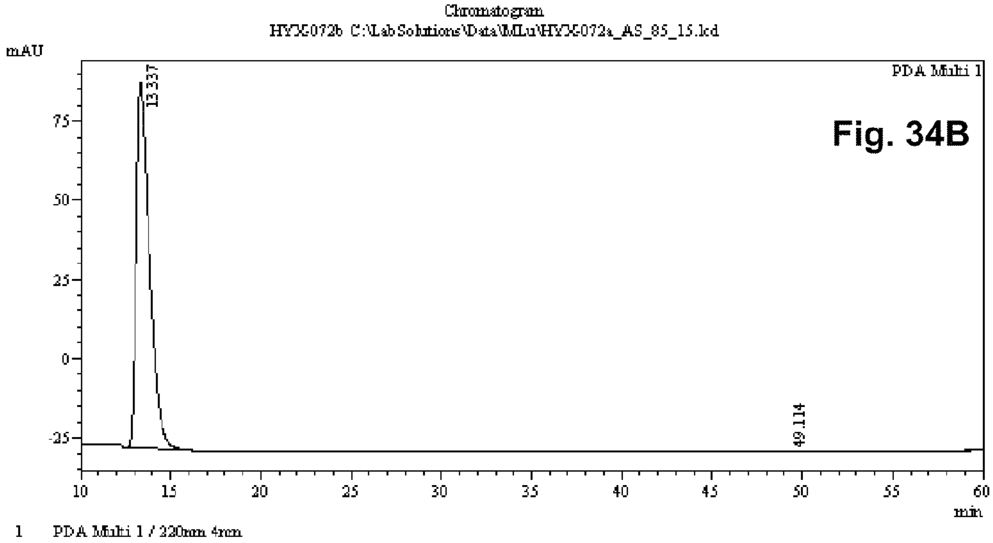
Figure 35A:
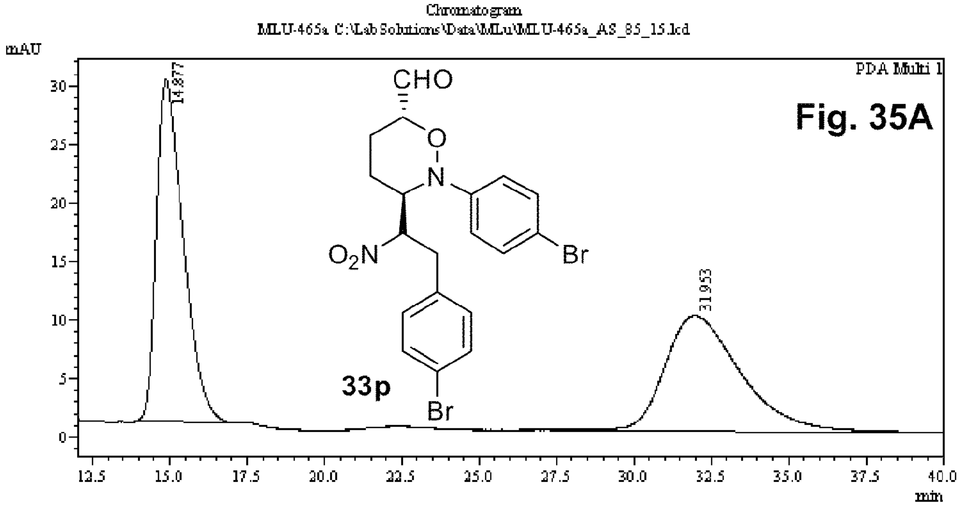
FIG. 35 depicts a HPLC spectrum of a mixture of compound 33p (A) in comparison to the obtained product 33p (B).
Figure 35B:
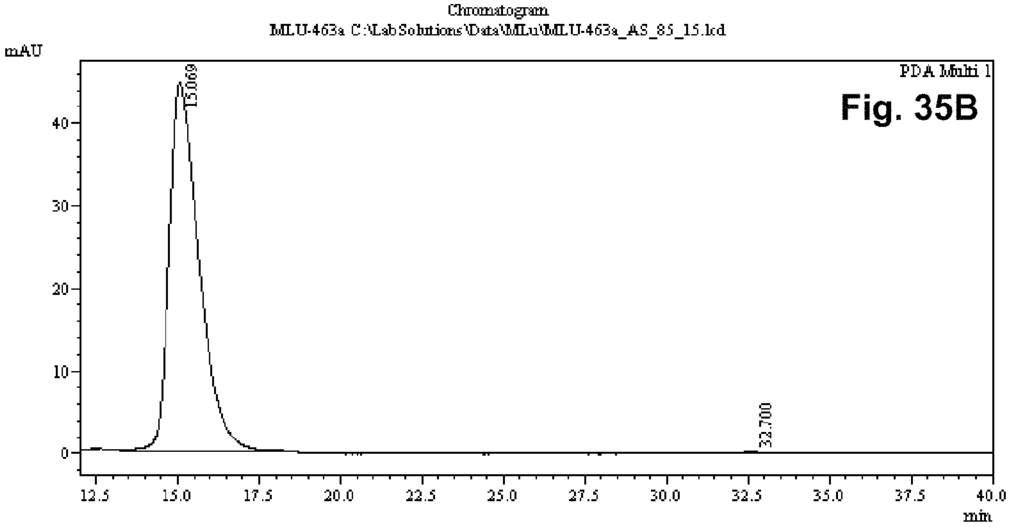
Figure 36A:
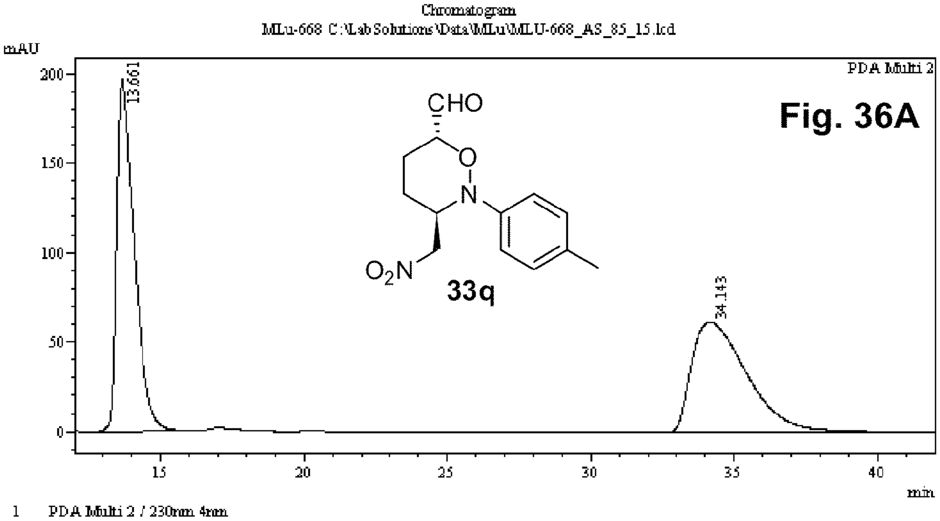
FIG. 36 depicts a HPLC spectrum of a mixture of compound 33q (A) in comparison to the obtained product 33q (B).
Figure 36B:
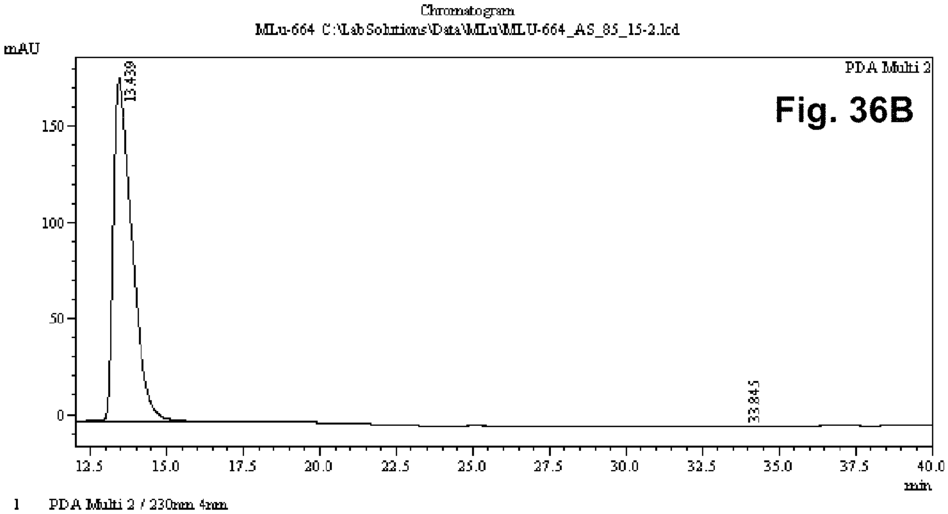
Figure 38:
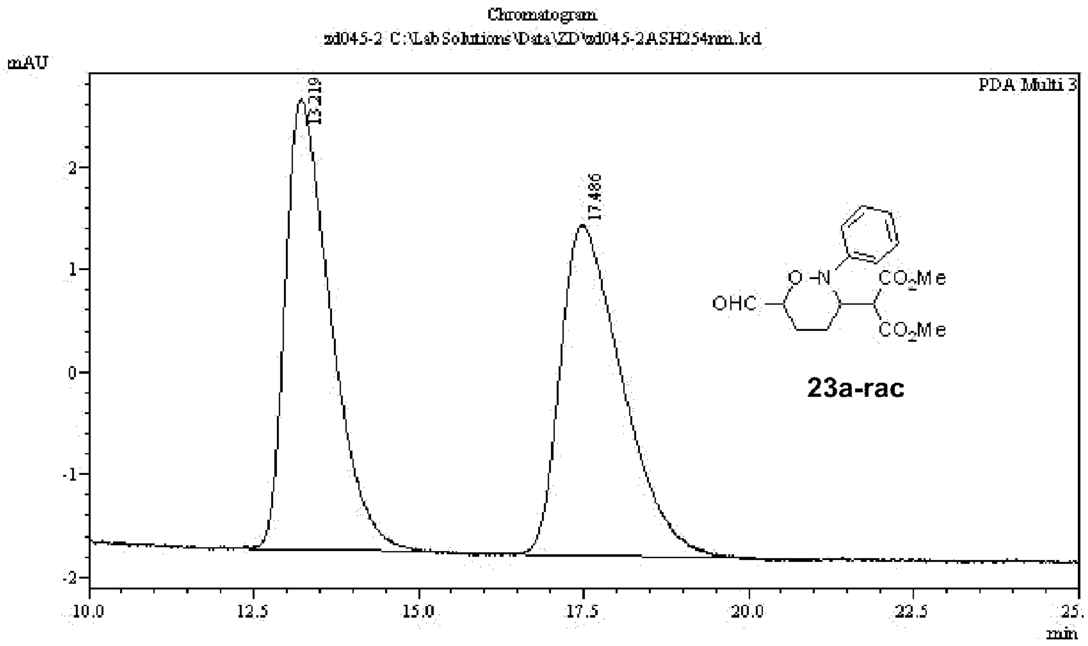
Figure 39:
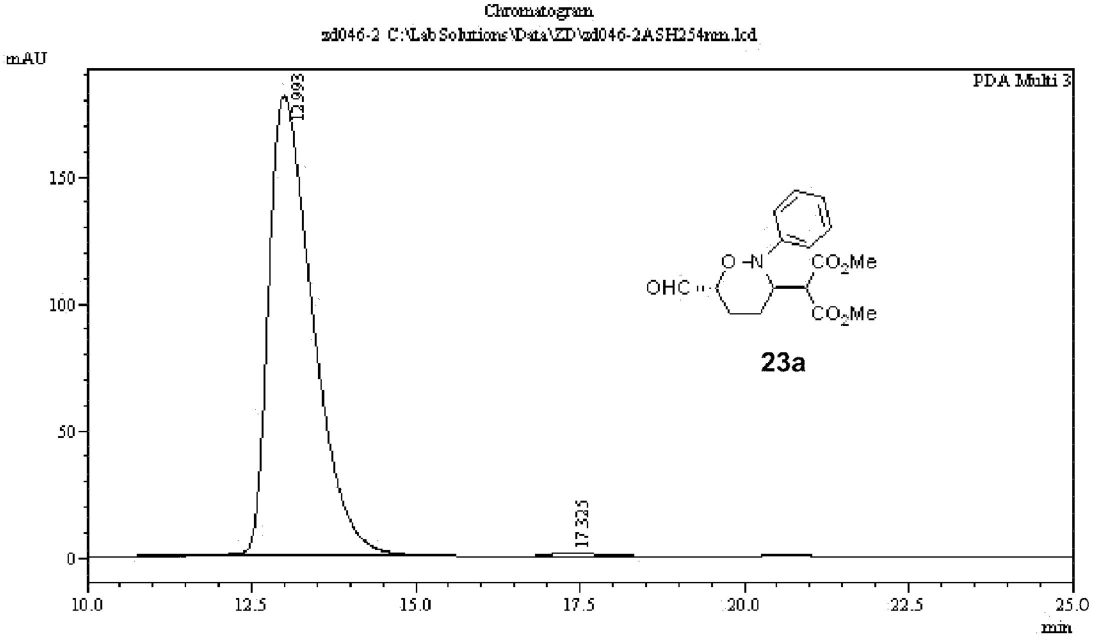
Figure 40:
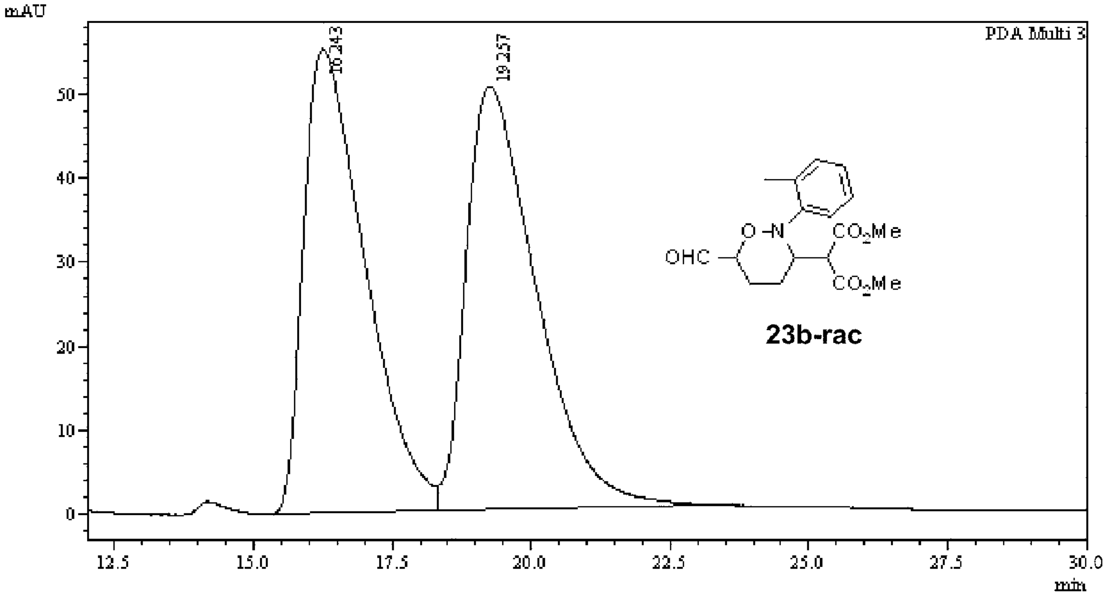
FIG. 40 depicts an HPLC spectrum of a racemic mixture of compound 23b.
Figure 41:
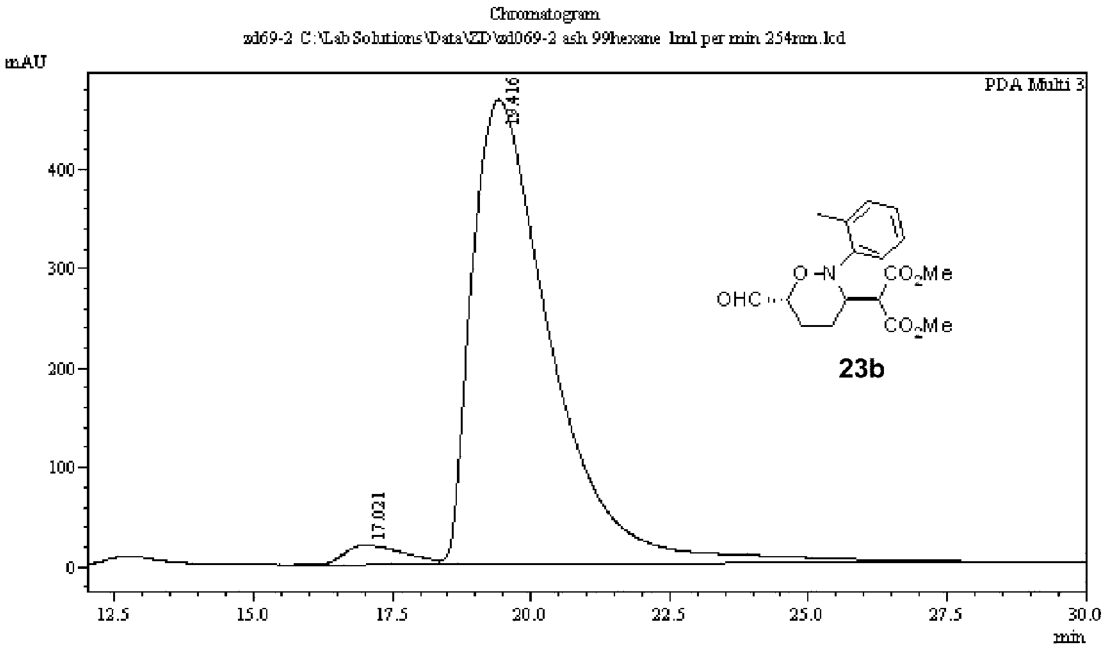
FIG. 41 depicts an HPLC spectrum of obtained compound 23b.

The calculated lowest energy transition state in gas phase and $CH_3CN$ solution are shown in FIG. 19A and FIG. 19B respectively.

EXAMPLE 3

Formation of Functionalized Tetrahydro-1,2-oxazines via α-Aminoxylation of Aldehydes and Aza-Michael Reaction using Aldehydes with an α,β-unsaturated 1,3-dicarboxyl moiety Investigations were started using the previously established conditions: nitrosobenzene (0.1 mmol, 1.0 equiv) and dimethyl 2-(5-oxopentylidene)malonate (0.12 mmol, 1.2 equiv) were added to 20 mol % L-proline in 1.0 mL of DMSO. The organocatalytic tandem aminoxylation/aza-Michael reaction was facile at room temperature and can be accomplished within 30 min. The reaction progress can be easily monitored by observation of its color change from green to orange. After workup, the desired cyclic product was isolated in 37% yield with excellent enantioselectivity (98% ee) and diastereoselectivity (>99:1 dr) (FIG. 13, entry 1). Furthermore, various catalysts and solvents were surveyed and summarized in FIG. 13. The reaction proceeded smoothly in the presence of pyrrolidinyl tetrazole IXb or thiazolidine-4-carboxylic acid IXd to afford the cycloadduct in a slightly lower yield and without any loss in the ee and dr values (FIG. 13, entries 2 and 3). Unfortunately, Jørgenson's catalyst IV cannot be employed in this reaction to afford the corresponding α-aminoxylation/aza-Michael product. L-Proline was chosen as the catalyst not only because it is abundant and cheap, but more importantly because of its efficiency among all the other investigated catalysts. The screening of various solvents revealed that $CH_3CN$ is the best solvent as it gave the highest yield (52%) and without any loss of enantio- or diastereoselectivities (FIG. 13, entry 5). Halogenated solvent $CHCl_3$ (Table 1, entry 6) and highly polar and protophilic solvents, such as DMF and NMP (FIG. 13, entries 7 and 8), gave relatively lower yields (41-46%) whereas a less polar ethereal solvent, such as THF (FIG. 13, entry 9), and the most polar solvent water showed a deleterious effect on reactivity even after addition of tetraethyl ammonium bromide as PTC and stirring for 24 h (FIG. 13, entry 11).

Having established the choice of catalyst, the reaction temperatures were screened. It was observed that when the reaction temperature decreased from room temperature to −20° C. (FIG. 14, entries 1-3), the suppression of both side reaction and homodimer formation led to an increase in yield (from 52% to 65%) and without any loss in the ee and dr values. Increasing the equivalence of aldehyde to nitrosobenzene from 1.2 to 3 equiv increased the yield from 65% to 79% and at the same time decreased the reaction time from 24 h to 13 h. (FIG. 14, entries 3-6). Lastly, when the catalyst loadings were decreased from 20 to 5 mol %, the highest yield was found when 10 mol % of L-proline was used (FIG. 14, entries 6-8). In terms of operational convenience, 10 mol % of L-proline ensured high levels of reaction efficiency and enantioselectivity and was thus used in the next reaction. It is also noteworthy that after in situ reduction, the dr of corresponding alcohol product dropped significantly to 1:1 (FIG. 14, entry 9).

Figure 16:
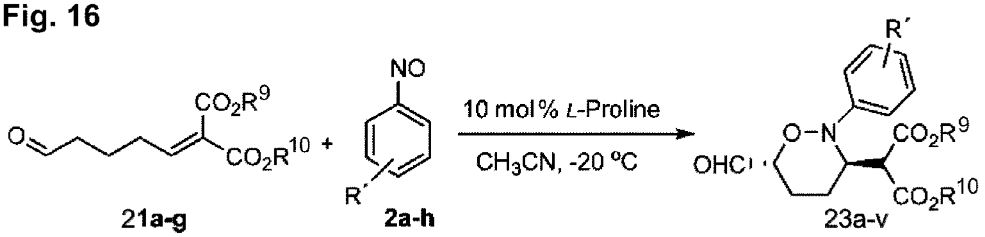
FIG. 16 depicts an analysis of the reaction scope of the tandem aminoxylation/Aza-Michael Addition based on an aldehyde 21a with a dicarboxyl moiety. Conditions: Nitrosobenzene (0.1 mmol) and L-proline (0.01 mmol) were added to the solution of aldehyde (0.3 mmol) in 1 mL of $CH_3CN$ at −78° C., then stirred at −20° C.: Isolated yields. b: Ee and dr determined by HPLC employing a Daicel Chiracel AS-H or AD-H column (see the Examples below).
Figure 18A:
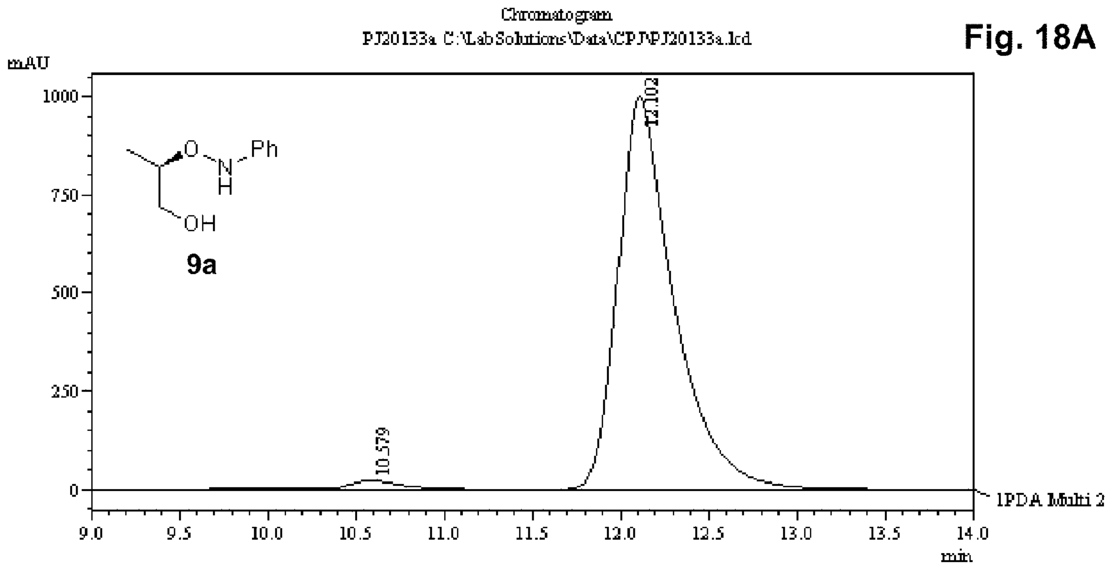
FIG. 18 depicts an HPLC spectrum of obtained compound 9a (A) in comparison to a racemic mixture thereof (B).
Figure 18B:
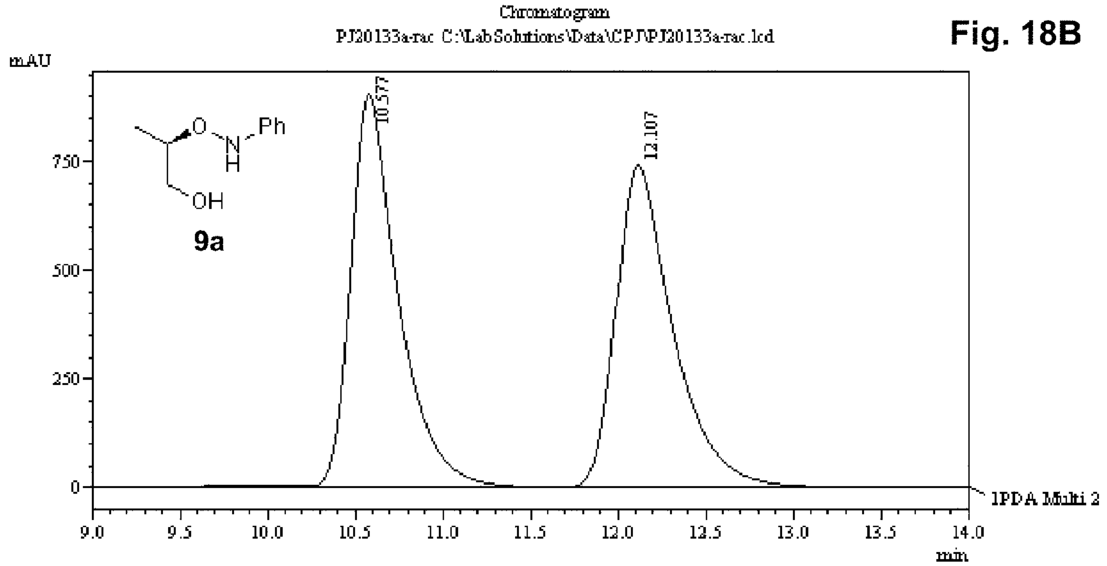

We further explored the generality of the reaction. The optimized reaction condition was applicable for reactions of various aromatic nitroso compounds 2a-h and some 2-(5-oxopentylidene) malonate derivatives 21a-g, to give moderate to good yields (52-84%) in excellent ee values (92-99%) and dr values (>99:1). The 2-methyl substituent in nitrosotoluene introduced more steric hindrance in the Michael addition step and this may account for the decrease in ee values (from 98% to 94% ee) when compared to the other nitrosobenzene derivatives. We observed that the substitutents in malonate also affected the yield of the Michael adducts. Isopropyl substituent, being more sterically hindered than propyl groups, generally gave low yields when compared with that of propyl substituents (FIG. 16, entries 10-11, 16-17, and 20- 21). The reason why dipentyl 2-(5-oxopentylidene) malonate gave the worst result remains unknown (FIG. 16, entry 13).

To determine the stereochemistry of the tandem aminoxylation/aza-Michael reaction, a (2,4-dinitrophenyl) hydrazine derivative 50i of the aldehyde product 23i was synthesized (FIG. 15). The relative configuration of the (2,4-dinitrophenyl) hydrazone 50i was then determined by X-ray crystallography (FIG. 17). The R configuration of the chiral center created by the Michael addition was established by comparing it with the sterogenic center generated by the aminoxylation step based on the relative configuration of 4i and the known chemistry 7 of the aminoxylation.

In summary, the first highly diastereo and enantioselective approach for the synthesis of these functionalized tetrahydro-1,2-oxazines via an organocatalyzed asymmetric tandem aminoxylation/aza-Michael reaction is presented. Further applications of this functionalized THOs to other synthetically useful transformations are underway.

General Experimental Information

Unless otherwise stated, all reagents were purchased from commercial suppliers and used without further purification. All solvents employed in the reactions were used directly without further purification. Organic solutions were concentrated under reduced pressure on Heidolph rotary evaporator. Reactions were monitored by thin-layer chromatography (TLC) on silica gel precoated glass plates (0.25 mm thickness, 60E-254, E. Merck). Chromatograms were visualized by fluorescence quenching with UV light at 254 nm or by staining using 2,4-dinitrophenyl hydrazine (2,4-DNP) stains. Further visualization was possible by staining with base solution of potassium permanganate. Flash column chromatography was performed using silica gel 60 (particle size 0.040-0.063 mm) from Merck. Racemic products were catalyzed by D,L-Proline.

IR spectra were recorded using FTIR Restige-21 (Shimadzu) with neat oil samples.

High Resolution Mass (HRMS) spectra were obtained using Finnigan MAT95XP GC/HRMS (Thermo Electron Corporation) for EI+;QTOF perimer for $ESI^+$ and $ESI^-$.

Proton nuclear magnetic resonance spectra ($^1H$ NMR) were. recorded on a Bruker Avance DPX300, Bruker AMX400 and AMX500 spectrophotometer ($CDCl_3$ as solvent). Chemical shifts for $^1H$ NMR spectra are reported as δ in units of parts per million (ppm) downfield from $SiMe_4$ (δ 0.0) and relative to the signal of chloroform-d (δ 7.26, s). Multiplicities were given as: s (singlet); d (doublet); t (triplet); q (quartet); dd (doublets of doublet); dt (doublets of triplet); or m (multiplets). The number of protons (n) for a given resonance is indicated by nH. Coupling constants are reported as a J value in Hz. Carbon nuclear magnetic resonance spectra ($^{13}C$ NMR) are reported as 6 in units of parts per million (ppm) downfield from $SiMe_4$ (δ 0.0) and relative to the signal of chloroform-d (δ 77.0, t).

Enantioselectivities were determined by High performance liquid chromatography (HPLC) analysis employing a Daicel Chiracel OD-H or AS-H column at 25° C. (in comparison with racemic products). Optical rotations were measured in $CHCl_3$ on a Schmidt+Haensch polarimeter with a 1 cm cell (c given in g/1 mL).

Absolute configurations of the products were determined by X-Ray crystallography together with comparison of NMR data.

General Procedure for the Preparation of Substrates

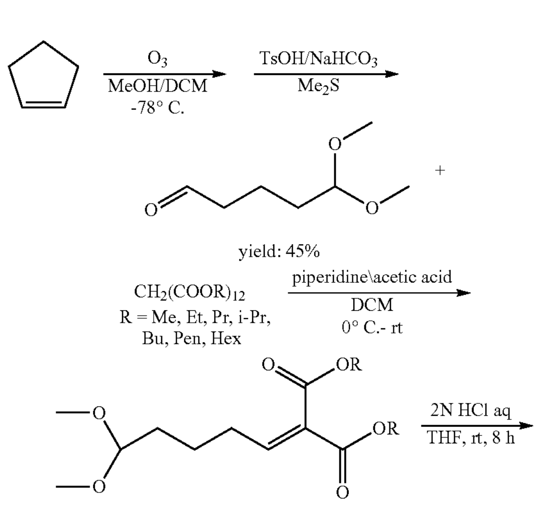

R = Me, Et, Pr, i-Pr, Bu, Pen, Hex

-continued

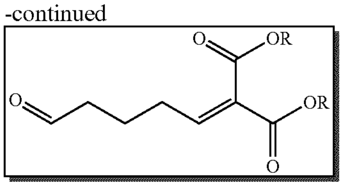

R = Me, Et, Pr, i-Pr, Bu, Pen, Hex 5,5-Dimethoxypentanal (Aggarwal, V. K.; Roseblade, S. J.; Barrell, J. K.; Alexander, R. Org. Lett. (2002) 4, 1227-1229)

A 500 mL, three-necked, round-bottomed flask was fitted with a glass frit to admit ozone, and a magnetic stirrer bar and was charged with cyclopentene (6.8 g, 100 mmol), anhydrous dichloromethane (250 mL) and anhydrous methanol (50 mL). The flask was cooled to −78° C. and ozone was bubbled through the solution with stirring until a blue colour remained. Nitrogen was passed through the solution until the blue colour was discharged and then the cold bath was removed. The drying tube and ozone inlet were replaced with a glass stopper and a rubber septum and PTsOH monohydrate (1.47 g, 7.70 mmol, 10% w/w) was added. The solution was allowed to warm to room temperature as it stirred under nitrogen for 90 minutes.

Anhydrous sodium hydrogencarbonate (2.59 g, 30.8 mmol) was added to the flask and the mixture was stirred for 15 minutes after which time dimethyl sulfide (16 mL, 200 mmol) was added. After stirring for 16 hours the heterogeneous mixture was concentrated in vacuo. Dichloromethane (100 mL) was added and the mixture was washed with water (75 mL). The aqueous layer was extracted with dichloromethane (3×100 mL) and the combined organic layers were dried ($MgSO_4$), filtered and concentrated in vacuo. Column chromatography (EtOAc/Hexane=15:85) on silica gel gave aldehyde as a colorless oil (7.0 g, 48%). ($^1H$-NMR [300 MHz, $CDCl_3$] 1.57-1.79 (4H, m), 2.44-2.52 (2H, m), 3.32 (6H, s, $2\times OCH_3$), 4.37 (1H, t, J=5.6 Hz, $CH(OMe)_2$), 9.77 (1H, t, J=1.3 Hz, CHO).

General Procedure of the Knoevenagel Reaction (Tietze, L. F.; Beifuss, U. Angew. Chem. Int. Ed. (1985) 97, 1067-1068)

To a stirred solution of 5,5-dimethoxypentanal (1.46 g, 10 mmol) and dimethyl malonate (1.45 g, 11 mmol) in anhydrous methylene chloride (5 mL) were added piperidine (85 mg, 1 mmol) and acetic acid (60 mg, 1 mol) at 0° C., the mixture was stirred at room temperature for 45 min, TLC monitored, after the completely consumption of Aldehyde, the reaction mixture was evaporated in vacuo, diluted with ether 50 mL, and washed twice with water (20 mL×2), the aqueous phases were extracted with ether (10 mL×3), the organic phases were successively washed with saturated sodium bicarbonate solution (10 mL), water (10 mL), brine (10 mL), and dried over anhydrous $Na_2SO_4$. After removed the solvent, the crude product was purified on silica gel column or directly used in next step. Obtained 1.0 g colorless oil, yield 42%.

General Procedure of Deprotection (Zhou, Gang; Hu, Qi-Ying; Corey, E. J. Org. Lett. (2003) 5, 3979-3982)

To a solution of dimethyl 2-(5,5-dimethoxypentylidene) malonate (1.0 g, 3.84 mmol) in THF (20 mL) was added 2N HCl (4 mL). After stirring for 8 h at r.t., the mixture was extracted with $Et_2O$ (3×50 mL). The organic phase was combined, washed with aq. $NaHCO_3$ solution (3×10 mL), brine (2×10 mL), and dried ($MgSO_4$). The solvent was removed in vacuo, Column chromatography (EtOAc:Hexane=10:90) on silica gel gave to give 0.7 g (83%) of aldehyde as a colorless oil.

21a

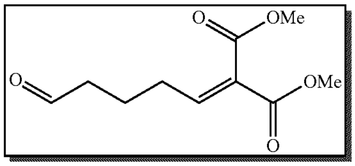

Colorless oil, yield 36% (two step) after silica gel chromatography (EtOAc/Hexane=15:85).

$^{1}$H NMR (300 MHz, $CDCl_3$): δ 9.78 (t, J=1.2 Hz, 1H), 7.00 (t, J=8.0 Hz, 1H), 3.84 (s, 3H), 3.80 (s, 3H), 2.53 (m, 2H), 2.36 (q, J=7.8 Hz, 2H), 1.86 (m, 2H)

$^{13}$C NMR (75 MHz, $CDCl_3$): δ 201.4, 165.7, 164.2, 148.7, 128.9, 52.4, 52.4, 42.7, 28.9, 20.5

HRMS (ESI+) calcd for $C_{10}H_{15}O_5^+$, $[M+H]^+$215.0919, found 215.0917.

21b

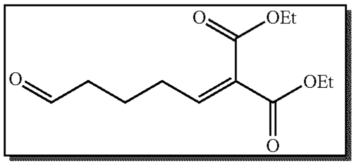

Colorless oil, yield 43% (two step) after silica gel chromatography (EtOAc/Hexane=15:85).

$^{1}$H-NMR (300 MHz, $CDCl_3$): δ 9.79 (s, 1H), 6.95 (t, J=8.0 Hz, 1H), 4.22-4.35 (m, 4H), 2.49-2.54 (m, 2H), 2.37 (q, J=7.3 Hz, 2H), 1.85 (t, J=7.3 Hz, 2H), 1.29-1.76 (m, 6H)

$^{13}$C-NMR (75 MHz, $CDCl_3$): δ 201.4, 165.3, 163.8, 147.6, 129.7, 61.4, 42.8, 28.8, 20.5, 14.1, 14.1 HRMS (ESI+) calcd for $C_{12}H_{19}O_5^+$, $[M+H]^+$243.1232, found 243.1229.

21c

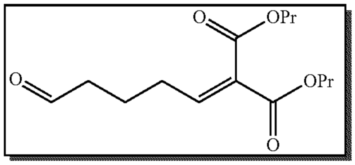

Colorless oil, yield 42% (two step) after silica gel chromatography (EtOAc/Hexane=15:85).

$^{1}$H-NMR (300 MHz, $CDCl_3$): δ 9.67 (t, J=2.4 Hz, 1H), 6.84 (t, J=8.0 Hz, 1H), 4.09 (t, J=6.6 Hz, 2H), 4.04 (t, J=6.6 Hz, 2H), 2.41 (dt, $J_1$=1.2 Hz, $J_2$=14.7 Hz, 2H), 2.25 (q, J=7.5 Hz, 2H), 1.53-1.78 (m, 6H), 0.86 (q, J=7.5 Hz, 6H)

$^{13}$C-NMR (75 MHz, $CDCl_3$): δ 201.2, 165.3, 163.7, 147.4, 129.6, 66.8, 66.7, 42.7, 28.7, 21.8, 21.8, 20.4, 10.3, 10.2

HRMS (ESI+) calcd for $C_{14}H_{23}O_5^+$, $[M+H]^+$271.1545, found 271.1547

21d

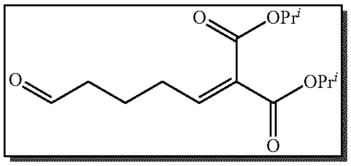

Colorless oil, yield 41% (two step) after silica gel chromatography (EtOAc/Hexane=15:85).

$^{1}$H-NMR (300 MHz, $CDCl_3$): δ 9.73 (s, 1H), 6.83 (t, J=15.9 Hz, 1H), 5.00-5.15 (m, 2H), 2.43-2.48 (m, 2H), 2.25-2.33 (m, 2H), 1.76-1.81 (m, 2H), 1.23 (d, J=7.2 Hz, 6H), 1.26 (d, J=7.2 Hz, 6H)

$^{13}$C-NMR (75 MHz, $CDCl_3$): δ 201.3, 164.9, 163.3, 146.5, 130.4, 68.9, 68.9, 42.8, 28.6, 21.7 (2C), 20.5 (2C)

HRMS (ESI+) calcd for $C_{14}H_{23}O_5^+$, $[M+H]^+$271.1545, found 271.1550

21e

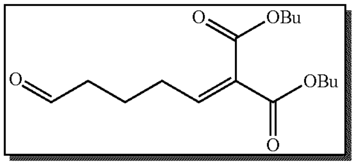

Colorless oil, yield 45% (two step) after silica gel chromatography (EtOAc/Hexane=15:85).

$^{1}$H-NMR (300 MHz, $CDCl_3$): δ 9.75 (t, J=2.4 Hz, 1H), 6.90 (t, J=15.9 Hz, 1H), 4.15-4.23 (m, 4H), 2.45-2.50 (m, 2H), 2.31 (q, J=7.5 Hz, 2H), 1.81-1.86 (m, 2H), 1.59-1.67 (m, 4H), 1.31-1.49 (m, 4H), 0.86 (q, J=7.5 Hz, 6H)

$^{13}$C-NMR (75 MHz, $CDCl_3$): δ 201.3, 165.4, 163.8, 147.5, 129.7, 65.2, 42.8, 30.5, 30.5, 28.8, 20.5, 19.0, 13.6, 13.6

HRMS (ESI+) calcd for $C_{16}H_{27}O_5^+$, $[M+H]^+$299.1858, found 299.1857.

21f

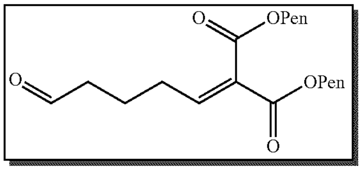

Colorless oil, yield 47% (two step) after silica gel chromatography (EtOAc/Hexane=15:85).

$^{1}$H-NMR (400 MHz, $CDCl_3$): δ 9.66 (s, 1H), 6.83 (t, J=8.0 Hz, 1H), 4.11 (t, J=6.6 Hz, 2H), 2.40 (t, J=7.1 Hz, 2H), 2.24 (q, J=7.1 Hz, 2H), 1.76 (m, 2H), 1.54-1.60 (m, 4H), 1.23-1.26 (m, 8H), 0.80-0.81 (m, 6H)

$^{13}$C-NMR (100 MHz, $CDCl_3$): δ 201.2, 165.4, 163.7, 147.4, 129.7, 65.4, 65.4, 42.7, 28.7, 28.1, 28.1, 27.9, 27.9, 22.2, 20.4, 13.8

HRMS (ESI+) calcd for $C_{18}H_{31}O_5^+$, $[M+H]^+$327.2171, found 327.2168.

21g

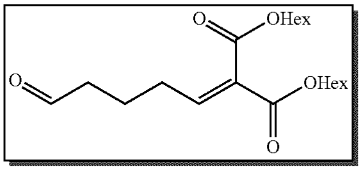

Colorless oil, yield 48% (two step) after silica gel chromatography (EtOAc/Hexane=15:85).

$^1$H-NMR (400 MHz, $CDCl_3$): δ 9.65 (s, 1H), 6.82 (t, J=8.0 Hz, 1H), 4.10 (t, J=6.6 Hz, 2H), 4.06 (t, J=6.6 Hz, 2H), 2.39 (t, J=7.4 Hz, 2H), 2.23 (q, J=7.4 Hz, 2H), 1.72 (m, 2H), 1.51-1.61 (m, 4H), 1.13-1.28 (m, 12H), 0.76-0.79 (m, 6H)

$^{13}$C-NMR (100 MHz, $CDCl_3$): δ 201.2, 165.3, 163.7, 147.4, 129.7, 65.4, 65.3, 42.7, 31.3, 28.7, 28.4, 28.4, 25.5, 25.4, 22.4, 22.4, 20.4, 13.9

HRMS (ESI+) calcd for $C_{20}H_{35}O_5^+$, $[M+H]^+$355.2484, found 355.2485

General Procedure for Synthesis of Nitrosobenzene Derivatives (Defoin, A., Synthesis (2004) 706-710)

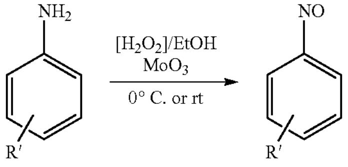

R' = 3-Me, 4-Me, 3-Cl, 4-Cl, 4-Br, 4-OPh

To a stirred solution of aniline (10 mmol) in MeOH (3 mL) were added $H_2O_2$ (5.5 mL, 40 mmol, 4 equiv) and $H_2O$ (4.5 mL). Aniline precipitated as fine crystals and then $MoO_3$ (144 mg, 1 mmol) and aqueous KOH solution (1 mL, 1 mmol) were added and the solution stirred at 0° C. The solution became brown and then yellow with formation of a precipitate, pH value 3-3.5. The reaction was monitored by $^1$H NMR in $CDCl_3$. After the reaction finished, $H_2O$ (15 mL) was added and extracted with DCM 50 mL×3, dried with anhydrous $MgSO_4$, concentrated and purified by column chromatography (EtOAc/Hexane=5:95) on silica gel to give the niroso-benzene derivatives as a yellow solid.

2c

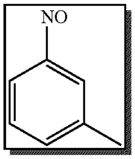

Prepared according to the general procedures as a yellow solid, yield 67% after silica gel chromatography.

$^1$H-NMR (500 MHz, $CDCl_3$): δ7.78 (d, J=6.5 Hz, 1H), 7.64 (s, 1H), 7.49-7.54 (m, 2H), 2.51 (s, 3H)

$^{13}$C-NMR (125 MHz, $CDCl_3$): δ 166.3, 139.5, 136.3, 129.1, 120.9, 119.1, 21.2

HRMS (EI+) calcd for $C_7H_7NO$, $[M]^+$ 121.0522, found 121.0524.

2e

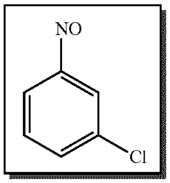

Prepared according to the general procedures as a yellow solid, yield 61% after silica gel chromatography.

$^1$H-NMR (500 MHz, $CDCl_3$): δ 8.06 (dt, $J_1$=1.4 Hz, $J_2$=7.8 Hz, 1H), 7.69 (m, 1H), 7.61-7.64 (m, 2H)

$^{13}$C-NMR (125 MHz, $CDCl_3$): δ 165.1, 136.0, 135.0, 130.8, 121.5, 118.7

HRMS (EI+) calcd for $C_6H_4ClNO$, $[M]^+$ 140.9976, found 140.9974

The $^1$H-NMR of 4-Me, 4-Cl, 4-Br nitosobenzenes are consistent with literature (Defoin, 2004, supra) reported.

The $^1$H-NMR of 4-OPh nitrosobenzene is consistent with literature (Momiyama, N, et al., J. Am. Chem. Soc. (2007) 129, 1190-1195) reported.

General Procedure for the Tandem Aminoxylation-Michael Addition Reaction

In a 5 mL vial equipped with stirring bar, dimethyl 2-(5-oxopentylidene)malonate (63 mg, 0.3 mmol) was dissolved in 1 mL of $CH_3CN$. The mixture was then cooled to −78° C. for 5 min, L-Proline (1.2 mg, 0.01 mmol) and nitrosobenzene (10.7 mg, 0.1 mmol) was added in one portion. The resulted mixture was then stirred at −20° C. and monitored by TLC, after complete consumption of the nitrosobenzene, the solvent was removed under vacuum, 5 mL of $H_2O$ was added, and extracted with ethyl acetate 10 mL three times. The combined organic layers were washed with brine, dried over anhydrous $Na_2SO_4$ and concentrated under vacuum after filtration. Purification by flash column chromatography (silica gel, Hexane/EtOAc) afforded the product 26 mg (84%). The ee value was measured by HPLC on a chiral phase HPLC: Chiral-AS-H column, λ=254 nm, i-PrOH/hexane=5:95, flow rate=1.0 mL/min, $t_1$=12.99 min (major), $t_2$=13.72 min (minor), 98% ee.

23a

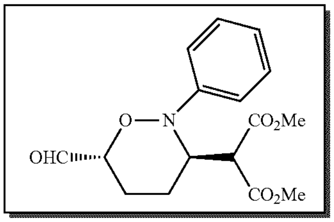

Prepared according to the general procedure, got a colorless oil, 27 mg, yield 84% after silica gel chromatography, eluent (EtOAc/Hexane=5:95-15:85).

$^1$H-NMR (300 MHz, $CDCl_3$): δ 9.68 (d, J=1.2 Hz, 1H), 7.25-7.31 (m, 2H), 7.09-7.12 (m, 2H), 6.98 (t, J=7.5 Hz, 2H), 4.49-4.60 (m, 2H), 4.28 (d, J=9.0 Hz, 1H), 3.66 (s, 3H), 3.10 (s, 3H), 2.02-2.18 (m, 3H), 1.78-1.80 (m, 1H)

$^{13}$C-NMR (75 MHz, $CDCl_3$): δ 203.1, 168.2, 167.5, 147.6, 128.6 (2C), 122.7, 116.0 (2C), 82.9, 59.1, 52.8, 52.2, 49.4, 23.8, 19.2

HRMS (ESI−) calcd for $C_{16}H_{18}NO_6^-$, $[M-H]^-$ 320.1134, found 320.1133

The enantiomeric excess was determined by HPLC analysis employing a Daicel Chiracel AS-H column (Hexane/i-propanol=95:5, 1 mL/min): $t_1$=12.99 min (major), $t_2$=13.72 min (minor). (>98% ee) $[\alpha]^{25}_D$: −6.17 (c=0.51, $CHCl_3$).

23b

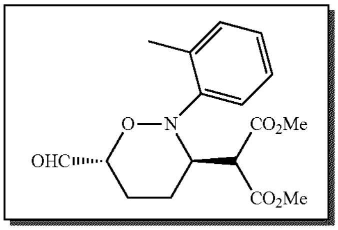

Prepared according to the general procedure, got a colorless oil, 23 mg, yield 70% after silica gel chromatography, eluent (EtOAc/Hexane=5:95-15:85)

$^1$H-NMR (300 MHz, $CDCl_3$): δ 9.75 (s, 1H), 7.35 (d, J=7.8 Hz, 1H), 7.14-7.19 (t, J=6.6 Hz, 2H), 7.03-7.08 (m, 1H), 4.46-4.47 (m, 1H), 4.34-4.37 (m, 1H), 4.23-4.27 (m, 1H), 3.73 (s, 3H), 3.22 (s, 3H), 2.25 (s, 3H), 2.03-2.20 (m, 3H), 1.69-1.70 (m, 1H)

$^{13}$C-NMR (75 MHz, $CDCl_3$): δ 203.1, 168.3, 167.5, 146.3, 130.74 (2C), 125.9, 125.3, 119.6, 83.0, 58.3, 52.8, 52.3, 49.5, 23.6, 19.4, 17.6

HRMS (ESI−) calcd for $C_{17}H_{20}NO_6^-$, $[M-H]^-$ 334.1291, found 334.1291.

The enantiomeric excess was determined by HPLC analysis employing a Daicel Chiracel AS-H column (Hexane/i-propanol=99:1, 1.0 mL/min): $t_1$=17.02 min (minor), $t_2$=19.42 min (major). (94% ee)

$[\alpha]^{25}_D$: −10.57 (c=0.71, $CHCl_3$)

23c

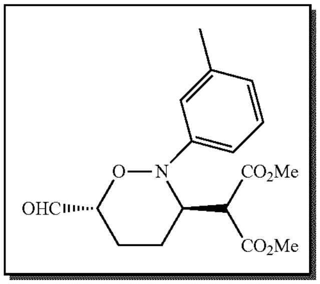

Prepared according to the general procedure, got a colorless oil, 21 mg, yield 63% after silica gel chromatography, eluent (EtOAc/Hexane=5:95-15:85).

$^1$H-NMR (500 MHz, $CDCl_3$): δ 9.69 (s, 1H), 7.18 (t, J=8.1 Hz, 1H), 6.93 (t, J=8.1 Hz, 2H), 6.81 (d, J=8.1 Hz, 1H), 4.56 (d, J=8.5 Hz, 2H), 4.51 (d, J=3.2 Hz, 1H), 4.28 (d, J=8.5 Hz, 1H), 3.77 (s, 3H), 3.14 (s, 3H), 2.35 (s, 3H), 2.04-2.15 (m, 3H), 1.78-1.80 (m, 1H)

$^{13}$C-NMR (125 MHz, $CDCl_3$): δ 203.2, 168.3, 167.5, 147.7, 138.4, 128.5, 123.5, 116.7, 113.3, 82.9, 59.1, 52.8, 52.1, 49.4, 23.8, 21.6, 19.3

HRMS (ESI−) calcd for $C_{17}H_{20}NO_6^-$, $[M-H]^-$ 334.1291, found 334.1295

The enantiomeric excess was determined by HPLC analysis employing a Daicel Chiracel AD-H column (Hexane/i-propanol=95:5, 1.0 mL/min): $t_1$=14.90 min (minor), $t_2$=18.17 min (major). (98% ee)

$[\alpha]^{25}_D$: −59.13 (c=1.2, $CHCl_3$)

23d

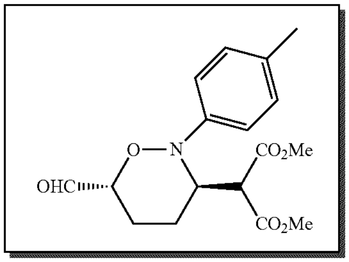

Prepared according to the general procedure, got a colorless oil, 24 mg yield 73% after silica gel chromatography, eluent (EtOAc/Hexane=5:95-15:85).

$^1$H-NMR (400 MHz, $CDCl_3$): δ 9.64 (d, J=1.0 Hz, 1H), 7.07 (d, J=8.6 Hz, 2H), 6.98 (d, J=8.6 Hz, 2H), 4.45-4.48 (m, 2H), 4.22 (d, J=9.3 Hz, 1H), 3.73 (s, 3H), 3.12 (s, 3H), 2.26 (s, 3H), 2.00-2.09 (m, 3H), 1.74-1.78 (m, 1H)

$^{13}$C-NMR (100 MHz, $CDCl_3$): δ 203.2, 168.3, 167.6, 145.3, 132.4, 129.1 (2C), 116.6 (2C), 82.9, 59.5, 52.8, 52.2, 49.5, 23.8, 20.6, 19.4

HRMS (ESI−) calcd for $C_{17}H_{20}NO_6^-$, $[M-H]^-$ 334.1291, found 334.1292.

The enantiomeric excess was determined by HPLC analysis employing a Daicel Chiracel AS-H column (Hexane/i-propanol=95:5, 1.0 mL/min): $t_1$=12.81 min (major), $t_2$=17.86 min (minor). (99% ee)

$[\alpha]^{25}_D$: −53.67 (c=1.2, $CHCl_3$)

23e

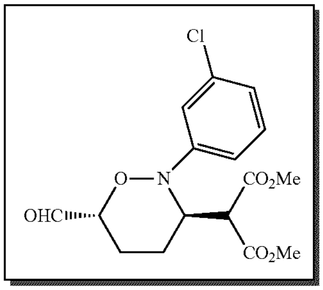

Prepared according to the general procedure, got a colorless oil, 23 mg, yield 65% after silica gel chromatography, eluent (EtOAc/Hexane=5:95-15:85).

$^1$H-NMR (400 MHz, $CDCl_3$): δ 9.65 (s, 1H), 7.16-7.21 (m, 2H), 6.92 (t, J=8.4 Hz, 2H), 4.55 (d, J=9.2 Hz, 2H), 4.50 (d, J=4 Hz, 1H), 4.26 (d, J=9.2 Hz, 1H), 3.75 (s, 3H), 3.18 (s, 3H), 2.05-2.15 (m, 3H), 1.77-1.79 (m, 1H)

$^{13}$C-NMR (100 MHz, $CDCl_3$): δ 202.7, 168.0, 167.3, 148.8, 134.6, 129.6, 122.4, 115.8, 114.0, 83.1, 58.9, 52.9, 52.3, 49.3, 23.66, 19.0

HRMS (ESI−) calcd for $C_{16}H_{17}ClNO_6^-$, $[M-H]^-$ 354.0776, found 354.0772

The enantiomeric excess was determined by HPLC analysis employing a Daicel Chiracel AD-H column (Hexane/i-propanol=95:5, 1.0 mL/min): $t_1$=17.73 min (minor), $t_2$=27.99 min (major). (98% ee)

$[\alpha]^{25}_D$: −11.79 (c=1.0, $CHCl_3$)

23f

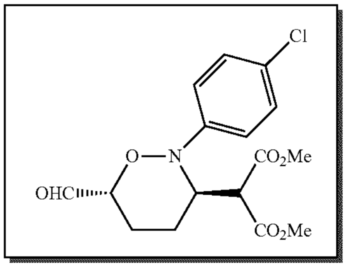

Prepared according to the general procedure, got a colorless oil, 22 mg, yield 62% after silica gel chromatography, eluent (EtOAc/Hexane=5:95-15:85)

$^1$H-NMR (400 MHz, $CDCl_3$): δ 9.63 (s, 1H), 7.23 (d, J=8.8 Hz, 2H), 7.03 (d, J=8.8 Hz, 2H), 4.48-4.53 (m, 2H), 4.24 (d, J=9.2 Hz, 1H), 3.74 (s, 3H), 3.16 (s, 3H), 2.01-2.13 (m, 3H), 1.75-1.79 (m, 1H)

$^{13}$C-NMR (100 MHz, $CDCl_3$): δ 202.8, 168.0, 167.4, 146.2, 128.6 (2C), 127.7, 117.4 (2C), 83.0, 59.1, 52.9, 52.3, 49.4, 23.7, 19.1

HRMS (ESI-) calcd for $C_{16}H_{17}ClNO_6^-$, $[M-H]^-$ 354.0776, found 354.0772

The enantiomeric excess was determined by HPLC analysis employing a Daicel Chiracel AS-H column (Hexane/i-propanol=95:5, 1.0 mL/min): $t_1$=17.90 min (major), $t_2$=26.08 min (minor). (99% ee)

$[\alpha]^{25}_D$: −34.46 (c=1.1, $CHCl_3$)

23g

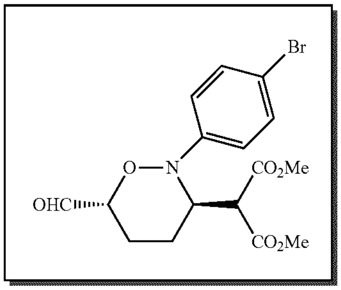

Prepared according to the general procedure, got a colorless oil, 29 mg, yield 72% after silica gel chromatography, eluent (EtOAc/Hexane=5:95-15:85).

$^1$H-NMR (300 MHz, $CDCl_3$): δ 9.65 (s, 1H), 7.40 (d, J=9.0 Hz, 2H), 7.01 (d, J=9.0 Hz, 2H), 4.50-4.56 (m, 2H), 4.26 (d, J=9.0 Hz, 1H), 3.73 (s, 3H), 3.18 (s, 3H), 2.05-2.16 (m, 3H), 1.70-1.80 (m, 1H)

$^{13}$C-NMR (75 MHz, $CDCl_3$): δ 202.7, 168.0, 167.4, 146.7, 131.5 (2C), 117.6 (2C), 115.2, 83.0, 59.0, 52.9, 52.3, 49.4, 23.7, 19.0

HRMS (ESI-) calcd for $C_{16}H_{17}BrNO_6^-$, $[M-H]^-$ 398.0239, found 398.0234

The enantiomeric excess was determined by HPLC analysis employing a Daicel Chiracel AS-H column (Hexane/i-propanol=95:5, 1.0 mL/min): $t_1$=17.28 min (major), $t_2$=19.42 min (minor). (>99% ee)

$[\alpha]^{25}_D$: −26.52 (c=1.2, $CHCl_3$).

23h

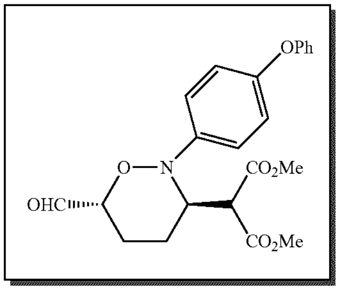

Prepared according to the general procedure, got a colorless oil, 21 mg, yield 52% after silica gel chromatography, eluent (EtOAc/Hexane=5:95-15:85)

$^1$H-NMR (400 MHz, $CDCl_3$): δ 9.69 (s, 1H), 7.31 (t, J=8.0 Hz, 2H), 7.07-7.09 (m, 3H), 6.94-6.97 (m, 4H), 4.44-4.48 (m, 2H), 4.23 (d, J=9.2 Hz, 1H), 3.75 (s, 3H), 3.27 (s, 3H), 2.01-2.14 (m, 3H), 1.76-1.79 (m, 1H)

$^{13}$C-NMR (100 MHz, $CDCl_3$): δ 202.9, 168.1, 167.5, 157.8, 152.5, 143.6, 129.7 (2C), 123.0 (2C), 119.5 (2C), 118.4, 118.2 (2C), 83.0, 60.0, 52.8, 52.4, 49.5, 23.9, 19.4

HRMS (ESI-) calcd for $C_{22}H_{22}NO_7^-$, $[M-H]^-$ 412.1396, found 412.1401

The enantiomeric excess was determined by HPLC analysis employing a Daicel Chiracel AS-H column (Hexane/i-propanol=95:5, 1.0 mL/min): t=22.85 min (major). (99% ee) $[\alpha]^{25}_D$: −14.17 (c=1.0, $CHCl_3$)

23i

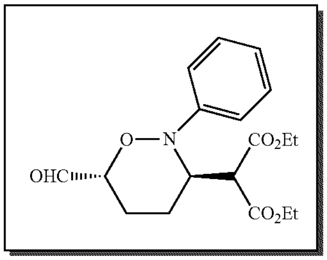

Prepared according to the general procedure, got a colorless oil, 25 mg, yield 73% after silica gel chromatography, eluent (EtOAc/Hexane=5:95-15:85)

$^1$H-NMR (300 MHz, $CDCl_3$): δ 9.69 (s, 1H), 7.27 (t, J=8.1 Hz, 2H), 7.12 (t, J=8.1 Hz, 2H), 6.96 (t, J=7.2 Hz, 1H), 4.58 (d, J=8.7 Hz, 1H), 4.49 (s, 1H), 4.18-4.25 (m, 3H), 3.51 (q, J=7.2 Hz, 2H), 2.06-2.14 (m, 3H), 1.82-1.84 (m, 1H), 1.28 (t, J=7.2, 3H), 1.00 (t, J=7.2 Hz, 3H)

$^{13}$C-NMR (75 MHz, $CDCl_3$): δ 203.3, 167.9, 167.2, 147.8, 128.5 (2C), 122.7, 116.3 (2C), 82.9, 61.7, 61.4, 59.1, 49.9, 23.7, 19.3, 14.0, 13.6

HRMS (ESI-) calcd for $C_{18}H_{22}NO_6$, $[M-H]^-$ 348.1447, found 348.1446

The enantiomeric excess was determined by HPLC analysis employing a Daicel Chiracel AS-H column (Hexane/i-propanol=99:1, 1.0 mL/min): $t_1$=7.09 min (major), $t_2$=10.20 min (minor). (99% ee)

$[\alpha]^{25}_D$: −66.57 (c=1.1, $CHCl_3$)

23j

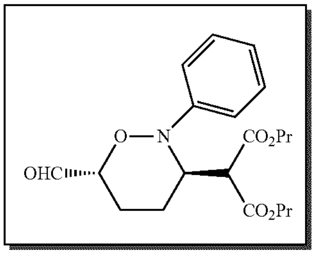

Prepared according to the general procedure, got a colorless oil, 30 mg, yield 81% after silica gel chromatography, eluent (EtOAc/Hexane=5:95-15:85)

$^1$H-NMR (300 MHz, $CDCl_3$): δ 9.69 (s, 1H), 7.26-7.30 (m, 2H), 7.11-7.13 (m, 2H), 6.98 (t, J=7.5 Hz, 1H), 4.58 (d, J=8.7 Hz, 1H), 4.49 (s, 1H), 4.24 (d, J=9 Hz, 1H), 4.16 (t, J=7.2 Hz, 2H), 3.41 (t, J=7.2 Hz, 2H), 2.06-2.14 (m, 3H), 1.82-1.84 (m, 1H), 1.64-1.72 (m, 4H), 1.40-1.42 (m, 2H) 0.92 (t, J=7.2, 3H), 0.86 (t, J=7.2, 3H)

$^{13}$C-NMR (75 MHz, $CDCl_3$): δ 203.3, 168.0, 167.3, 147.2, 128.5 (2C), 122.7, 116.3 (2C), 82.9, 67.3, 67.0, 59.1, 49.9, 23.7, 21.9, 21.8, 21.4, 19.3, 10.3, 10.2

HRMS (ESI−) calcd for $C_{20}H_{26}NO_6^-$, [M−H]$^-$ 376.1760, found 376.1758

The enantiomeric excess was determined by HPLC analysis employing a Daicel Chiracel AS-H column (Hexane/i-propanol=95:5, 1.0 mL/min): $t_1$=7.43 min (major), $t_2$=9.80 min (minor). (99% ee)

$[\alpha]^{25}_D$: −38.28 (c=0.9, $CHCl_3$)

23k

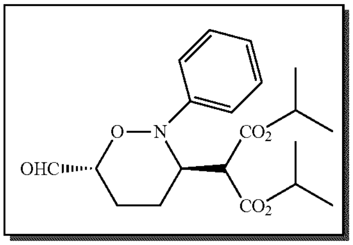

Prepared according to the general procedure, got a colorless oil, 26 mg, yield 69% after silica gel chromatography, eluent (EtOAc/Hexane=5:95-15:85).

$^1$H-NMR (300 MHz, $CDCl_3$): δ 9.68 (s, 1H), 7.25 (t, J=7.8 Hz, 2H), 7.11 (d, J=7.8 Hz, 2H), 6.98 (t, J=14.7 Hz, 1H), 5.01-5.09 (m, 1H), 4.54 (d, J=8.1 Hz, 1H), 4.46 (s, 1H), 4.35-4.46 (m, 1H), 4.10 (d, J=5.4 Hz, 1H), 2.03-2.17 (m, 3H), 1.84-1.88 (m, 1H), 1.24 (d, J=6.3 Hz, 3H), 1.01 (d, J=6.3 Hz, 3H), 0.92 (d, J=7.2 Hz, 3H).

$^{13}$C-NMR (75 MHz, $CDCl_3$): δ 203.4, 167.5, 166.8, 148.0, 128.5 (2C), 123.0, 116.9 (2C), 82.9, 69.3, 69.2, 59.2, 50.4, 34.2, 23.6, 21.5, 21.3, 21.2, 19.5

HRMS (ESI−) calcd for $C_{20}H_{26}NO_6^-$, [M−H]$^-$ 376.1760, found 376.1758

The enantiomeric excess was determined by HPLC analysis employing a Daicel Chiracel AS-H column (Hexane/i-propanol=99:1, 1.0 mL/min): $t_1$=6.76 min (minor), $t_2$=7.64 min (major). (99% ee) $[\alpha]^{25}_D$: −23.10 (c=1.0, $CHCl_3$)

23l

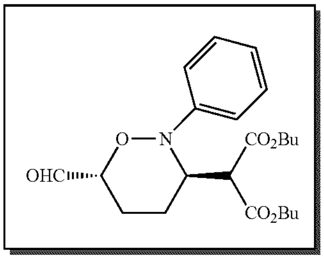

Prepared according to the general procedure, got a colorless oil, 31 mg, yield 79% after silica gel chromatography, eluent (EtOAc/Hexane=5:95-15:85)

$^1$1'-NMR (300 MHz, $CDCl_3$): δ 9.67 (s, 1H), 7.25 (t, J=7.5 Hz, 2H), 7.11 (d, J=7.5 Hz, 2H), 6.96 (t, J=7.5 Hz, 1H), 4.47-4.57 (m, 2H), 4.21 (d, J=9 Hz, 1H), 4.13 (t, J=13.2 Hz, 2H), 3.44 (t, J=13.2 Hz, 2H), 2.04-2.12 (m, 3H), 1.81-1.83 (m, 1H), 1.61-1.63 (m, 2H), 1.17-1.56 (m, 6H), 0.82-0.96 (m, 6H)

$^{13}$C-NMR (75 MHz, $CDCl_3$): δ 203.3, 168.0, 167.3, 147.8, 128.5 (2C), 122.7, 116.4 (2C), 82.9, 65.6, 65.3, 59.1, 49.9, 30.4, 30.1, 23.7, 19.3, 19.0, 18.9, 13.7, 13.6

HRMS (ESI−) calcd for $C_{22}H_{30}NO_6^-$, [M−H]$^-$ 404.2073, found 404.2072

The enantiomeric excess was determined by HPLC analysis employing a Daicel Chiracel AS-H column (Hexane/i-propanol=99:1, 1.0 mL/min): $t_1$=7.30 min (major), $t_2$=9.58 min (minor). (99% ee)

$[\alpha]^{25}_D$: −37.25 (c=1.2, $CHCl_3$)

23m

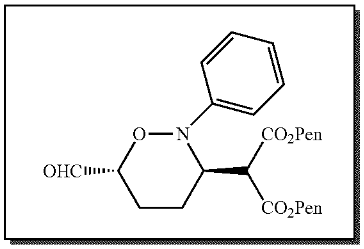

Prepared according to the general procedure, got a colorless oil, 29 mg, yield 67% after silica gel chromatography, eluent (EtOAc/Hexane=5:95-15:85)

$^1$H-NMR (400 MHz, $CDCl_3$): δ 9.67 (s, 1H), 7.26 (t, J=8.0 Hz, 2H), 7.09 (d, J=8.0 Hz, 2H), 6.96 (t, J=8.0 Hz, 1H), 4.55 (d, J=8.7 Hz, 1H), 4.48 (d, J=4.0 Hz, 1H), 4.21 (d, J=8.7 Hz, 1H), 4.12 (t, J=6.6 Hz, 2H), 3.42 (t, J=6.6 Hz, 2H), 2.06-2.08 (m, 3H), 1.80-1.85 (m, 1H), 1.12-1.38 (m, 12H), 0.85-0.91 (m, 6H)

$^{13}$C-NMR (100 MHz, $CDCl_3$): δ 203.4, 168.0, 167.3, 147.8, 128.5 (2C), 122.7, 116.3 (2C), 82.9, 65.9, 65.6, 59.1, 49.9, 28.1, 27.9, 27.8, 27.7, 23.7, 22.2, 19.3, 14.0

HRMS (ESI−) calcd for $C_{24}H_{34}NO_6^-$, [M−H]$^-$ 432.2390, found 432.2388

The enantiomeric excess was determined by HPLC analysis employing a Daicel Chiracel AS-H column (Hexane/i-propanol=95:5, 1.0 mL/min): $t_1$=14.96 min (minor), $t_2$=22.61 min (major). (92% ee)

$[\alpha]^{25}_D$: −40.8 (c=1.2, $CHCl_3$)

23n

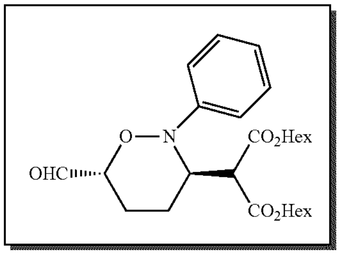

Prepared according to the general procedure, got a colorless oil, 32 mg, yield 71% after silica gel chromatography, eluent (EtOAc/Hexane=5:95-15:85)

$^1$H-NMR (400 MHz, $CDCl_3$): δ 9.67 (s, 1H), 7.26 (t, J=8.0 Hz, 2H), 7.10 (d, J=8.0 Hz, 2H), 6.96 (t, J=8.0 Hz, 1H), 4.47-4.56 (m, 2H), 4.21 (d, J=8.7 Hz, 1H), 4.12 (t, J=6.6 Hz, 2H), 3.42 (t, J=6.6 Hz, 2H), 2.04-2.11 (m, 3H), 1.81-1.85 (m, 1H), 1.56-1.63 (m, 2H), 1.19-1.38 (m, 14H), 0.85-0.91 (m, 6H)

$^{13}$C-NMR (100 MHz, $CDCl_3$): δ 203.4, 168.0, 167.3, 147.8, 128.5 (2C), 122.7, 116.3 (2C), 82.9, 65.9, 65.6, 59.1, 49.9, 31.4, 28.3, 28.0, 25.5, 25.4, 23.73, 22.5, 19.3, 14.0

HRMS (ESI−) calcd for $C_{26}H_{38}NO_6^-$, $[M-H]^-$ 460.2704, found 460.2699

The enantiomeric excess was determined by HPLC analysis employing a Daicel Chiracel AD-H column (Hexane/i-propanol=98:2, 1.0 mL/min): t=5.10 min (major). (99% ee) $[\alpha]^{25}_D$: −14.41 (c=0.7, $CHCl_3$)

23o

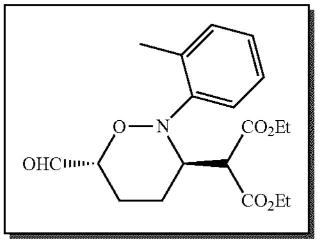

Prepared according to the general procedure, got a colorless oil, 26 mg, yield 73% after silica gel chromatography, eluent (EtOAc/Hexane=5:95-15:85)

$^1$H-NMR (300 MHz, $CDCl_3$): δ 9.74 (s, 1H), 7.35 (m, 1H), 7.11-7.15 (m, 2H), 7.02 (t, J=6.9 Hz, 1H), 4.43-4.45 (m, 1H), 4.11-4.27 (m, 4H), 3.52-3.65 (m, 2H), 2.22 (s, 3H), 2.03-2.09 (m, 3H), 1.68-1.71 (m, 1H), 1.26 (t, J=7.2 Hz, 3H), 1.00 (t, J=7.2 Hz, 3H)

$^{13}$C-NMR (75 MHz, $CDCl_3$): δ 203.2, 168.1, 167.1, 146.5, 130.7 (2C), 125.9, 125.3, 119.6, 83.0, 61.7, 61.4, 58.1, 49.9, 23.5, 17.7, 14.0, 13.7

HRMS (ESI−) calcd for $C_{19}H_{24}NO_6^-$, $[M-H]^-$ 362.1604, found 362.1599

The enantiomeric excess was determined by HPLC analysis employing a Daicel Chiracel AD-H column (Hexane/i-propanol=97:3, 1.0 mL/min): $t_1$=12.72 min (major), $t_2$=14.63 min (minor), (>95% ee)

$[\alpha]^{25}_D$: −23.6 (c=1.1, $CHCl_3$)

23p

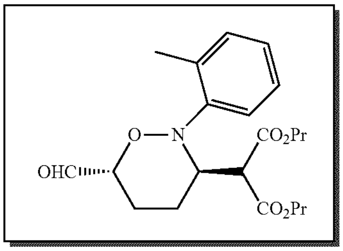

Prepared according to the general procedure, got a colorless oil, 28 mg, yield 72% after silica gel chromatography, eluent (EtOAc/Hexane=5:95-15:85)

$^1$H-NMR (300 MHz, $CDCl_3$): δ 9.74 (s, 1H), 7.34 (d, J=7.8 Hz, 1H), 7.03-7.15 (m, 2H), 7.04 (t, J=7.8 Hz, 1H), 4.44-4.46 (m, 1H), 4.12-4.29 (m, 2H), 4.04-4.11 (m, 2H), 3.45-3.54 (m, 2H), 2.23 (s, 3H), 2.05-2.17 (m, 3H), 1.62-1.72 (m, 1H), 1.38-1.45 (m, 2H), 0.92 (t, J=7.5 Hz, 3H), 0.819 (t, J=7.5 Hz, 3H)

$^{13}$C-NMR (75 MHz, $CDCl_3$): δ 203.2, 168.1, 167.2, 146.5, 130.7 (2C), 125.9, 125.3, 119.6, 83.0, 67.3, 67.0, 58.1, 49.9, 23.6, 21.8, 21.5, 17.7, 10.3, 10.2

HRMS (ESI−) calcd for $C_{21}H_{28}NO_6^-$, $[M-H]^-$ 390.1917, found 390.1916

The enantiomeric excess was determined by HPLC analysis employing a Daicel Chiracel AD-H column (Hexane/i-propanol=97:3, 1.0 mL/min): $t_1$=13.77 min (minor), $t_2$=17.06 min (major) (98% ee)

$[\alpha]^{25}_D$: −8.58 (c=0.90, $CHCl_3$)

23q

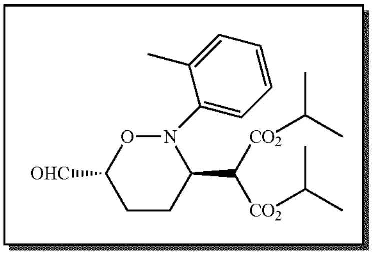

Prepared according to the general procedure, got a colorless oil, 27 mg, yield 69% after silica gel chromatography, eluent (EtOAc/Hexane=5:95-15:85)

$^1$H-NMR (300 MHz, $CDCl_3$): δ 9.75 (s, 1H), 7.33 (d, J=7.8 Hz, 1H), 7.12-7.13 (m, 2H), 7.03 (t, J=6.9 Hz, 1H), 5.04-5.10 (m, 1H), 4.40-4.44 (m, 2H), 4.23 (s, 2H), 2.23 (s, 3H), 2.03-2.14 (m, 3H), 1.71-1.73 (m, 1H), 1.24 (d, J=7.2 Hz, 3H), 1.23 (d, J=7.2 Hz, 3H), 0.99 (d, J=7.2 Hz, 6H), 0.98 (d, J=7.2 Hz, 3H).

$^{13}$C-NMR (75 MHz, $CDCl_3$): δ 203.4, 167.7, 165.7, 146.7, 130.7 (2C), 125.9, 125.3, 119.6, 83.0, 69.3, 69.0, 57.7, 50.1, 23.4, 21.6, 21.4, 21.4, 21.2, 17.7

HRMS (ESI−) calcd for $C_{21}H_{28}NO_6^-$, $[M-H]^-$ 390.1917, found 390.1916

The enantiomeric excess was determined by HPLC analysis employing a Daicel Chiracel AD-H column (Hexane/i-propanol=97:3, 1.0 mL/min): $t_1$=8.34 min (minor), $t_2$=9.77 min (major). (>95% ee)

$[\alpha]^{25}_D$: −12.36 (c=0.90, $CHCl_3$)

23r

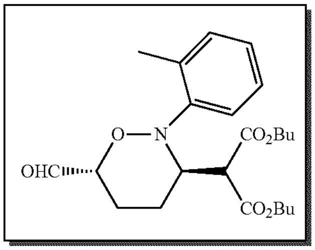

Prepared according to the general procedure, obtained a colorless oil, 29 mg, yield 71% after silica gel chromatography, eluent (EtOAc/Hexane=5:95-15:85).

$^1$H-NMR (300 MHz, $CDCl_3$): δ 9.74 (s, 1H), 7.34 (d, J=7.8 Hz, 1H), 7.02-7.15 (m, 2H), 7.06 (t, J=8.1 Hz, 1H), 4.44-4.45 (m, 1H), 4.21-4.28 (m, 2H), 4.05-4.18 (m, 2H), 3.45-3.60 (m, 2H), 2.22 (s, 3H), 2.04-2.09 (m, 3H), 1.61-1.63 (m, 4H), 1.20-1.40 (m, 6H), 0.84-0.94 (m, 6H)

$^{13}$C-NMR (75 MHz, $CDCl_3$): δ 203.2, 168.1, 167.2, 139.6, 130.7 (2C), 125.9, 125.7, 119.5, 83.0, 65.6, 65.3, 58.1, 49.8, 30.4, 30.1, 23.6, 19.32, 19.0, 19.0, 17.7, 13.7, 13.6

HRMS (ESI−) calcd for $C_{23}H_{32}NO_6^-$, $[M-H]^-$ 418.2230, found 418.2229

The enantiomeric excess was determined by HPLC analysis employing a Daicel Chiracel AD-H column (Hexane/i-propanol=97:3, 1.0 mL/min): $t_1$=8.79 min (minor), $t_2$=11.30 min (major). (96% ee)

$[\alpha]^{25}_D$: −25.24 (c=0.71, $CHCl_3$)

23s

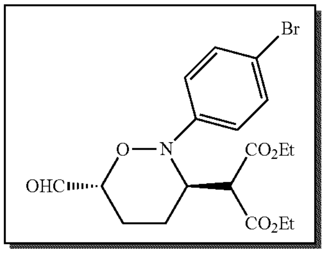

Prepared according to the general procedure, obtained a colorless oil, 28 mg, yield 67% after silica gel chromatography, eluent (EtOAc/Hexane=5:95-15:85).

$^1$H-NMR (300 MHz, $CDCl_3$): δ 9.66 (s, 1H), 7.38 (d, J=9.0 Hz, 2H), 7.01 (d, J=9.0 Hz, 2H), 4.49-4.56 (m, 2H), 4.18-4.23 (m, 3H), 3.60 (q, J=7.2 Hz, 2H), 2.05-2.15 (m, 3H), 1.82-1.84 (m, 1H), 1.29 (t, J=6.9 Hz, 3H), 1.05 (t, J=6.9 Hz, 3H)

$^{13}$C-NMR (75 MHz, $CDCl_3$): δ 202.8, 167.7, 167.1, 146.9, 131.4 (2C), 117.9 (2C), 115.3, 83.0, 61.8, 61.6, 59.0, 49.8, 23.6, 19.1, 14.0, 13.6

HRMS (ESI−) calcd for $C_{18}H_{21}BrNO_6^-$, $[M-H]^-$ 426.0552, found 426.0557

The enantiomeric excess was determined by HPLC analysis employing a Daicel Chiracel AS-H column (Hexane/i-propanol=95:5, 1.0 mL/min): $t_1$=8.99 min (major), $t_2$=13.75 min (minor). (99% ee)

$[\alpha]^{25}_D$: −26.52 (c=1.2, $CHCl_3$).

23t

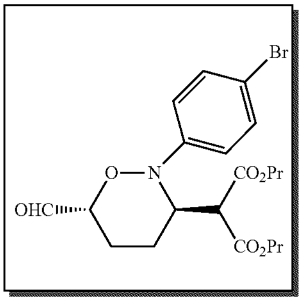

Prepared according to the general procedure, obtained a colorless oil, 28 mg, yield 67% after silica gel chromatography, eluent (EtOAc/Hexane=5:95-15:85).

$^1$H-NMR (300 MHz, $CDCl_3$): δ 9.64 (s, 1H), 7.36 (d, J=9.0 Hz, 2H), 6.99 (d, J=9.0 Hz, 1H), 4.47-4.54 (m, 2H), 4.14-4.22 (m, 3H), 3.47 (t, J=6.6 Hz, 2H), 2.35 (t, J=7.2 Hz, 2H), 2.05-2.08 (m, 3H), 1.81-1.86 (m, 1H), 1.64-1.70 (m, 4H), 0.92-0.98 (m, 6H)

$^{13}$C-NMR (75 MHz, $CDCl_3$): δ 202.8, 167.8, 167.2, 146.9, 137.3 (2C), 118.0 (2C), 115.3, 83.0, 67.4, 67.2, 59.0, 49.8, 31.6, 29.0, 23.6, 23.5, 21.8, 21.5, 19.2, 14.1, 10.3, 10.2

HRMS (ESI−) calcd for $C_{20}H_{25}BrNO_6^-$, $[M-H]^-$ 454.0866, found 454.0862

The enantiomeric excess was determined by HPLC analysis employing a Daicel Chiracel AS-H column (Hexane/i-propanol=95:5, 1.0 mL/min): $t_1$=7.89 min (major), $t_2$=12.31 min (minor). (99% ee)

$[\alpha]^{25}_D$: −11.81 (c=1.1, $CHCl_3$)

23u

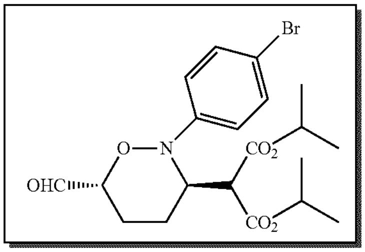

Prepared according to the general procedure, obtained a colorless oil, 30 mg, yield 67% after silica gel chromatography, eluent (EtOAc/Hexane=5:95-15:85).

$^1$H-NMR (300 MHz, $CDCl_3$): δ 9.64 (s, 1H), 7.36 (d, J=9.0 Hz, 2H), 6.99 (d, J=9.0 Hz, 1H), 5.04-5.10 (m, 1H), 4.41-4.47 (m, 2H), 4.26 (s, 2H), 2.25 (s, 3H), 2.06-2.13 (m, 3H), 1.73-1.75 (m, 1H), 0.24 (d, J=7.2 Hz, 6H), 1.01 (d, J=7.2 Hz, 6H)

$^{13}$C-NMR (75 MHz, $CDCl_3$): δ 202.9, 167.3, 166.8, 147.0, 131.4 (2C), 118.4 (2C), 115.6, 83.0, 69.5, 69.4, 65.9, 59.0, 50.3, 23.5, 21.5, 21.3, 21.2, 19.3, 15.2

HRMS (ESI−) calcd for $C_{20}H_{25}BrNO_6^-$, $[M-H]^-$ 454.0866, found 454.0868

The enantiomeric excess was determined by HPLC analysis employing a Daicel Chiracel AD-H column (Hexane/i-propanol=97:3, 1.0 mL/min): $t_1$=15.22 min (minor), $t_2$=26.14 min (major). (99% ee)

$[\alpha]^{25}_D$: −11.26 (c=0.7, $CHCl_3$)

IR Spectra: The infrared spectra were recorded using neat liquid samples for all the tandem reaction products (23a-23v).

All showed the characteristic strong C═O stretches (1690-1745 $cm^{-1}$) for both aldehydes and carboxylic esters.

23v

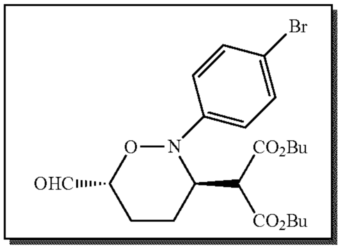

Prepared according to the general procedure, obtained a colorless oil, 34 mg, yield 71% after silica gel chromatography, eluent (EtOAc/Hexane=5:95-15:85).

$^1$H-NMR (300 MHz, $CDCl_3$): δ 9.64 (s, 1H), 7.36 (d, J=9.0 Hz, 2H), 6.98 (d, J=9.0 Hz, 1H), 4.47-4.53 (m, 3H), 4.11-4.23 (m, 5H), 2.17-2.35 (m, 3H), 1.80-1.83 (m, 1H), 1.24-1.39 (m, 8H), 0.85-0.94 (m, 6H)

$^{13}$C-NMR (75 MHz, $CDCl_3$): δ 202.9, 167.8, 167.2, 146.8, 131.4 (2C), 118.0 (2C), 115.5, 83.0, 65.7, 65.5, 59.0, 49.8, 30.4, 30.1, 23.6, 19.0, 18.9, 13.7

HRMS (ESI−) calcd for $C_{22}H_{29}BrNO_6^-$, $[M-H]^-$ 482.1180, found 482.1178

The enantiomeric excess was determined by HPLC analysis employing a Daicel Chiracel AD-H column (Hexane/i-propanol=90:10, 1.0 mL/min): $t_1$=11.45 min (minor), $t_2$=14.63 min (major). (99% ee)

$[\alpha]^{25}_D$: −7.13 (c=1.1, $CHCl_3$)

50i

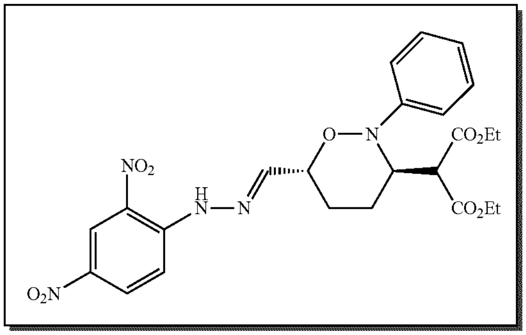

$^1$H-NMR (400 MHz, $CDCl_3$): δ 10.99 (s, 1H), 9.04 (d, J=2.6 Hz, 1H), 8.27 (dd, $J_1$=2.4 Hz, $J_2$=9.6 Hz, 1H), 7.85 (d, J=9.6 Hz, 1H), 7.60 (d, J=2.6 Hz, 1H), 7.24 (t, J=7.9 Hz, 2H), 7.07 (d, J=7.9 Hz, 2H), 6.96 (t, J=7.9 Hz, 1H), 4.93 (s, 1H), 4.51 (m, 1H), 4.20 (q, J=7.1 Hz, 2H), 4.09 (d, J=8.3 Hz, 1H), 3.51-3.62 (m, 2H), 2.20-2.34 (m, 2H), 2.09-2.14 (m, 1H), 1.93-1.97 (m, 1H), 1.26 (t, J=7.1 Hz, 3H), 1.00 (t, J=7.1 Hz, 3H)

$^{13}$C-NMR (100 MHz, $CDCl_3$): δ 167.8, 167.3, 151.1, 147.7, 144.9, 138.2, 130.0, 129.2, 128.6, 123.4, 123.1, 117.3, 116.4, 61.7, 61.5, 59.3, 50.6, 29.7, 23.6, 22.8, 14.0, 13.6

The invention illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A process of enantioselectively forming an aminoxy compound of Formula (3)

(3)

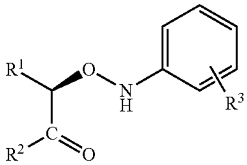

$R^1$ is one of an aliphatic group, an alicyclic group, an aromatic group, an arylaliphatic group and an arylalicyclic group, comprising 0 to about 3 heteroatoms independently selected from the group consisting of N, O, S, Se and Si, wherein $R^2$ is one of hydrogen, an aliphatic group and an alicyclic group, comprising 0 to about 3 heteroatoms independently selected from the group consisting of N, O, S, Se and Si, and $R^3$ is one of hydrogen, halogen, hydroxyl, and an aliphatic group with a main chain having 1 to about 10 carbon atoms and 0 to about 3 heteroatoms independently selected from the group consisting of N, O, S, Se and Si, the process comprising contacting a carbonyl compound of Formula (1)

(1)

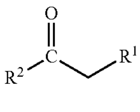

and a nitroso compound of Formula (2)

(2)

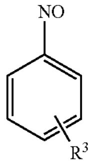

in the presence of

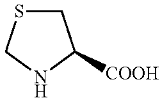

wherein the reaction is carried out in an aqueous solution in the presence of tetra-n-butylammonium bromide.

2. The process of claim 1, comprising allowing a reaction mixture to form upon contacting the carbonyl compound of Formula (1) and the nitroso compound of Formula (2), and allowing the carbonyl compound of Formula (1) and the nitroso compound of Formula (2) to react inthe reaction mixture at a temperature from about 0° C. to about 30° C., thereby allowing the formation of the aminoxy compound of Formula (3).

3. The process of claim 2, wherein the carbonyl compound of Formula (1) and the nitroso compound of Formula (2) are allowed to react for a period of time selected in the range from about 15 minutes to about 24 hours.

4. The process of claim 1, wherein the process is comprised in a process of forming a diol of Formula (8)

(8)

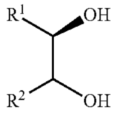

the process further comprising exposing the aminoxy compound of Formula (3) to suitable reduction conditions, thereby obtaining the diol of Formula (8).

5. A process of enantioselectively forming an aminoxy compound of Formula (4)

(4)

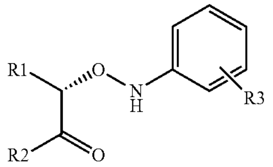

wherein $R^1$ is one of an aliphatic group, an alicyclic group, an aromatic group, an arylaliphatic group and an arylalicyclic group, comprising 0 to about 3 heteroatoms independently selected from the group consisting of N, O, S, Se and Si, $R^2$ is one of hydrogen, an aliphatic group and an alicyclic group, comprising 0 to about 3 heteroatoms independently selected from the group consisting of N, O, S, Se and Si, and $R^3$ is one of hydrogen, halogen, hydroxyl, and an aliphatic group with a main chain having 1 to about 10 carbon atoms and O to about 3 heteroatoms independently selected from the group consisting of N, O, S, Se and Si;

the process comprising contacting a carbonyl compound of Formula (1)

(1)

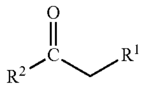

and a nitroso compound of Formula (2)

(2)

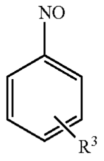

in the presence of

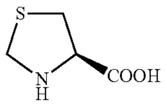

wherein the reaction is carried out in an aqueous solution in the presence of tetra-n-butylammonium bromide.

* * * * *